US012360091B2

(12) United States Patent
Millar et al.

(10) Patent No.: US 12,360,091 B2
(45) Date of Patent: Jul. 15, 2025

(54) PORTABLE GAS ANALYZER

(71) Applicant: Q.E.D. ENVIRONMENTAL SYSTEMS LIMITED, Coventry (GB)

(72) Inventors: Craig Millar, Cubbington (GB); Robert Margrave, Whitnash (GB); Terry Short, Stirchley (GB); Chris Benwell, Ravensthorpe (GB); Iain Clark, Blaby (GB)

(73) Assignee: Q.E.D. Environmental Systems Limited, Coventry (GB)

( * ) Notice: Subject to any disclaimer, the term of this patent is extended or adjusted under 35 U.S.C. 154(b) by 843 days.

(21) Appl. No.: 17/594,751

(22) PCT Filed: May 8, 2020

(86) PCT No.: PCT/IB2020/054394
§ 371 (c)(1),
(2) Date: Oct. 28, 2021

(87) PCT Pub. No.: WO2020/225796
PCT Pub. Date: Nov. 12, 2020

(65) Prior Publication Data
US 2023/0314391 A1      Oct. 5, 2023

Related U.S. Application Data

(60) Provisional application No. 62/949,113, filed on Dec. 17, 2019, provisional application No. 62/845,695, filed on May 9, 2019.

(51) Int. Cl.
*G01N 33/00* (2006.01)

(52) U.S. Cl.
CPC ..... *G01N 33/0031* (2013.01); *G01N 33/0022* (2013.01); *G01N 33/0075* (2013.01)

(58) Field of Classification Search
CPC ........... G01N 33/0031; G01N 33/0022; G01N 33/0075
See application file for complete search history.

(56) References Cited

U.S. PATENT DOCUMENTS

| 6,053,030 A | 4/2000 | Whynall et al. |
| 7,588,726 B1 | 9/2009 | Mouradian et al. |

(Continued)

FOREIGN PATENT DOCUMENTS

| CN | 1301342 A | 6/2001 |
| CN | 102645516 A | 8/2012 |

(Continued)

OTHER PUBLICATIONS

International Search Report and Written Opinion received for corresponding PCT Application No. PCT/IB2020/054394 dated Aug. 27, 2020.

(Continued)

*Primary Examiner* — Jill A Warden
*Assistant Examiner* — Alex Ramirez
(74) *Attorney, Agent, or Firm* — Kinney & Lange, P.A.

(57) ABSTRACT

A portable gas analyzer includes multiple docking stations connected to a pneumatic flowpath through the gas analyzer. Modules are removably mounted to the docking stations. Some modules can be mounted at any one of the docking stations. The modules can include gas sensors and a microcontroller configured to generate data based on signals generated by the gas sensors. The modules are configured to simultaneously form each of electrical, mechanical, and pneumatic connections with the gas analyzer when mounted to the docking station.

17 Claims, 48 Drawing Sheets

(56) References Cited

U.S. PATENT DOCUMENTS

| | | |
|---|---|---|
| 2001/0039824 A1 | 11/2001 | Sunshine et al. |
| 2002/0178789 A1 | 12/2002 | Sunshine et al. |
| 2004/0062684 A1 | 4/2004 | McGee et al. |
| 2012/0024042 A1 | 2/2012 | Vass et al. |
| 2014/0251836 A1 | 9/2014 | Feeney |
| 2017/0131253 A1 | 5/2017 | Gutierrez |
| 2017/0248514 A1* | 8/2017 | Pavey ................ G01N 33/0063 |
| 2018/0120279 A1 | 5/2018 | Yi et al. |

FOREIGN PATENT DOCUMENTS

| | | |
|---|---|---|
| CN | 102778243 A | 11/2012 |
| CN | 103852095 A | 6/2014 |
| CN | 204855482 U | 12/2015 |
| CN | 106018703 A | 10/2016 |
| CN | 107209159 A | 9/2017 |
| CN | 108072739 A | 5/2018 |
| CN | 109069074 A | 12/2018 |
| GB | 201007976 | 6/2010 |
| GB | 2536975 A | 10/2016 |
| IN | 107782850 A | 3/2018 |
| WO | 2000/25108 A1 | 5/2000 |
| WO | 0052444 A2 | 9/2000 |

OTHER PUBLICATIONS

Second Chinese Office Action for CN Application No. 202080034383.8, Dated Nov. 28, 2023, pp. 20.

International Preliminary Report on Patentability for PCT Application No. PCT/IB2020/054394, Dated Nov. 18, 2021, pp. 15.

Chinese Notice of Allowance for CN Application No. 202080034383.8, Dated Mar. 22, 2024, pp. 9.

Li Xuntao; Yu Xiaofen; Hu Jiawen;Li Zhiqiang; Design of wirelessmonitoring network for toxic gases, Journal of Sensing Technology, No. 06, Date Jun. 20, 2010, pp. 1-56.

Y. Li, C. Vancura, et al., Monolithic CMOS multi-transducer gas sensor microsystem for organic and inorganic analytes, Sensors and Actuators B, vol. 126, Dated Apr. 5, 2007, pp. 1-56.

First Chinese Office Action for CN Application No. 202080034383.8, Dated Apr. 15, 2023, pp. 30.

Extended European Search Report for EP Application No. 24182107.3, Dated Sep. 18, 2024, pp. 10.

First Australian Exam Report for AU Application No. 2020269633, Dated Dec. 20, 2024, pp. 2.

* cited by examiner

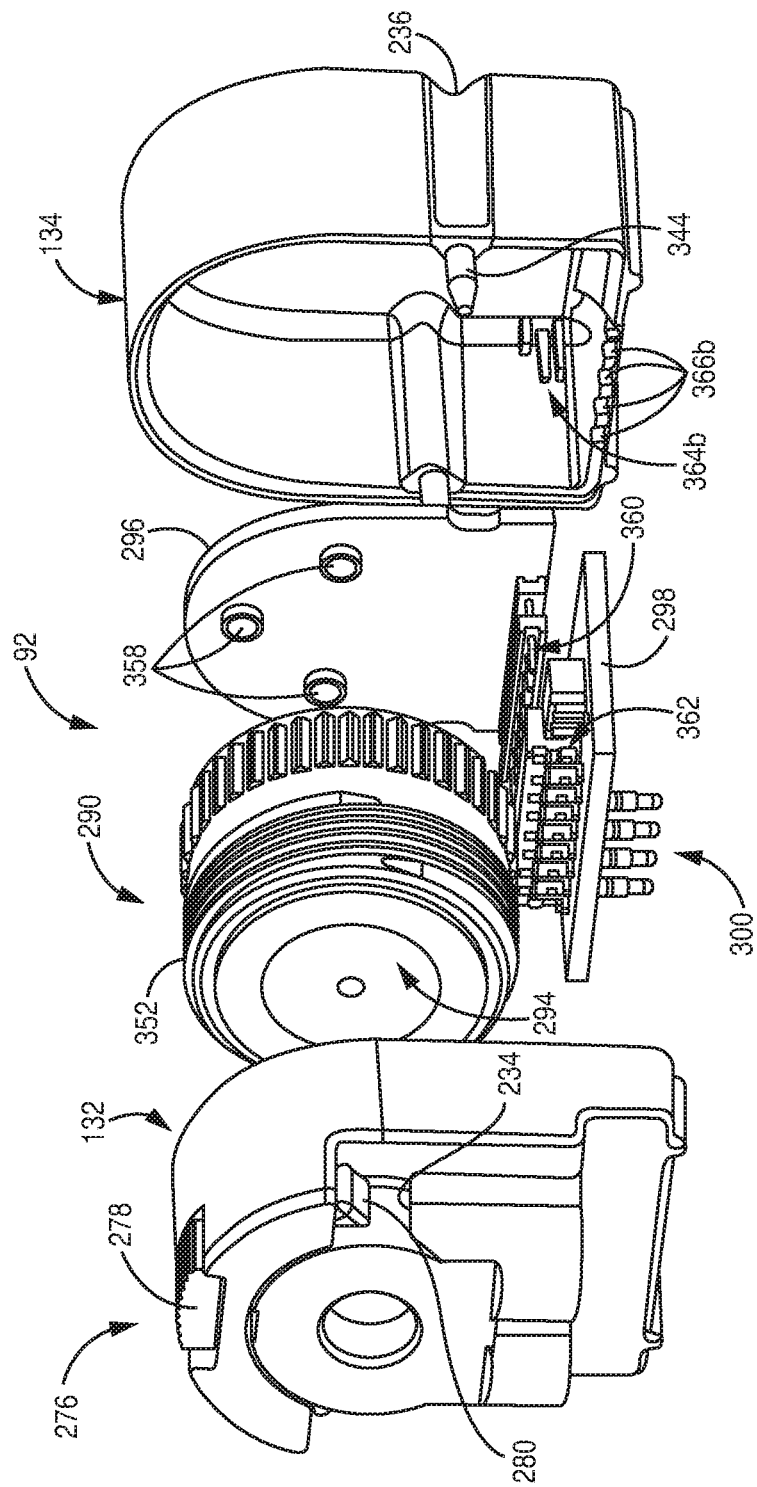

PORTABLE GAS ANALYZER

CROSS-REFERENCE TO RELATED APPLICATION(S)

This application claims the benefit of U.S. Provisional Application No. 62/845,695 filed May 9, 2019 for "PORTABLE LANDFILL GAS ANALYZER MODULE," and this application claims the benefit of U.S. Provisional Application No. 62/949,113 filed Dec. 17, 2019 for "PORTABLE GAS ANALYZER."

BACKGROUND

This disclosure relates to gas analyzers, and in particular, to a hand-portable gas analyzer.

Gas analyzers are used in a many different fields to monitor for presence of specific gases and to provide data regarding parameters of the gasses. Applications of gas analyzers include, for example, scientific and medical research, industrial processes, and environmental monitoring. Some specific examples are analyzing and/or monitoring gasses on landfill sites and during invitro fertilization.

Hand-portable gas analyzers provide the ability to monitor particular gasses of interest at more than one location. For example, a landfill site is populated by landfill wellheads that include pipes extending from underground. A technician with a hand-portable gas analyzer can move about a landfill site and take readings regarding various gasses at the various wellheads within the landfill site.

The gas analyzers include one or more sensors that generate data regarding the gasses, such as temperature, pressure, and concentration, among other parameters. The sensors require periodic calibration to ensure that the sensor is generating accurate data. A sensor outside of its calibration range may generate inaccurate data. The user of the gas analyzer may not know which sensors are within or outside of the specified calibration ranges and thus may be unaware of inaccuracies in the data. The gas data can be stored in records and utilized long after samples are taken and the data is generated.

SUMMARY

According to one aspect of the disclosure, a gas analyzer configured to receive gas and generate data regarding the gas includes a housing; a first sensor module connectable to the housing, the first sensor module configured to generate parameter data regarding a gas; and an analyzer controller. The analyzer controller is configured to receive a first unique module identifier for the first sensor module; and associate the first unique module identifier with the parameter data generated by the first sensor module, thereby generating first associated parameter data.

According to another aspect of the disclosure, a method includes detecting, by an analyzer controller of a gas analyzer, a first sensor module of the gas analyzer, the first sensor module configured to generate first parameter data regarding a gas received by the gas analyzer; receiving, by the analyzer controller, a first unique module identifier of the first sensor module; and associating, by the control circuitry, the first unique module identifier with the first parameter data generated by the first sensor module, thereby generating first associated parameter data.

According to yet another aspect of the disclosure, a handheld gas analyzer including a housing; a gas inlet and a gas outlet; a plurality of internal bays within the housing; a plurality of gas sensor modules, wherein a first subset of the plurality of gas sensor modules are configured to mount in the plurality of bays; and an analyzer controller within the housing. The sensor modules include a transducer for measuring a respective gas property; and programmable module circuitry configured to process signal information from the transducer and output data. The analyzer controller is configured to receive the data output from the plurality of gas sensor modules.

According to yet another aspect of the disclosure, a module assembly for a gas analyzer configured to receive gasses and generate data regarding the gasses includes a plurality of docking stations, wherein each docking station includes a pneumatic inlet and a pneumatic outlet; and a plurality of gas sensing modules disposed within the plurality of docking stations. A first gas sensing module of the plurality of gas sensing modules is mountable to the plurality of docking stations and a second gas sensing module of the plurality of gas sensing modules is mountable to the plurality of docking stations.

According to yet another aspect of the disclosure, a gas sensing module for a gas analyzer includes a housing; a pneumatic chamber; a first pneumatic port fluidly connected to the pneumatic chamber; a second pneumatic port fluidly connected to the pneumatic chamber; a sensing component disposed adjacent the pneumatic chamber and configured to generate information regarding gas within the pneumatic chamber; and an electric connector projecting from the gas sensing module. Mounting the gas sensing module simultaneously forms a pneumatic connection via the first and second pneumatic ports, a mechanical connection, and an electrical connection via the electrical connector.

According to yet another aspect of the disclosure, a method of mounting a gas sensing module within a gas analyzer includes inserting a housing of the gas sensing module into a docking station disposed within the gas analyzer. Inserting the housing into the docking station establishes electrical, pneumatic, and mechanical connections between the gas sensing module and the gas analyzer.

According to yet another aspect of the disclosure, a gas sensing module for a gas analyzer includes a sensor disposed within a housing of the gas sensing module, the sensor configured to generate signals regarding gas within a pneumatic flowpath of the gas sensing module; and a programmable module circuitry disposed within the housing of the gas sensing module, wherein the programmable module circuitry stores configuration data for the gas sensing module.

According to yet another aspect of the disclosure, a gas sensing module for a gas analyzer includes a module body including a pneumatic inlet port and a pneumatic outlet port; a pneumatic chamber fluidly connected to the pneumatic inlet port and the pneumatic outlet port; a sensor mounted to the module body adjacent the pneumatic chamber, the sensor configured to generate signals regarding gas within the pneumatic chamber; and a programmable module circuitry operatively connected to the sensor to receive the signals and configured to generate data regarding the gas based on the signals.

According to yet another aspect of the disclosure, a gas sensing module for a gas analyzer includes a first module body including a pneumatic inlet port; a second module body including a pneumatic outlet port; a pneumatic chamber extending between the first module body and the second module body and fluidly connected to the pneumatic inlet port and the pneumatic outlet port; a sensor configured to generate signals regarding gas within the pneumatic chamber; and a first programmable module circuitry. The sensor includes an infrared (IR) emitter disposed at a first end of the pneumatic chamber; and an IR detector disposed at a second end of the pneumatic chamber, the IR detector configure to generate the signals. The programmable module circuitry is operatively connected to the IR detector to receive the signals and configured to generate data regarding the gas based on the signals.

According to yet another aspect of the disclosure, a gas analyzer configured to receive gas and generate data regarding the gas includes a housing having a front side, a back side, first and second lateral sides, and first and second longitudinal sides; a gas inlet configured to provide gas to a pneumatic pathway in the housing; a gas outlet configured to exhaust gas from the pneumatic pathway; a first module carrier frame disposed within the housing, the first module carrier frame defining a first plurality of docking stations; a first module disposed in the housing and mounted to a first docking station of the first plurality of docking stations. The pneumatic pathway extends serially through the first plurality of docking stations.

According to yet another aspect of the disclosure, a gas analyzer configured to receive gas and generate data regarding the gas includes a housing having a front side, a back side, first and second lateral sides, and first and second longitudinal sides; a first gas inlet configured to provide gas to a pneumatic pathway in the housing; a first gas outlet configured to exhaust gas from the pneumatic pathway; at least one module docking station disposed in the housing and pneumatically connected to the pneumatic pathway; a battery receiving slot formed on the back side of the housing; and a battery pack removably disposed in the battery receiving slot, the battery pack configured to provide power to the at least one module docking station.

According to yet another aspect of the disclosure, a gas analyzer configured to receive gas and generate data regarding the gas includes a housing having a front side, a back side, first and second lateral sides, and first and second longitudinal sides; a pair of sensor module arrays located within the housing; and a removable battery located directly between the pair of sensor module arrays.

BRIEF DESCRIPTION OF THE DRAWINGS

FIGS. 17A-17G are a series of exploded views of an electrochemical gas sensor module.

DETAILED DESCRIPTION

The present disclosure relates to a modular gas analyzer. The gas analyzer can receive parameter data regarding various parameters of a gas sample from various modules associated with the gas analyzer. The gas analyzer can be utilized in a variety of fields, such as scientific and medical research, industrial processes, and environmental monitoring. The gas analyzer can be utilized at landfill sites and for invitro fertilization, among other applications. The gas analyzer can provide data regarding the presence of specific gasses, gas concentrations, temperature, pressure, humidity, and/or pH among other parameters. Each of the modules can have a unique identifier to facilitate discrete tracking of the modules and data. The gas analyzer can include docking stations for inserting the various modules that can generate data regarding parameters of a gas flowing through the gas analyzer. The docking stations can receive different module types, allowing the user to swap modules and configure the gas analyzer to a particular task or job site. The gas analyzer is field configurable, allowing the user to add, remove, or swap modules in the field to alter the sensing capabilities of the gas analyzer. The below discussion is focused on use in a landfill site for purposes of example, but it is understood that the discussion applies equally to other fields, such as invitro fertilization.

Figure 1:
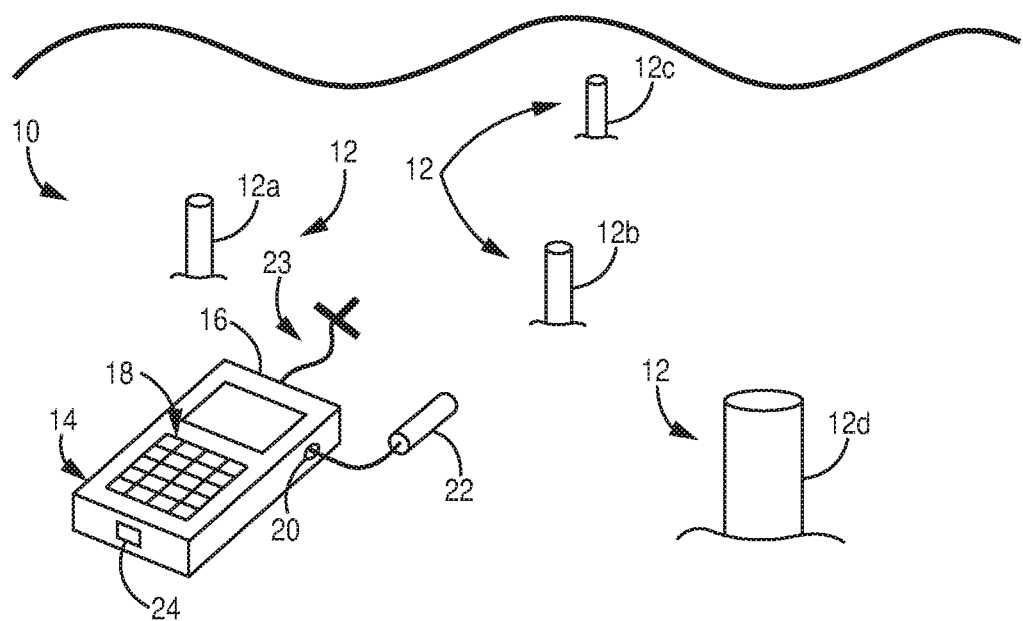
FIG. 1 is a schematic view of a landfill site.

FIG. 1 is a schematic diagram of a landfill site 10 including wellheads 12a-12D (collectively herein "landfill wellheads 12") and gas analyzer 14. Gas analyzer 14 includes housing 16, user interface 18, sensor port 20, sensor module 22, data port 24, and gas collector 23.

Landfill site 10 is covered in earth, burying refuse on the site 10. The landfill site 10 is populated by a plurality of landfill wellheads 12. The landfill wellheads 12 include pipes extending from underground, and can allow for sampling and/or collection of liquid (e.g., leachate) and/or gas (e.g., methane) from within the landfill site 10. The landfill wellheads 12 are generally capped and can include ports for inserting one or more sensors, exposing the sensors to the internal landfill environment. In this way, the landfill wellheads 12 can be used for measuring the presence of particular types of liquids and/or gas as well as the properties of these liquids and gases.

The landfill site 10 can be monitored for a variety of gasses. For example, methane is one gas that can be monitored at landfill sites 10. The production of methane can be indicative of the status of the landfill. Furthermore, leakage of methane gas is undesirable, such that the presence of methane gas and its properties (e.g., pressure, temperature, concentration) are monitored. Methane gas rises up the wells into the landfill wellheads 12. The landfill wellheads 12 can be capped to prevent the escape of methane gas, and in some cases the landfill wellheads 12 can route the methane gas to collection systems for capture.

Gas analyzer 14 is utilized to collect samples of gas from landfill wellheads 12 and includes sensor modules configured to generate data regarding the gas. Housing 16 supports other components of gas analyzer 14, such as an analyzer controller, user interface 18, and various sensing modules. Housing 16 can be a metal and/or polymer enclosure, which in some cases can have a six-sided, box profile.

Figure 3:
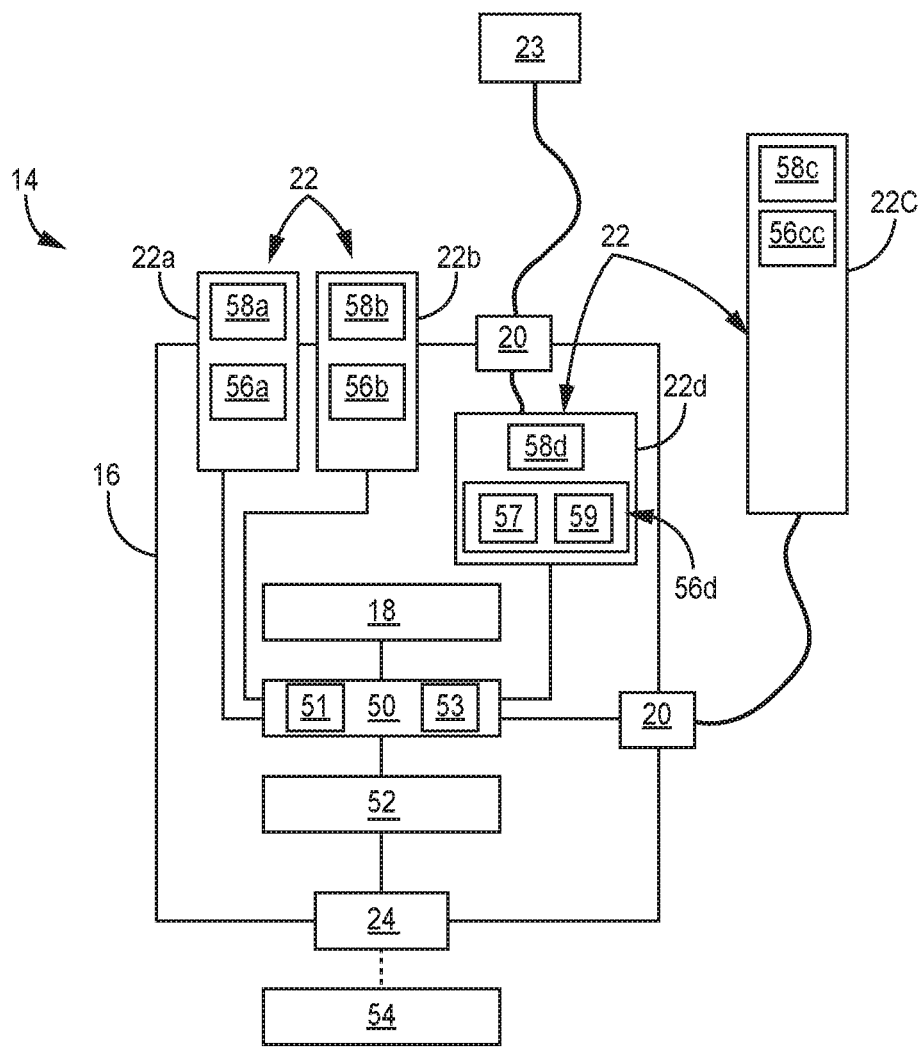
FIG. 3 is a simplified block schematic diagram of a modular hand-portable gas analyzer.
Figure 4:
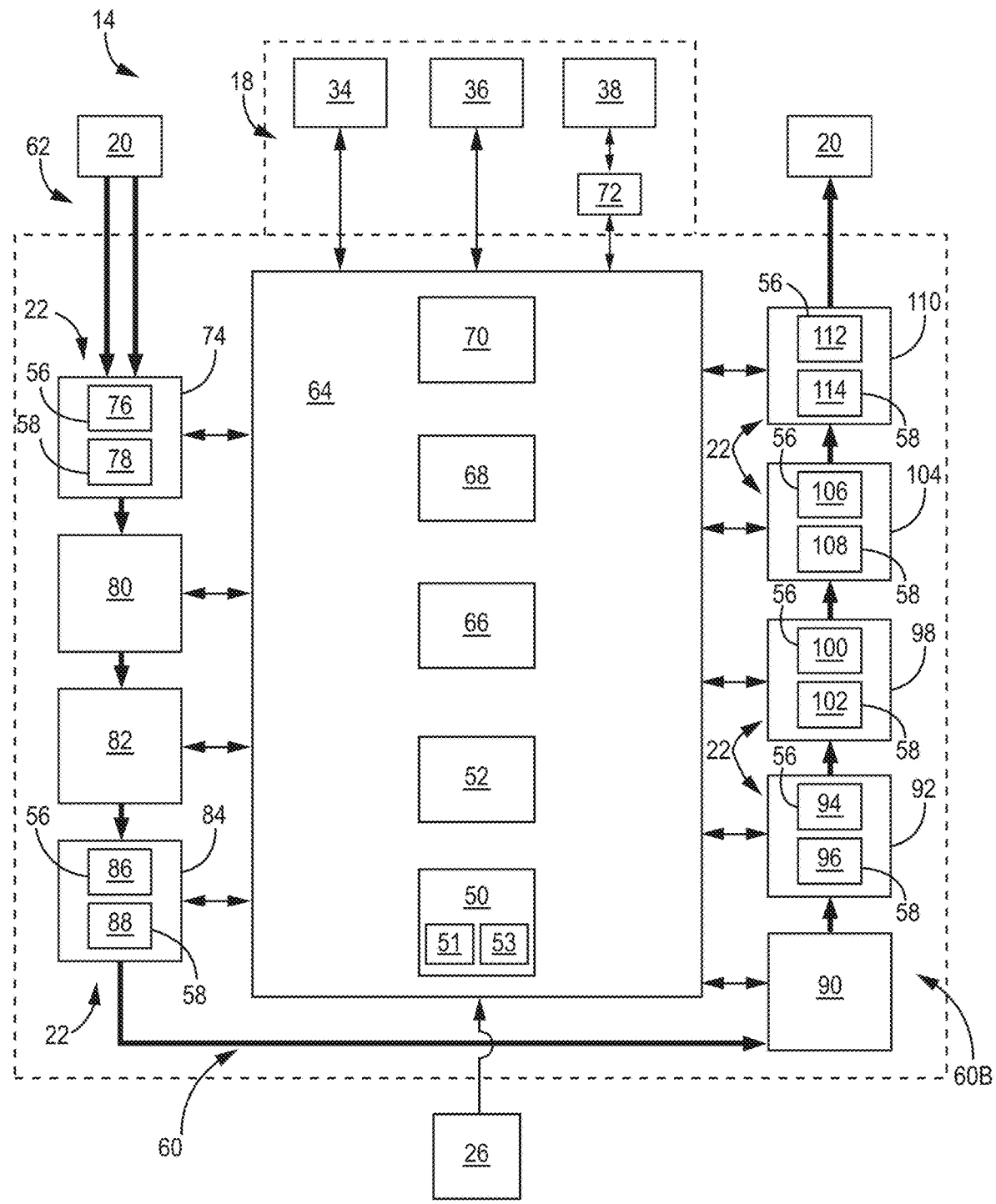
FIG. 4 is a block schematic diagram of a modular hand-portable gas analyzer showing multiple internally mounted modules.

User interface 18 can include a screen (e.g., a touchscreen), one or more buttons, dials, switches, or other inputs. User interface 18 can include a speaker for outputting audio messages and/or microphone for inputting audio commands. It is understood that user interface 18 can be any graphical and/or mechanical interface that enables user interaction with analyzer controller 50 (FIGS. 3 and 4). For example, user interface 18 can implement a graphical user interface displayed at a display device of user interface 18 for presenting information to and/or receiving input from a user. User interface 18 can include graphical navigation and control elements, such as graphical buttons or other graphical control elements presented at the display device. User interface 18, in some examples, includes physical navigation and control elements, such as physically actuated buttons or other physical navigation and control elements. In general, user interface 18 can include any input and/or output devices and control elements that can enable user interaction with analyzer controller 50 and is not limited to what is described and/or shown herein.

Sensor module 22 is operatively connected to the controller 50 of gas analyzer 14. For example, sensor module 22 can be communicatively and/or electrically connected to the controller 50. The sensor module 22 shown in FIG. 1 is disposed outside of housing 16 and connected to housing 16 and components within housing 16 via sensor port 20. It is understood, however, that gas analyzer 14 can include multiple sensor modules 22 disposed wholly outside of housing 16, partially within and partially outside of housing 16, or fully within housing 16. As discussed in more detail below, the various sensor modules 22 can be removably connected to and/or within housing 16 such that the sensor modules 22 are not permanently fixed relative housing 16. Each sensor module 22 can include its own housing separate from housing 16. The housing of each sensor module 22 can be formed from polymer, glass, and/or metal. In some examples, the sensor modules 22 disposed within housing 16 can be serially connected along a common pneumatic flowpath such that a gas sample flows serially through the sensor modules 22.

The multiple sensor modules 22 can be simultaneously connected to the rest of the portable gas analyzer device 14. Each sensor module 22 can generate data regarding the gas sampled from landfill wellhead 12. Each sensor module 22 can measure a different parameter. In some examples, gas analyzer 14 can include multiple sensor modules 22 configured to generate data regarding the same parameter. As discussed in more detail below, gas analyzer 14 is modular such that various ones of sensor modules 22 configured to generate data regarding a variety of parameters of the gas can be added, removed, or swapped in the field to upgrade and/or update gas analyzer 14. For example, a first sensor module 22 can measure methane gas concentration, a second sensor module 22 can measure gas pressure, any third sensor module 22 can measure temperature. Multiple sensor modules 22 can be inserted into a landfill wellhead 12 at the same time so that measurements of different parameters can be simultaneously taken. Sensor modules 22a-22c can be inserted into the landfill wellhead 12 simultaneously with gas collector 23 such that multiple sensor modules 22 disposed inside and outside of housing 16 can simultaneously generate data regarding the gas. In some examples, sensor modules 22a and 22b are also connected to individual gas collectors 36 or to a pneumatic flowpath within housing 16 that receives gas from a gas collector 23.

During sampling, a technician can move about the landfill site 10 to sample liquid/and or gases at the landfill wellheads 12. For conducting the sampling, the technician can carry portable gas analyzer device 14 between wellheads. The portable gas analyzer device 14 is lightweight such that it is handheld and portable (e.g., gas analyzer 14 can weigh less than about 9.07 kilograms (about 20 pounds)). The portable gas analyzer device 14 can be carried to multiple landfill wellheads 12 for sampling in a day. The sampling at each landfill wellhead 12 can take less than about 20 minutes, during which sampling the technician may continue to hold the portable gas analyzer device 14.

Gas collector 23 is disposed outside of housing 16 and is connected to housing 16 by pneumatic tubing. Gas collector 23 can be inserted into the landfill wellhead 12 to collect the gas sample from that wellhead. The pneumatic tubing can convey gasses from the landfill wellhead 12 to sensor modules 22 disposed wholly or partially within gas analyzer 14. The sensor module 22 shown in FIG. 1 can also be partially or fully inserted into a landfill wellhead 12 for sampling the gas within. Each sensor module 22 can also be entirely removed, and disconnected, from gas analyzer 14.

The sensor module 22 can be connected to the rest of the portable gas analyzer device 14 by a cord that can plug in to sensor port 20. The cord can be a tether configured to mechanically connect sensor module 22 to gas analyzer 14. Additionally or alternatively, the cord can provide a communication link between sensor module 22 and analyzer controller 50 of gas analyzer 14. In some examples, sensor module 22 can be wirelessly connected to the portable gas analyzer device 14, such as by radiofrequency communications. For example, sensor module 22 can communicate with analyzer controller 50 utilizing short-wavelength ultra high frequency (UHF) radio waves in the 2.4 GHz band (2.400-2.525 GHz) (e.g., Bluetooth® communications). In another example, the communications circuitry can be configured for communications utilizing super high frequency (SHF) radio waves in the 5 GHz band. It is understood, however, that sensor module 22 can be configured to communicate in any desired manner over any suitable frequency.

Figure 2A:
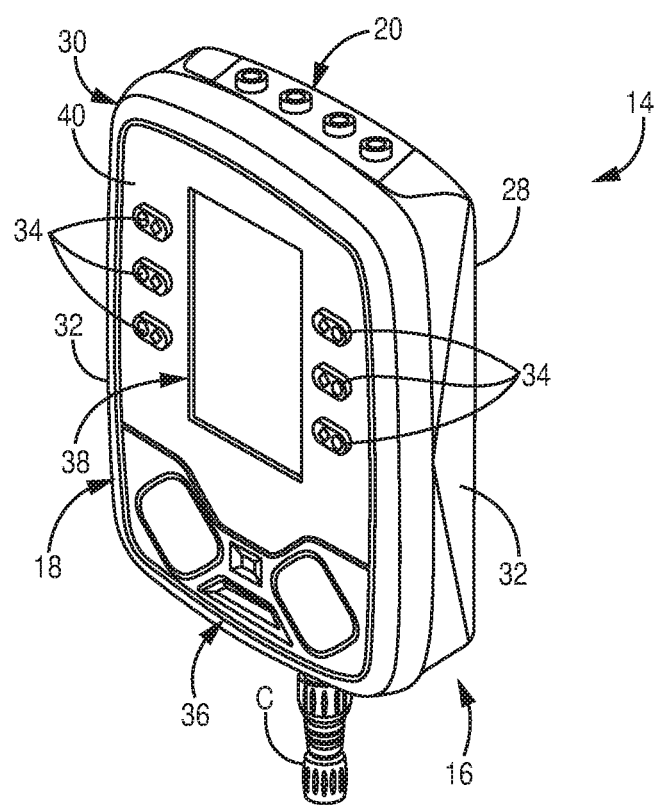
FIG. 2A is an isometric front view showing a case front and user interface of a modular hand-portable gas analyzer.
Figure 2B:
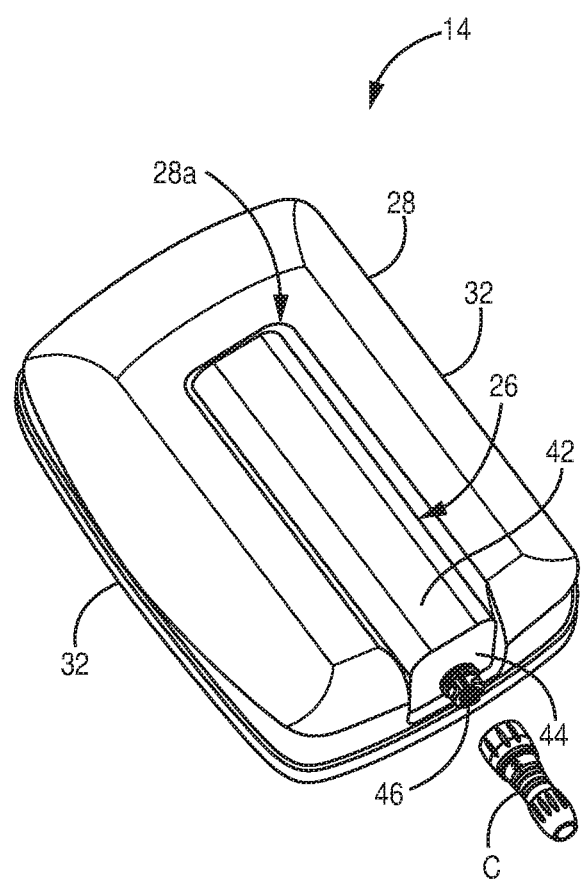
FIG. 2B is an isometric rear view showing a case back and a battery pack of the modular hand-portable gas analyzer.
Figure 2C:
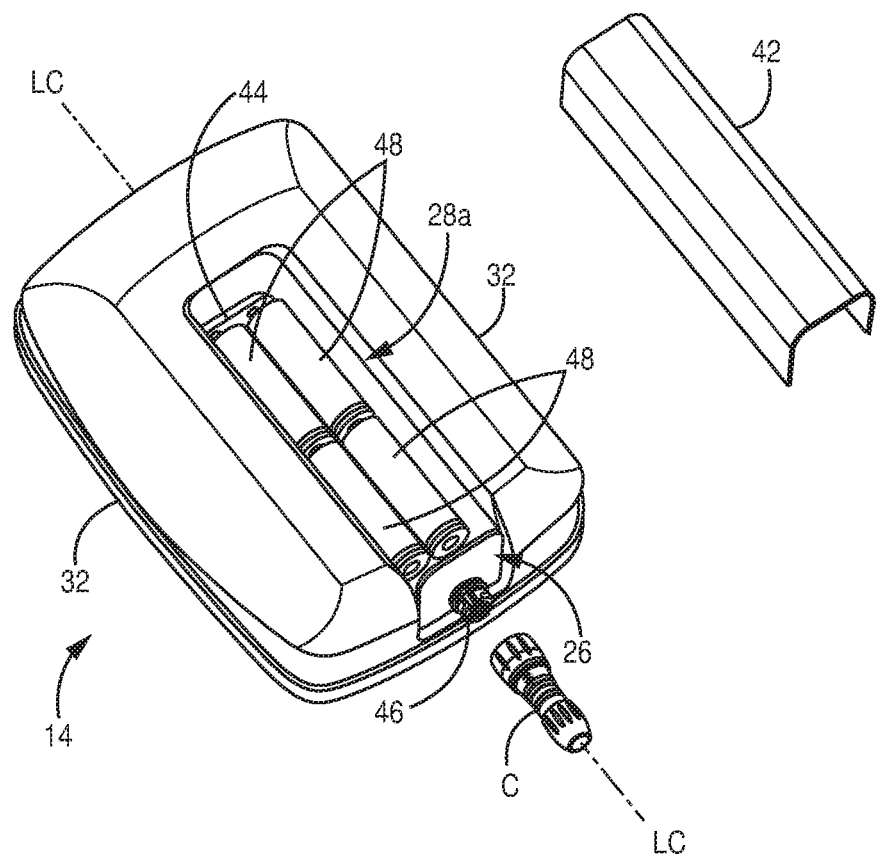
FIG. 2C is an isometric view of the modular hand-portable gas analyzer shown in FIG. 1B with a battery pack cover removed.

FIGS. 2A-2C show a hand-portable gas analyzer 14, which includes housing 16, user interface 18, ports 20, and battery pack 26. Housing 16 includes case back 28 (with battery pack receptacle slot 28a), case top 30, and lateral sides 32. User interface 18 includes upper keypads 32, lower keypads 34, display 36, and panel 38. Battery pack 26 includes battery case lid 42, battery base 44, connector 46, and battery cells 48). Also shown is connector C, which mates with connector 46 for charging of the battery cells 48 in battery pack 26.

Battery pack 26 provides the electrical power to components of gas analyzer 14 to operate gas analyzer 14. Battery pack 26 is removably mounted in slot 28a. Battery pack 26 can be removed from slot 28a and replaced with another fully charged battery pack 26. Battery pack 26 can be configured to be vertically inserted and removed from battery slot 28a and/or longitudinally removed from battery slot 28a. In the example shown, battery slot 28a is open on a lower longitudinal end of gas analyzer 14 to facilitate sliding longitudinal removal of battery pack 26. It is understood, however, that battery slot 28a and battery pack 26 can be configured in any desired manner to facilitate sliding installation and removal of battery pack 26. Battery pack 26 can be charged both when mounted in slot 28a and when removed from slot 28a. This is advantageous when gas analyzer 14 is being used for long periods of time, such as when performing tests in a large landfill site 10 (FIG. 1). In those situations, access to facilities where recharging can be performed may be limited. The user can instead simply remove the depleted battery pack 26, replace with a charged battery pack 26, and continue sampling.

Battery pack 26 is configured such that battery pack 26 can be utilized and replaced in hazardous areas where explosive atmosphere may occur. Battery pack 26 is configured such that battery pack 26 can be utilized and replaced both Zone 1 and Zone 2 hazardous areas. A Zone 1 hazardous area is an area in which an explosive gas atmosphere is likely to occur in normal operation. A Zone 2 hazardous area is an area in which an explosive gas atmosphere is not likely to occur in normal operation and, if it occurs, will only exist for a short time. For example, battery pack 26 can be replaced while being utilized at landfill site 10 where methane can be present. While battery case lid 42 is shown as removed from battery pack 26 in FIG. 2C, it is understood that battery case lid 42 is configured to be permanently fixed to battery base 44 such that battery pack 26 is a single unit. Battery pack 26 is not meant to be disassembled to provide access to individual battery cells 48. While battery pack 26 is shown as including four battery cells 48, it is understood that battery pack 26 can include as many or as few battery cells 48 as desired. In some examples, battery pack 26 includes eight battery cells 48, which provides a longer life of battery pack 26. Battery cells 48 can be lithium-ion or nickel metal hydride, among other options.

Slot 28a is elongate along a longitudinal centerline LC of gas analyzer 14. During operation, the user typically grasps the two lateral sides 32 of gas analyzer 14. Battery pack 26 is a relatively heavy component of gas analyzer 14. Having slot 28a, and thus battery pack 26, elongate along the longitudinal centerline LC of gas analyzer 14 balances the weight of gas analyzer 14 in the user's hands. As such, gas analyzer 14 is more ergonomic and easier for the user to operate over extended periods.

User interface 18 is exposed to the user on case top 30. Panel 40 and upper keypads 34 and lower keypads 36 are mounted on an outer surface of case top 30. Upper keypads 34 extend through openings in panel 40. Display 38 can be located behind panel 40, such as when panel 40 is a glass panel. Panel 40 provides an ingress seal to stop water entering the device. Panel 40 can provide a touchscreen interface for navigating within and using the gas analyzer 14. In some examples, panel 40 can be made from thickened glass, such as up to about 3 millimeters (mm) (about 0.19 inches (in.)) and can be toughened.

Battery pack 26 interfaces with a baseboard of gas analyzer 14 to provide power to gas analyzer 14 and various components within gas analyzer 14 via that baseboard. Upper keypads 34, lower keypads 36, and display 38 are electronically connected to the baseboard disposed within gas analyzer 14. Upper keypads 34, lower keypads 36, and display 38 provide user interface 18 for the user to provide information to and receive information from components of gas analyzer 14. Upper keypads 34 and lower keypads 36 can be backlit to facilitate use in low-light conditions. In addition, one of upper keypads 34 and lower keypads 18 can include a button configured to disable the touchscreen interface, in examples including such a touchscreen, which facilitates use of gas analyzer 14 in poor weather conditions.

FIG. 3 is a simplified schematic block diagram of gas analyzer 14 further showing remote computing device 54. Housing 16, user interface 18, sensor ports 20, sensor modules 22a-22d (collectively herein "sensor modules 22"), data port 24, analyzer controller 50, and transmission circuitry 52. Sensor modules 22a-22d respectively include programmable module circuitry 56a-56d (collectively herein "programmable module circuitry 56") and transducers 58a-58d (collectively herein "transducers 58").

Analyzer controller 50 is disposed within housing 16 and is operatively connected to other components of gas analyzer 14. Analyzer controller 50 is configured to perform any of the functions discussed herein, including receiving an output from any sensor referenced herein, detecting any condition or event referenced herein, and controlling operation of any components referenced herein. Analyzer controller 50 can be of any suitable configuration for controlling operation of gas analyzer 14, gathering data, processing data, etc. Analyzer controller 50 can include logic hardware and further firmware, software, and/or other logic instructions. Analyzer controller 50 is configured to store software, implement functionality, and/or process instructions. Analyzer controller 50 can be entirely or partially mounted on one or more boards. In some examples, analyzer controller 50 can be implemented as a plurality of discrete circuitry subassemblies. The analyzer controller 50 can include one or more of a microprocessor, a controller, a digital signal processor (DSP), an application specific integrated circuit (ASIC), a field-programmable gate array (FPGA), or other equivalent discrete or integrated logic circuitry. In some examples, analyzer controller 50 can include and/or be formed by a system on module (SOM). For example, analyzer controller 50 can include control circuitry 51 and memory 53 in communication with the control circuitry, the memory storing program instructions executable by the control circuitry to carry out any of the functions referenced herein.

The memory can be described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, the memory is a temporary memory, meaning that a primary purpose of the memory is not long-term storage. The memory, in some examples, is described as volatile memory, meaning that the memory does not maintain stored contents when power to analyzer controller 50 is turned off. Examples of volatile memories can include random access memories (RAM), dynamic random access memories (DRAM), static random access memories (SRAM), and other forms of volatile memories. The memory, in one example, is used by software or applications running on the control circuitry to temporarily store information during program execution. The memory, in some examples, also includes one or more computer-readable storage media. The memory can further be configured for long-term storage of information. The memory can be configured to store larger amounts of information than volatile memory. In some examples, the memory includes non-volatile storage elements. Examples of such non-volatile storage elements can include magnetic hard discs, optical discs, floppy discs, flash memories, or forms of electrically programmable memories (EPROM) or electrically erasable and programmable (EEPROM) memories.

Sensor modules 22 are configured to generate data regarding parameters of a gas, such as the presence of specific gasses, gas concentrations, temperature, pressure, humidity, and/or pH among other parameters. Each sensor module is connected to housing 16. Sensor module 22a includes transducer 58a. Sensor module 22b includes transducer 58b. Sensor module 22c includes transducer 58c. Sensor module 22d includes transducer 58d. Each transducer 58 can be used for sensing and generating data regarding a parameter of the gas. For example, one of transducers 58a-58d can measure methane gas concentration, one of transducers 58a-58d can measure gas pressure, one of transducers 58a-58d can measure temperature, one of transducers 58a-58d can measure oxygen concentration, among other parameters. The sensor module 22 for generating temperature data is typically disposed remote from gas analyzer 14 such that that sensor module 22 can be inserted directly into landfill wellhead 12 (FIG. 1) to generate accurate temperature data.

Sensor module 22a includes programmable module circuitry 56a. Sensor module 22b includes programmable module circuitry 56b. Sensor module 22c includes programmable module circuitry 56c. Sensor module 22d includes programmable module circuitry 56d. Each programmable module circuitry 56 can include module circuitry 57, which can be similar to control circuitry 51, and memory 59, which can be similar to memory 53. While programmable module circuitry 56d is illustrated as including control circuitry 57 and memory 59, it is understood that each programmable module circuitry 56a-56d can include control circuitry 57 and memory 59. Programmable module circuitry 56 can include one or more of a microprocessor, a controller, a digital signal processor (DSP), an application specific integrated circuit (ASIC), a field-programmable gate array (FPGA), or other equivalent discrete or integrated logic circuitry.

The memory of each programmable module circuitry 56 can be described as computer-readable storage media. In some examples, a computer-readable storage medium can include a non-transitory medium. In some examples, the memory is a temporary memory, meaning that a primary purpose of the memory is not long-term storage. The memory, in some examples, is described as volatile memory, meaning that the memory does not maintain stored contents when power to programmable module circuitry 56 is turned off. Examples of volatile memories can include random access memories (RAM), dynamic random access memories (DRAM), static random access memories (SRAM), and other forms of volatile memories. The memory, in one example, is used by software or applications running on the control circuitry of the module 22 to temporarily store information during program execution. The memory, in some examples, also includes one or more computer-readable storage media. The memory can further be configured for long-term storage of information. The memory can be configured to store larger amounts of information than volatile memory. In some examples, the memory includes non-volatile storage elements.

The programmable module circuitry 56a-56d can receive signals from transducers 58a-58d. For example, programmable module circuitry 56 can receive an analog signal from a transducer 58 and can digitize, save, and/or transmit the signal and/or data (if the signal was digitized) to the analyzer controller 50. The analyzer controller 50 can save the signal and/or data in memory of the analyzer controller 50, and can transmit the saved signal and/or data via the transmission circuitry 52 to the external computing device 54.

Sensor modules 22a and 22b are inserted into respective slots in housing 16 such that sensor modules 22a and 22b are partially disposed within housing 16 and partially exposed outside of housing 16. Sensor modules 22a and 22b can be slit out of the slots in housing 16 for detachment from housing 16. In some examples, mechanical and electrical connections are formed by inserting sensor modules 22a and 22b into associated respective slots. The mechanical connection is formed between sensor modules 22a and 22b and housing 16 to secure sensor modules 22a and 22b in the slots. The electrical connection is formed between sensor modules 22a and 22b and a power supply of gas analyzer 14, such as a battery as discussed in more detail below. The electrical connection is further formed between sensor modules 22a and 22b and analyzer controller 50 for data communication.

Sensor module 22c is shown as disposed external to housing 16 and connected to gas analyzer 14 by a wired connection via one of sensor ports 20. The wired connection can mechanically and/or electrically connect sensor module 22c to gas analyzer 14. In some examples, sensor module 22c is configured to communicate wirelessly with analyzer controller 50. Sensor module 22c being disposed remote from housing 16 facilitates insertion of sensor module 22c into a landfill wellhead 12 (FIG. 1).

Sensor module 22d is disposed within housing 16. Gas collector 23 is disposed remote from housing 16 and is connected to housing 16 at one of sensor ports 20 via pneumatic tubing. A pneumatic pathway extends within housing 16 from the sensor port 20 associated with gas collector 23 to sensor module 22d. The pneumatic pathway provides gasses to sensor module 22d during operation. In some examples, mechanical and electrical connections are formed when sensor module 22d is mounted within housing 16. In some examples, a pneumatic connection with an internal pneumatic pathway in gas analyzer 14 is also formed upon insertion of sensor module 22d into housing 16. The mechanical connection is formed between sensor module 22d housing 16 to secure sensor module 22d at a mounting location within housing 16. The electrical connection is formed between sensor module 22d and a power supply of gas analyzer 14, such as a battery as discussed in more detail below. The electrical connection is further formed between sensor module 22d and analyzer controller 50 for data communication.

Analyzer controller 50 can output control signals to any of the electronic components, including, without limitation, sensor modules 22a-22d, transmission circuitry 52, sensor port 20, and/or user interface 18. Analyzer controller 50 can also receive signals, such as from sensor modules 22a-22d, transmission circuitry 52, sensor port 20, and/or user interface 18. In some examples, analyzer controller 50 can include an internal clock recording temporal data associated with measurement data generated by sensors 22a-22d. The temporal data can include date (e.g., day-month-year) and time (hours-minutes-seconds) at or near which the measurement data was generated. While analyzer controller 50 is shown as a separate component, other components of the gas analyzer 14 can include logic circuitry for managing, to at least some degree, their own function, such as the user interface 18 and transmission circuitry 52.

Transmission circuitry 52 is circuitry for transmitting data from gas analyzer 14 to remote computing device 54. Remote computing device 54 can be any type of computing device, such as a portable computing device (e.g., smart phone, tablet computer), a personal computer (e.g., desktop computer, laptop computer), a cellular network, or a server, amongst other options. In some cases, a wired connection may be established between the transmission circuitry 52 and the external computing device 54, such as via data port 24. Additionally or alternatively, the transmission circuitry 52 can support wireless communication to the external computing device 54, such as via Bluetooth, Wi-Fi, or other wireless communication protocol. While a single external computing device 54 is shown, the transmission circuitry 52 can bidirectionaly communicate with multiple external computing devices 30, in some embodiments individually, in some embodiments simultaneously. The connection between transmission circuitry 52 and external computing device 54 can be used to export data from portable gas analyzer device 14 to external computing device 54. The connection between transmission circuitry 52 and external computing device 54 can further be used to import data to gas analyzer 14 from external computing device 54. If the external computing device 54 is part of a network, then the external computing device 54 can communicate the data to other devices within the network.

During operation, gas analyzer 14 is utilized to take gas samples. Sensor modules 22 generate parameter data regarding the parameter that that sensor module 22 is configured to sense. The parameter data generated by each sensor module 22 is only as accurate as the transducers 58 of that sensor module 22. An operator of gas analyzer 14 may want to establish the integrity of the parameter data by reference to the particular transducer 58 used to collect the data. For example, one type of transducer 58 may be inherently more accurate than another type of transducer 58. The transducers 58 require periodic calibration to ensure the integrity of any data generated. A first transducer 58 may be within its calibration period while a second transducer 58 may be outside of its calibration period.

When viewing collected data at a later time, the viewer of data might not have the sensor module 22 or portable gas analyzer device 14 accessible, and might not know which data was sensed by which transducer 58, sensor module 22, or portable gas analyzer device 14, and then might not have reason to know either of which types of transducers 58 were used for sensing or the calibration statuses of those transducers 58 at the time the data was generated. As further discussed herein, each sensor module 22 can be uniquely tracked to differentiate different sensor modules 22 from each other (even though the sensor modules 22 may be identical models and may include operatively identical transducers 58). Such tracking facilitates reference to calibration records to verify data integrity long after the data is generated.

To track each sensor module 22, each sensor module 22 has a unique module identifier (ID) associated with that particular sensor module 22. Although a plurality of sensor modules 22 can be identical models, manufactured at the same time and physically indistinguishable, each can have a different unique module ID. For example, no two sensor modules 22 may have the same unique module ID. Each unique module ID can be unique to the transducer 58 and/or the particular sensor module 22 as a whole. In some cases, such as where a single sensor module 22 includes multiple transducers 58, then a single sensor module 22 can include multiple unique module IDs associated with each of the transducers 58 of the single sensor module 22.

The unique module ID can be stored in the programmable module circuitry 56 of the sensor module 22 with which the unique module ID is uniquely associated. Additionally or alternatively, the unique module ID can be graphically represented on that particular sensor module 22, such as via a code printed on the sensor module 22. For example, the code representing the unique sensor module ID could be a series of alphanumeric characters including letters and/or numbers, and additionally or alternatively can be a barcode, QR code, or other optically scannable graphic code.

Separate records can be kept linking the unique module ID to the biographical history of the particular sensor module 22. The biographical history can include the manufacturer of the sensor module 22, model number of the sensor module 22, type of sensor, age of the sensor module 22, calibration status of the particular sensor module 22, utilization (e.g., samples taken, duration of use, etc.) since the last calibration, etc. Each unique module ID can be associated with a respective transducer 58. In this way, each transducer 58 can have a unique module ID, and the multiple transducers 58 (e.g., 58a-58d) can be associated with different unique sensor module IDs.

Each unique module ID can be issued at the factory as part of manufacturing of the sensor module 22. In some cases, the unique module ID can be the serial number of the sensor module 22. In some examples, the unique module ID is a number different than the serial number. In some examples, the unique module ID is not generated by the analyzer controller 50 based on connection with the portable gas analyzer unit 14, but rather is permanent with the sensor module 22 so that the sensor module 22 can connect to various different portable gas analyzer units 14 and the data generated by the sensor module 22 can still be individually tracked regardless of the portable gas analyzer unit 14 with which the sensor module 22 is or was connected. The sensor module ID can be saved in the memory of the programmable module circuitry 56, printed on the sensor module 22, printed on packaging for the sensor module 22, and/or kept as a record (written or digital) separate from the sensor module 22. In some examples, the unique module ID can be generated by analyzer controller 50 and provided to sensor module 22 on power up of gas analyzer 14. In some examples, the unique module ID generated by analyzer controller 50 can be permanently stored in the memory of sensor module 22 such as in a read-only format.

It is useful to keep a record of which sensor module 22, and which transducer 58 in particular, was used to generate which parameter data. Such records can be accessed at a later time, such as years after the data was taken, to provide evidence of data accuracy and integrity. The unique module ID of a particular sensor module 22 can be saved and transmitted with the data that the transducer 58 of that sensor module 22 collected. For example, the programmable module circuitry 56 can transmit its unique module ID and the data received from the transducer 58 to analyzer controller 50 and the analyzer controller 50 can save the unique module ID in association with the parameter data. In some examples, module circuitry 56 can be configured to associate the unique module ID of its sensor module 22 and/or transducer 58 with the parameter data, thereby generating associated parameter data, prior to transmitting the data to analyzer controller 50. The programmable module circuitry 56 can thereby be configured to generate and transmit associated parameter data. In some examples, the analyzer controller 50 can receive unique module IDs for each sensor module 22 prior to operation of gas analyzer 14. Analyzer controller 50 can save the unique module IDs in the memory of analyzer controller 50. Analyzer controller 50 can then generate associated parameter data based on the parameter data received from a particular sensor module 22 and based on the unique module ID of that particular sensor module 22. The associated parameter data can be further associated with locational data, such as latitude and longitude or the particular job site where the gas is sampled, and temporal data, among other data types, to generate sample-specific parameter data.

The analyzer controller 50 can later transmit the unique sensor module ID, sample data, and the parameter data to the external computing device 54. The unique sensor module ID, sample data, and parameter data can be saved by the external computing device 54 and/or other computing device for later retrieval. Upon retrieval, the unique sensor module ID can be used to identify (e.g., by a table or other archive) information regarding the sensor module 22 and/or transducer utilized to generate the data. For example, the type of transducer 58 used to collect the data as well as the calibration records of the transducer 58 can be recalled. The temporal data can be used to confirm the age and calibration status of the transducer 58 from when the data was generated to provide evidence that the particular data is reliable.

In some examples, the unique module ID is not saved in the programmable module circuitry 56 of the sensor module 22. For example, one or more of the sensor modules 22 may not include programmable module circuitry 56. In such cases, control circuitry 26 can prompt the user via user interface 18 to provide the unique module ID to gas analyzer 14 for saving in analyzer controller 50. Control circuitry 26 can associate the user-supplied unique module ID with the parameter data generated by the sensor module 22 to generate the associated parameter data. Analyzer controller 50 can further associate the data with sample data, such as temporal data. Analyzer controller 50 can transmit the associated data to the external computing device 54. In such cases, the user can read the unique module ID as printed on the sensor module 22, scan the unique module ID if in graphic code, or otherwise manually or semi-manually input the unique module ID to the analyzer controller 50 of gas analyzer 14 via user interface 18. In some examples, analyzer controller 50 can prevent gas analyzer 14 from operating to generate parameter data until each sensor module 22 of the gas analyzer 14 is associated with a unique module ID.

Each landfill site 10 can have an identifier name associated with it, such as a unique name that uniquely identifies a particular landfill site 10 from other landfill sites. The identifier of the landfill site 10 can be an address or coordinate of the particular landfill site 10. Within each landfill site 10, each landfill wellhead 12 can have an identifier associated with the particular landfill wellhead 12, such as a identifying name, code, coordinate, or other identifier that differentiates the particular landfill wellhead 12 from the other landfill wellheads 12 at the same landfill site 10. The identifiers for each of the landfill site 10 and the landfill wellhead 12 at which a reading is being taken by the gas analyzer 14 can be input into the portable gas analyzer device 14 (e.g., previously uploaded via data port 24 and/or transmission circuitry 52, or manually input by the operator via the interface 18). The analyzer controller 50 can store the identifiers for the landfill site 10 and a plurality of landfill wellheads 12 at the particular landfill site 10. When at the particular landfill site 10, the operator can select or otherwise input the particular landfill site 10 at which measurements will take place for the current session. At each landfill wellhead 12, just before, during, or just after measurement (e.g., after the operator is done taking measurements at the previous landfill wellhead 12 and before taking measurements at the next landfill wellhead 12), the operator can select or otherwise input the particular landfill wellhead 12 at which the data being collected is/will be/was generated. When the analyzer controller 50 is saving the parameter data of the particular landfill wellhead 12, in addition to saving the unique sensor module ID, the analyzer controller 50 can also save the identifier for the landfill site 10, and/or the identifier for the particular landfill wellhead 12, in association with the data generated at that particular landfill wellhead 12. Analyzer controller 50 can thereby generate sample-specific parameter data based on the site data and the associated parameter data.

As the operator moves to different landfill wellheads 12, generating parameter data at each, a table can be built of the data discussed herein and stored by analyzer controller 50. The table can be transmitted to the external computing device 54 as explained herein. While a table is used by way of example, it is understood that the data can be stored in any desired format. A sample of such a table is shown below.

TABLE 1

| Site | Wellhead | Date | Time | CH4 concentration | CH4 Sensor Module ID | Gas pressure | Pressure Sensor Module ID | Gas Temp | Gas Sensor Module ID |
|---|---|---|---|---|---|---|---|---|---|
| Greenacre #5 | 34-1 | 4 May 2019 | 7:25:33 | 445 PPBV | 56321 | 1486 mmhg | 36482 | 82.3 C. | 95159 |
| Greenacre #5 | 34-2 | 4 May 2019 | 7:42:23 | 453 PPBV | 56321 | 1687 mmhg | 36482 | 84.4 C. | 95159 |
| Greenacre #5 | 34-3 | 4 May 2019 | 7:55:49 | 576 PPBV | 56321 | 1458 mmhg | 36482 | 79.3 C. | 95159 |
| ... | ... | ... | ... | ... | ... | ... | ... | ... | ... |
| Northbridge | G18 | 5 May 2019 | 14:44:37 | 565 PPBV | 56321 | 1785 mmhg | 36482 | 69.3 C. | 95159 |
| Northbridge | G19 | 5 May 2019 | 14:58:46 | 624 PPBV | 56321 | 1862 mmhg | 36482 | 67.6 C. | 95159 |
| Northbridge | D07 | 5 May 2019 | 15:02:14 | 658 PPBV | 56321 | 1732 mmhg | 36482 | 64.9 C. | 95159 |
| Northbridge | G09 | 5 May 2019 | 15:12:41 | 684 PPBV | 56321 | 1755 mmhg | 36482 | 62.1 C. | 95159 |
| Northbridge | S22 | 5 May 2019 | 15:17:56 | 695 PPBV | 56321 | 1698 mmhg | 36482 | 61.1 C. | 95159 |

The data of Table 1 can be transmitted from the portable gas analyzer device 14 to the external computing device 54 for long-term storage. The data of Table 1 can later be referenced to the data of Table 2, which shows model information, the manufacturer, calibration date, and the unique module ID of the sensor module 22.

TABLE 2

| CH4 Sensor Module ID | Date of Manufacture | Date of Calibration | Model |
|---|---|---|---|
| 56321 | 10 Jul. 2018 | 20 Sep. 2019 | GH825 |
| 47823 | 6 Apr. 2018 | 2 Dec. 2019 | Exto-ep |
| 95159 | 2 Jan. 2017 | 29 Jul. 2019 | 2654 |

As such, the data from Table 2 can help validate the integrity of the data from Table 1. It will be understood that a landfill operator may operate dozens of landfills each having hundreds of landfill wellheads, which must be measured multiple times a year over many years, by fleets of different sensors with different sensor biographies. The systems and methods described herein can allow the quick capture of relevant information for easy reference and data validation at a later date despite the myriad amount of data collected and sensors used.

Gas analyzer 14 provides significant advantages. Each sensor module 22 and/or transducer 58 includes a unique module ID that uniquely identifies that sensor module 22 and/or transducer 58 relative other sensor modules 22 and transducers 58. The unique module ID can include information regarding the module or provide a reference to access such information, such as the date of manufacture, identity of manufacturer, date of calibration, model type, etc. The unique module ID can be associated with parameter data generated by sensor module 22/transducer 58 to generated associated parameter data. The associated parameter data allows a user to access records and determine the integrity and accuracy of the data generated days, months, or years after the data was actually generated. Such tracking and association provide confidence in the data integrity and accuracy and can confirm the data integrity and accuracy at any time in the future.

FIG. 4 is a system block diagram of gas analyzer 14 showing internally mounted modules mounted in module banks 60a, 60b. Pneumatic pathway 62 is also shown. Multiple sensor modules 22 are shown mounted within housing 16 of gas analyzer 14. The multiple sensor modules 22 can be of differing or the same configuration. In the example shown, and as discussed in more detail below, the sensor modules 22 shown include infrared (IR) sensor module 84 and electrochemical (EC) sensor modules 92, 98, 104, 110. Bypass module 90 is also shown.

The block diagram includes user interface 18 (including upper keypads 34, lower keypads 36, display printed circuit board (PCB) 72, and display 38), ports 20, battery pack 26, analyzer controller 50, transmission circuitry 52, first module bank 60a (containing pressure module 74, pump assembly 80, solenoid valve 82, and IR sensor module 84), second module bank 60b (including bypass module 90 and EC modules 92, 98, 104, 110), baseboard 64, GPS module 66, battery sensor 68, and battery backup 70.

Pressure module 74 incudes programmable module circuitry 76 and transducer 78. IR module 84 includes programmable module circuitry 86 and transducer 88, EC module 92 includes programmable module circuitry 94 and transducer 96, EC module 98 includes programmable module circuitry 100 and transducer 102, EC module 104 includes programmable module circuitry 106 and transducer 108, and EC module 110 includes programmable module circuitry 112 and transducer 114. It is understood that each programmable module circuitry 76, 86, 94, 100, 106, 112 is substantially similar to programmable module circuitries 56a-56d (FIG. 3). It is similarly understood that each transducer 78, 88, 96, 102, 108, 114 is substantially similar to transducers 58a-58d (FIG. 3). Each of sensor modules 74, 84, 92, 98, 104, 110 can also be referred to as a "smart" module as each of those modules includes programmable module circuitry and a transducer.

Pneumatic circuit 60 extends through gas analyzer 14 from an inlet one of ports 20 to an outlet one of ports 20. It is understood that gas analyzer 14 can include multiple inlet ones of ports 20 and multiple outlet ones of ports 20. The flow direction of the pneumatic circuit 60 in the illustrated example is indicated by the arrows forming pneumatic circuit 60. Pneumatic circuit 60 extends through each of pressure module 74, pump assembly 80, solenoid valve 82, IR module 84, bypass module 90, and EC modules 92, 98, 104, 110 in series. In some examples, a first inlet port 20 is configured to provide gas to pressure module 74 to facilitate generation of pressure data and a second inlet port 20 is configured to provide gas to the remainder of pneumatic circuit 60 for serial flow through the modules. Each of pressure module 74, IR module 84, and EC modules 92, 98, 104, 110 are configured to generate data regarding one or more parameters of the gas flowing through pneumatic circuit 60. Pump assembly 80 is configured to pump the gas through pneumatic circuit 60 and each of modules 84, 90, 92, 98, 104, 110. Solenoid valve 82 functions as a gate to control gas flow downstream through solenoid valve 82 to the rest of the pneumatic circuit 60. Pump assembly 80 draws gasses into gas analyzer 14 and pumps the gasses through the pneumatic circuit 60.

Baseboard 64 is electrically connected with the other components shown in FIG. 4. Analyzer controller 50 is operatively connected to other components of gas analyzer 14 to control operation of the other components of gas analyzer 14. Analyzer controller 50 is configured to store software, implement functionality, and/or process instructions. Analyzer controller 50 can include memory 53 and control circuitry 51 configured to execute instructions stored on the memory. Analyzer controller 50 is configured to perform any of the functions discussed herein, including receiving an output from any sensor referenced herein, detecting any condition or event referenced herein, and controlling operation of any components referenced herein. Analyzer controller 50 can be of any suitable configuration for controlling operation of gas analyzer 14, gathering data, processing data, etc. Analyzer controller 50 can include hardware, firmware, and/or stored software, and analyzer controller 50 can be entirely or partially mounted on one or more boards. Analyzer controller 50 can be of any type suitable for operating in accordance with the techniques described herein. While analyzer controller 50 is illustrated as a single unit, it is understood that analyzer controller 50 can be disposed across one or more boards. In some examples, analyzer controller 50 can be implemented as a plurality of discrete circuitry subassemblies. In some examples, analyzer controller 50 can include and/or be formed by a system on module (SOM).

Baseboard 64 receives electrical power from battery pack 26 and distributes the electrical power to the other components shown in FIG. 4. Battery sensor 68 is associated with battery pack 26 and is configured to inform control circuitry 50 when battery pack 26 is going to be removed. Battery sensor 68 can also be referred to as a fitment sensor. Gas analyzer 14 must be shut down before battery pack 26 is removed to avoid data loss and corruption to various components of gas analyzer 14. Analyzer controller 50 is configured to initiate power off of gas analyzer 14 based on control circuitry 50 receiving the signal from battery sensor 68. Battery sensor 68 can be of any suitable configuration for alerting analyzer controller 50 of the imminent removal of battery pack 26 and allowing sufficient time for battery pack 26 to be removed. For example, battery sensor 68 can be a mechanical device that generates a signal when actuated by the user, the signal informing the analyzer controller 50 that battery pack 26 is going to be removed. In some examples, battery sensor 68 can be a threaded component that must be unthreaded from gas analyzer 14 prior to removal of battery pack 26 with the unthreading generating the signal, among other options. Battery backup 70 is an internal power source configured to provide sufficient power to gas analyzer 14 to allow gas analyzer 14 to properly power down in the event of unexpected power loss, such as due to battery 28 dying or being improperly removed. Battery backup 70 can provide minimal power to maintain date/time. In some examples, battery backup 70 can provide power to a sensor module.

Analyzer controller 50 is in data communication with user interface 18, including upper keypads 34, lower keypads 36, and display 38, through baseboard 64. Display PCB 72 can facilitate data communication between display 38 and analyzer controller 50. GPS module 66 is configured to generate location information regarding gas analyzer 14 and the location where gas samples are taken. The location information can be associated with the parameter data generated by sensor modules 74, 84, 92, 98, 104, 110.

Baseboard 64 provides an electrical interface for power control and to facilitate data communications between various components of gas analyzer 14. As discussed in more detail below, each of the internally mounted sensor modules 74, 84, 90, 92, 98, 104, 110 can be mounted at a docking station that provides mechanical, electrical, and pneumatic connections for that sensor module 74, 84, 90, 92, 98, 104, 110. The sensor modules 74, 84, 90, 92, 98, 104, 110 can be swapped between the various docking stations such that gas analyzer 14 can be configured in any manner desired by the user.

Each of pressure module 74, pump assembly 80, solenoid valve 82, IR module 84, bypass module 90, and EC modules 92, 98, 104, 110 are electrically connected to baseboard 64. Each of pressure module 74, pump assembly 80, IR module 84, and EC modules 92, 98, 104, 110 are electrically connected to baseboard 64 to bidirectionally communicate with analyzer controller 50. Unlike pressure module 74, IR module 84, and EC modules 92, 98, 104, 110, which are each configured to generate parameter data, bypass module 90 does not generate data regarding a parameter of the gas. Instead, bypass module 90 is configured to form a pass-through module that completes pneumatic circuit 60. Bypass module 90 is electrically connected to baseboard 64 to indicate the presence of bypass module 90 to analyzer controller 50. As discussed in more detail below, analyzer controller 50 can serially identify the various modules mounted within gas analyzer 14 and can determine whether pneumatic circuit 60 is closed. The presence of a bypass module 90 at a location along the pneumatic circuit 60 confirms to analyzer controller 50 that that location along the pneumatic circuit 60 is closed.

Analyzer controller 50 is in communication with module circuitries 76, 86, 94, 100, 106, 112 to provide data to and receive data from pressure module 74, IR module 84, and EC modules 92, 98, 104, 110. Analyzer controller 50 receives data outputs from each of pressure module 74, IR module 84, and EC modules 92, 98, 104, 110. Control circuitry 50 can communicate that data to the user via display 38 and/or communicate that data offboard via transmission circuitry 52. For example, transmission circuitry 52 can facilitate radio frequency (RF) communications and/or can facilitate communications over a network, such as a local area network, wide area network, and/or the Internet. In one example, transmission circuitry 52 can be configured for communication utilizing short-wavelength ultra high frequency (UHF) radio waves in the 2.4 GHz band (2.400-2.525 GHz) (e.g., Bluetooth® communications). In another example, the communications circuitry can be configured for communications utilizing super high frequency (SHF) radio waves in the 5 GHz band. In some examples, transmission circuitry 52 includes one or both of a Bluetooth chipset and a WiFi chipset.

Module circuitries 76, 86, 94, 100, 106, 112 are respectively disposed on one or more circuit boards within pressure module 74, IR module 84, and EC modules 92, 98, 104, 110. As such, the module circuitries 76, 86, 94, 100, 106, 112 are removable with modules 74, 84, 92, 98, 104, 110 and are placed in communication with analyzer controller 50 when the associated module 74, 84, 92, 98, 104, 110 is mounted within gas analyzer 14. Sensor modules 74, 84, 92, 98, 104, 110 respectively include transducers 78, 88, 96, 102, 108, 114 configured to generate data regarding a parameter of the gas. Sensor modules 74, 84, 92, 98, 104, 110 can provide the data generated by transducers 78, 88, 96, 102, 108, 114 to analyzer controller 50.

In some examples, gas analyzer 14 is configured such that analyzer controller 50 requests information from programmable module circuitry 76, 86, 94, 100, 106, 112 prior to the information being communicated to analyzer controller 50. In some examples, the programmable module circuitry 76, 86, 94, 100, 106, 112 is configured to provide data to analyzer controller 50 only in response to a request from analyzer controller 50. It is understood that the programmable module circuitry 76, 86, 94, 100, 106, 112 can be of any configuration suitable for generating data, analyzing data, storing data, communicating data, etc. For example, each programmable module circuitry 76, 86, 94, 100, 106, 112 can include one or more of a programmable integrated circuit, a microprocessor, a controller, a digital signal processor (DSP), an application specific integrated circuit (ASIC), a field-programmable gate array (FPGA), or other equivalent discrete or integrated logic circuitry. Each programmable module circuitry 76, 86, 94, 100, 106, 112 can further include amplifier circuitry for amplifying a signal generated by the transducer of its module.

Programmable module circuitries 76, 86, 94, 100, 106, 112 each include memory 59 that can be configured to store calibration data for its respective module 74, 84, 92, 98, 104, 110. The calibration data includes data that calibrates the sensor module for use. For example, information regarding the transducer of the module can be generated at the factory. A calibration factor specific to that transducer is generated and saved on the programmable module circuitry. The calibration factor is specific to that module and based on measurements taken from its transducer.

The data stored in the programmable module circuitry 76, 86, 94, 100, 106, 112 can further include information regarding the calibration status and/or history of that module, such as the date of the last calibration, the elapsed time since the last calibration, the period of operation since the last calibration, etc. Programmable module circuitry 76, 86, 94, 100, 106, 112 can be further configured to store characterization data for its respective module 74, 84, 92, 98, 104, 110. The characterization data can provide information regarding the nature of that module, such as the parameter that that module is configured to generate data for, etc. For example, programmable module circuitry 86 can store characterization data indicating that IR module 84 is an IR module. Programmable module circuitry 76, 86, 94, 100, 106, 112 receives signals from the transducer 78, 88, 96, 102, 108, 114 of its associated module, can perform mathematical functions to create a linearized output, and can communicate the output to analyzer controller 50. Analyzer controller 50 can store the information in its memory, provide the information to the user via display 38, and/or communicate the information via transmission circuitry 52.

In some examples, analyzer controller 50 can provide data generated by a first one of sensor modules 74, 84, 92, 98, 104, 110 to a second one of sensor modules 74, 84, 92, 98, 104, 110 to facilitate data generation by the second one of the sensor modules 74, 84, 92, 98, 104, 110. For example, IR module 84 can receive additional inputs, such as pressure data from pressure module 74, and can utilize that additional input to generate an output. In such an example, pressure module 74 can provide the pressure data to IR module 84 via baseboard 64 and analyzer controller 50.

Analyzer controller 50 is configured to determine the presence of and assign identifiers to each module present in gas analyzer 14 whenever gas analyzer 14 is powered on. The new identifier generated on power up can overwrite any previous identifier stored on the programmable module circuitry of that module. As such, modules can be swapped between various gas analyzers 14 without concern that identifiers will conflict between various ones of modules present in gas analyzer 14.

The communications line on baseboard 64 is shared by each of sensor modules 74, 84, 92, 98, 104, 110. During power up, analyzer controller 50 assigns each module mounted within gas analyzer 14 a unique communications identifier to allow analyzer controller 50 to communicate with each individual module. Analyzer controller 50 can individually power up and power down each module disposed within gas analyzer 14 during the identification process. On power up of gas analyzer 14, each module docking station is serially powered to determine if a module is present at that docking station and to assign each module a communications identifier.

If no response is received when the docking station is powered, then analyzer controller 50 can determine if a dummy module, such as bypass module 90, is present at that location. For example, analyzer controller 50 can identify the presence of dummy module based on the presence of a contact pad extending from the dummy module and contacting baseboard 64. In some examples, such as where a module spans multiple docking stations, analyzer controller 50 can determine that a module should not be present at a certain docking station based on the characterization data received from the programmable module circuitry of the module spanning the multiple docking stations. For example, the programmable module circuitry of that module can store information indicating the number of docking stations that that module is configured to span.

If no contact pad is present and there is no indication that that docking station should be bypassed, then analyzer controller 50 can determine that a module is not present at that location, which would indicate an opening in pneumatic circuit 60 through gas analyzer 14. In such an instance an alert can be provided to the user via user interface 18 that the opening in pneumatic pathway should be closed, such as by inserting a bypass module 90 at that location.

If a response is received from a module at the docking station, then a unique communications identifier is assigned to the module located at that docking station and the module stores that communications identifier in its programmable module circuitry. The communications identifier is utilized by control circuitry 50 to identify which module a communication is intended for. Each module can be configured to respond only to those communications including its communications identifier. Each module can further associate data generated by its transducer with its communications identifier to indicate to analyzer controller 50 the module that that data was generated by. In some examples, the communications identifier can be the unique module ID associated with that module, as discussed in more detail above with reference to FIG. 3 above. In some examples, analyzer controller 50 generates the communications identifier independent of other identifiers. The communications identifier can be of any form suitable for uniquely identifying each module to facilitate communications between analyzer controller 50 and that module. After the unique communications identifier is assigned to the module, that docking station is powered down and the next docking station in series is powered to determine if a module is located at that docking station. The process is repeated serially for each docking station in gas analyzer 14.

Gas analyzer 14 is configured to determine the presence of and assign communications identifiers to each module present in gas analyzer 14 every time gas analyzer 14 is powered cycled. The communications identifier generated on power up overwrites any previous identifier stored on the programmable module circuitry of that module. As such, modules can be swapped between various gas analyzers 14 without concern that communications identifiers will conflict between various ones of modules present in gas analyzer 14.

Gas analyzer 14 provides significant advantages. Gas analyzer 14 is modular in that various ones of modules 62, 80, 92, 98, 104, 110 can be located at various locations within gas analyzer 14 and can be mixed and matched depending on the particular requirements of the job. In addition, calibration data is carried on the programmable module circuitry of each module such that the user can simply swap a calibrated module for a different module without having to send in the entire gas analyzer 14 to the manufacturer for calibration, saving time and costs. Such modularity further supports upgrading gas analyzer 14 in the field with new features, such as the ability to sense different gases or different ranges of gasses or different parameters of the gasses. With each module carrying its own calibration information on its own programmable module circuitry, the modules can be plugged into any docking station in gas analyzer 14 and can be swapped across multiple ones of gas analyzers 14 and will still be properly calibrated and operable. In addition, providing unique communications identifies upon power up provides accurate data management and tracking even where modules are swapped in the field. After swapping modules, gas analyzer 14 is repowered and new communications identifiers are provided to the modules in gas analyzer 14, facilitating module tracking and data management.

Figure 5:
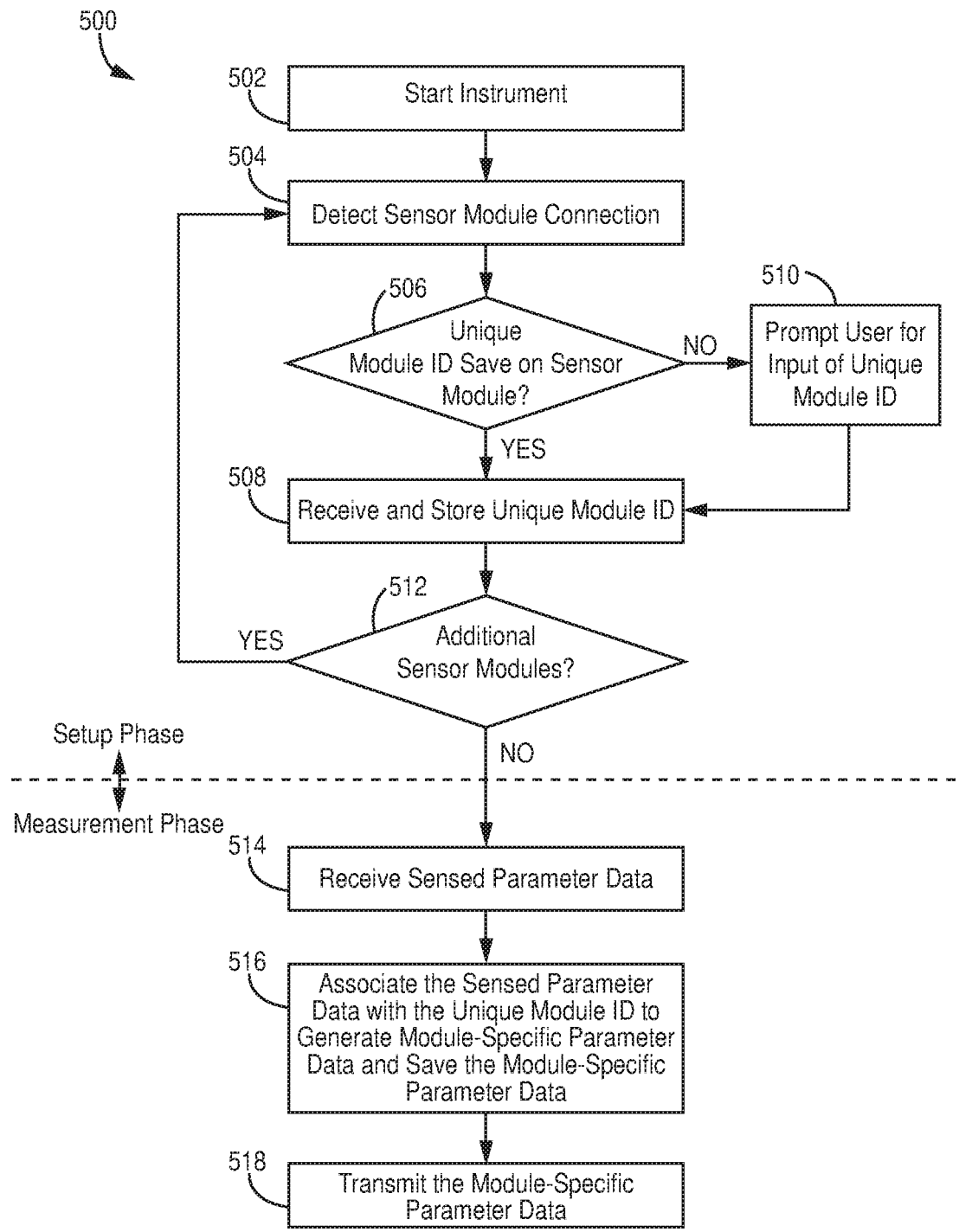
FIG. 5 is a flowchart illustrating a method of managing and tracking data generated by a gas analyzer.

FIG. 5 is a flowchart illustrating method 500 of managing a device, such as a portable gas analyzer, such as gas analyzer 14. Method 500 can be utilized for tracking data generated by a gas analyzer for use on a landfill site, such as landfill site 10 (FIG. 1), or in another environment, such as for use in IVF. Method 500 includes a setup phase, including steps 502-512, and a measurement phase, including steps 514-518. The setup phase includes locating and identifying each module associated with the gas analyzer and receiving a unique module ID for each module of the gas analyzer. The measurement phase includes generating data with the modules of the gas analyzer and associating the data from each module with the unique module ID for that module. The setup and measurement phases are discussed in more detail below.

At step 502, the instrument is started, which can include powering the gas analyzer, pressing a start or "on" button, or booting the analyzer controller of the gas analyzer, such as by booting analyzer controller 50 (FIGS. 3 and 4). At step 504, sensor modules, such as sensor modules 22 (FIGS. 3 and 4), of the instrument are detected. In step 504, the analyzer controller can determine whether a module is present at a module mounting location of the gas analyzer. For example, the analyzer controller can monitor whether open or closed circuits (e.g., by resistance or impedance checks between contacts) are present in a sensor port, in slots for sensor modules, in docking stations, or other connection feature. In some examples, open circuits indicate the lack of a connection, whereas closed circuits indicate the presence of a connected sensor module. In some examples, the analyzer controller can serially power each mounting location to determine whether a sensor module is present at each mounting location. The analyzer controller can determine whether a module is present based on a signal received from that mounting location. In some examples, the analyzer controller can identify remotely connected devices, similar to sensor module 22c (FIG. 3), via a wireless connection with that device.

When a sensor module is detected in step 504, method 500 moves to step 506 and the analyzer controller determines whether a unique module ID is saved on the sensor module identified in step 504. The unique module ID can include information such as the manufacturer name and serial number for that sensor module and/or for each transducer of the sensor module. When the sensor module is detected, the analyzer controller can send a request to the sensor module inquiring as to the unique module ID of that sensor module. In response, the sensor module can send an answer back to the analyzer controller confirming whether it has a stored unique module ID and/or providing the unique module ID of that sensor module. If the sensor module does have a unique module ID stored in its memory, then the analyzer controller can send a request for the unique module ID to the sensor module if the sensor module did not directly reply to the inquiry regarding the presence of a unique module ID by sending its unique module ID. When the analyzer controller detects that an accessory is connected, with a cable or via a wireless connection, the analyzer controller can determine if it is possible to obtain the unique module ID from that remote accessory. The control circuitry can determine if it can obtain the unique module ID from the remote accessory based on one or more of the type of connection and communication commands. In some examples, if the unique module ID can be read, then the analyzer controller will read it automatically. For example, the control circuitry can wirelessly communicate with the remote accessory to obtain the unique module ID of that remote accessory. In some cases, the sensor module can automatically send its unique module ID to the analyzer controller without being specifically prompted by the analyzer controller to send the unique module ID. For example, the sensor module can be configured to send its unique module ID to the analyzer controller upon the sensor module making an electrical connection with the analyzer controller.

Where the sensor module does have a stored unique module ID, then the answer to step 506 is YES and method 500 advances to step 508. If, however, the sensor module does not have a unique module ID saved in the memory of that sensor module, or if the sensor module is not digital or otherwise does not respond to the request, then the answer to step 506 is NO and method 500 advances to step 510.

In step 510, the control circuitry generates and provides a prompt to the user. The prompt requests the unique module ID of the sensor module. Step 510 can be performed when data from the sensor module is required, such as during operation of the gas analyzer, or at any time before utilizing that sensor module to generate parameter data. For example, the analyzer controller can provide an audio and/or visual prompt via the user interface of the gas analyzer, such as user interface 18 (FIGS. 1, 2A, 3, 4). In some examples, the analyzer controller can provide the prompt to a remote computing device, such as remote computing device 30 (FIG. 3). For example, the analyzer controller can provide the prompt to the remote computing device via transmission circuitry, such as transmission circuitry 52 (FIGS. 3 and 4).

The prompt can direct the user to input the manufacturer name, serial number, and/or other identifying information forming a unique module ID for that sensor module. The user can input the unique module ID to the analyzer controller via the user interface and/or the remote computing device. In some examples, a barcode reader, which can be built into the gas analyzer, can be used to scan a barcode of the sensor module. In some examples, an optical reader, such as a camera, and which can be built into the gas analyzer or communicatively connected to the gas analyzer, can be utilized to photograph the serial number of the sensor module. The analyzer controller can perform optical character recognition on the image to decode the image to text and numbers which form the unique module ID. In some examples, the analyzer controller can generate and store a list of the most-recently manually entered modules and unique module IDs. The analyzer controller can recall the list and display the list to the user, such as via the user interface. The user can select the appropriate module from that list if the module appears on the list. Such a list facilitates quick setup where the same module remains in use over a period of time. The analyzer controller receives the unique module ID in step 510 and method 500 then proceeds to step 508.

In step 508, whether reached directly from step 506 or via step 510, the control circuitry stores the unique module ID in its memory as the unique module ID of that sensor module. The unique module ID is thereby associated with that sensor module such that the analyzer controller can further associate the unique module ID with parameter data received from that sensor module.

In step 512, the analyzer controller determines if there are additional sensor modules associated with the gas analyzer. The portable gas analyzer device can have multiple possible connections with multiple sensor modules, such as connecting two, three, four, five, or more sensor modules with a single portable gas analyzer device. The analyzer controller of the portable gas analyzer device can scan each of multiple channels (e.g., open circuits in case of hard wire, wireless connectivity in case of wireless connections) to identify each sensor module connected to the gas analyzer device. The control circuitry can populate a list of connected sensor modules based on the sensor modules detected during the setup phase.

If the answer in step 512 is YES, such that the analyzer controller detects additional sensor modules, then method 500 proceeds back to step 504 and repeats steps 504, 506, 508, and 510 for each additional sensor module. The analyzer controller continues to repeat steps 504-512 until each sensor module is associated with its unique module ID. When each sensor module has been identified such that there are no additional sensor modules, then the answer in step 512 is NO and the setup phase is complete.

The setup phase can be performed according to a variety of steps and protocols, without limitation to those specifically discussed. The analyzer controller can store the sensor modules and unique module IDs in a memory of the analyzer controller for later use. For example, the analyzer controller can store manually inputted information regarding various modules in its memory. In some examples, the control circuitry can store the accessory type, manufacturer name, serial number, and other identifying information forming the unique module ID for each sensor module until the gas analyzer is power cycled or the information is re-inputted by the user. In some examples, the analyzer controller can provide the user with the option to make the requirement to input and/or store the identifying information optional or mandatory. This configuration setting can be stored in a memory of the analyzer controller. In some examples, the analyzer controller can generate and store a list of the most-recently connected sensor modules, such as the last five, ten, fifteen, etc., that have been connected to the gas analyzer. In some examples, the analyzer controller can display information to the user regarding each of the sensor modules associated with the gas analyzer and in use. The list can be displayed at the end of, or throughout, the setup phase and prior to, or throughout, the measurement phase. For example, the analyzer controller can display a table of each sensor module and its associated unique module ID. Such a list allows the user to confirm that the gas analyzer is configured to generate the data that the user wants to generate.

After completing the setup phase, the gas analyzer is ready for operation and method 500 proceeds to the measurement phase. In the measurement phase, the gas analyzer is operated to generate data regarding a gas. In step 514, the sensor modules generate parameter data and the analyzer controller receives the parameter data from the sensor modules. Concurrently and/or subsequently to step 514, step 516 is performed in which the analyzer controller associates the parameter data with the unique module ID of the sensor module/transducer of the sensor module that generated the parameter data. The data generated by associating the parameter data with the unique module ID can also be referred to as associated parameter data. The associated parameter data can be saved by the analyzer controller. As discussed herein, other data can also be associated with the parameter data by the analyzer controller, such as locational information, such as the site or specific wellhead, and temporal information. The data generated by associating the locational information and/or temporal information with the parameter data or associated parameter data can be referred to as sample-specific parameter data.

Steps 514 and 516 can be repeated throughout operation of the gas analyzer as additional parameter data is generated by the sensor modules. The process of receiving the parameter data, associating the parameter data with the unique module ID to generate associated parameter data, and saving that associated parameter data can be repeated in a loop until the session is complete (e.g., sampling at the particular landfill wellhead 12 is complete, sampling is complete at all landfill wellheads 12 at the landfill site 10, etc.). Concurrently with step 516, or at a later time, step 518 can be performed. In step 518 the associated parameter data is transmitted offboard for data use and storage, such as to a remote computing device.

Method 500 provides significant advantages. The control circuitry receiving and storing a unique module ID for each sensor module and/or transducer provides discrete tracking information for the parameter data generated. The unique module ID can include information regarding the module or provide a reference to access such information, such as the date of manufacture, identity of manufacturer, date of calibration, model type, etc. The unique module ID is associated with the parameter data such that the exact identity of the sensor module and/or transducer that generated the parameter data is known. Knowing the identity of the sensor module and/or transducer that generated the parameter data allows a user to access records and determine the integrity and accuracy of the data that was generated days, months, or years after the data was actually generated. Such tracking and association provide confidence in the data integrity and accuracy and can confirm the data integrity and accuracy at any time in the future.

Figure 6:
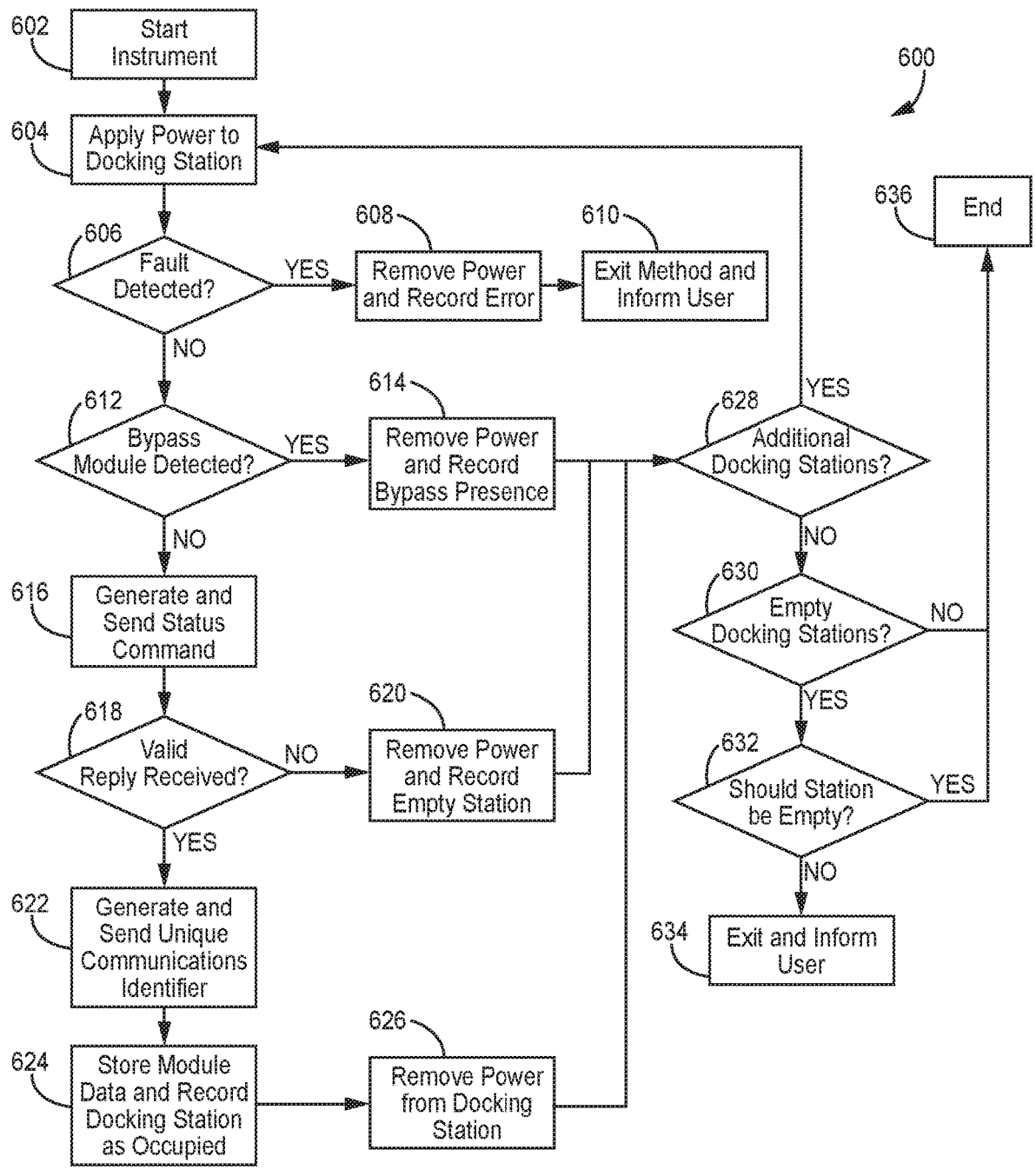
FIG. 6 is a flowchart illustrating a method of configuring a gas analyzer.

FIG. 6 is a flowchart illustrating method 600 of identifying modules on power up. Method 600 can be utilized to facilitate tracking data and module management during operation. Method 600 can be utilized for data tracking and management for data generated by a gas analyzer, such as gas analyzer 14. Method 600 can be utilized in any desired environment associated with generating parameter data regarding gasses, such as a landfill environment, such as landfill site 10 (FIG. 1), or during IVF. Method 600 can be performed simultaneously with or separately from method 500 (FIG. 5). Method 600 can be performed as part of the setup phase shown in FIG. 5. The communications line on baseboard 64 is shared by each of smart modules 22 and bypass modules 90. The analyzer controller, such as analyzer controller 50 (FIGS. 3 and 4) can determine whether modules are located at each docking station within the gas analyzer. The analyzer controller can assign each smart module mounted within gas analyzer 14 a unique identifier to facilitate communications between the analyzer controller and each individual module. Gas analyzer 14 can individually power up and power down each module disposed within gas analyzer 14. On power up of gas analyzer 14, each module docking station is serially powered and analyzer controller determines if a module is present at that docking station and can assign each module an identifier.

In step 602, the instrument is started, which can include powering the gas analyzer, pressing a start or "on" button, or booting the analyzer controller of the gas analyzer, such as by booting analyzer controller 50 (FIGS. 3 and 4). In step 604, power is applied to a first docking station of the gas analyzer. At step 606 the analyzer controller determines if a fault is present. For example, a fault signal can be generated when power is supplied to the first docking station. The fault can indicate some error with the communications line or the module at the docking station, such as if the sensor module is corrupted. If a fault is detected, then method 600 proceeds to step 608. In step 608, the power is removed from the docking station and the error is recorded, such as in a memory of the analyzer controller. The analyzer controller can additionally or alternatively transmit the error message to a remote computing device, such as remote computing device 30 (FIG. 3). Method 600 can then proceed to step 610, during which the analyzer controller can exit method 600 and can further generate an error message and inform the user of the fault, such as via user interface 18 (FIGS. 1, 2A, 3, 4).

If no fault is detected, then the answer in step 606 is NO and method 600 proceeds to step 612. In step 612, the analyzer controller determines whether a dummy module, such as bypass module 90, is present at the powered docking station. For example, the analyzer controller can identify the presence of the bypass module based on the presence of a contact pad extending from the bypass module and contacting the baseboard of the gas analyzer. The contact pad can close an electrical circuit, thereby indicating the presence of a module at the docking station. In some examples, the analyzer controller can send a command to the docking station and can determine that the module mounted at the docking station is a bypass module based on the closed circuit and no response being received from the module at the docking station. In some examples, the presence of the closed circuit generates a signal indicative of a bypass module being located at the docking station. If a bypass module is present at the docking station, then method proceeds to step 614. In step 614, the analyzer controller records the presence of a bypass module at that docking station. As such, the analyzer controller knows that the module mounted at the docking station is not configured to generate parameter data. From step 614, method 600 can proceed to step 628.

If the answer to step 612 is NO, then method proceeds to step 616. In step 616, a status command is generated by the analyzer controller and sent to the docking station. The analyzer controller awaits a reply from the docking station. For example, the analyzer controller can wait a set period of time to receive the reply. The status command is configured to cause a module present at the docking station to provide a response to analyzer controller 50. The response can include data regarding that smart module, such as characterization data and, in some examples, a unique module ID. The characterization data can include information regarding the sensor module, such as the type of parameter that the sensor module is configured to generate data for, configuration data for the sensor module, the number of docking stations associated with the module, etc.

In step 618, the analyzer controller determines whether a valid reply has been received in response to the status command generated and provided in step 616. If the answer to step 618 is NO, such that a valid reply was not received, then method 600 proceeds to step 620. In step 620, power is removed from the docking station and analyzer controller 50 records the docking station as being unoccupied. Method 600 then proceeds to step 628.

If a valid reply is received at step 618, then method proceeds to step 622. The valid reply indicates that a sensor module is mounted at the docking station. In step 622, the analyzer controller generates a unique communications identifier for the sensor module mounted at the docking station. The unique communications identifier can also be referred to as a unique address and is associated only with the module at that docking station and facilitates communications between the analyzer controller and the programmable module circuitry of the sensor module. The unique communications identifier can be provided to the module mounted at the docking station and stored in a memory of that module. The unique communications identifier can overwrite any previous communications identifier stored in the memory of the module. Overwriting any previous communications identifier ensures that communications identifiers will not conflict between modules, thereby allowing modules to be freely swapped between gas analyzers. During operation of the gas analyzer, the analyzer controller can label commands intended for the sensor module with the unique communications identifier. The sensor module can be configured to respond only to those commands labeled with its unique communications identifier. The sensor module can be further configured to label data generated by the sensor module with the unique communications identifier to identify that data as having been generated by the sensor module.

In step 624, the analyzer controller determines the type of module mounted at the docking station, which can be based on the reply received in step 618 or based on additional information provided by the sensor module in response to commands from the analyzer controller. The module type and any additional information regarding the sensor module can be stored in the memory of the analyzer controller. The analyzer controller can further record that the docking station is occupied by an active sensor module. As such, the docking station is associated with the particular sensor module mounted at the docking station. The analyzer controller thereby knows that a sensor module is mounted at that docking station and can provide commands to the sensor module based on the known location and the unique communications identifier. The analyzer controller thereby records the module type located at that docking station and further records the docking station as including an active module. It is understood that step 624 can be performed prior to, simultaneously with, or subsequent to step 622. In step 626 power is removed from the docking station. From step 626, method 600 proceeds to step 628.

In step 628, whether reached from step 614, step 620, or step 626, the analyzer controller determines if there are additional docking stations that have not been powered and identified. The analyzer controller can serially identify each of the docking stations associated with the gas analyzer. In some examples, the analyzer controller is configured to serially identify each docking station and associated module. The control circuitry knows the number of docking stations associated with the gas analyzer. If there are additional docking stations in gas analyzer, then method 600 proceeds back to step 604 and the analyzer controller performs steps 604-626, as appropriate, for the next docking station. Method 600 continues to loop though the appropriate ones of steps 604-626 until the answer at step 628 is NO, indicating that there are no additional docking stations. If the answer to step 628 is NO, then method proceeds to step 630.

In step 630, the analyzer controller determines if any docking stations were recorded as being empty in step 620. As discussed above, the status of a docking station as being empty can be recorded in the memory of the analyzer controller. The analyzer controller can determine whether any docking stations are empty based on that stored status. If the answer in step 630 is NO, then method 600 proceeds to step 636 and the configuration and setup is complete. If the answer in step 630 is YES, then method proceeds to step 632.

In step 632, the analyzer controller determines whether the empty docking station should be empty. In some examples, the analyzer controller can determine whether the docking station should be empty based on the type of module mounted at an adjacent docking station. For example, IR modules, such as IR modules 84, can occupy multiple docking stations and can span across docking stations without occupying those docking stations, as discussed in more detail below. The characterization data from the programmable module circuitry of an IR module can indicate the length of the module and the number of unoccupied docking stations spanned by the module. If the analyzer controller determines that the unoccupied docking station should be occupied, then the answer in step 632 is NO and method 600 proceeds to step 634. An unoccupied docking station that should be occupied creates an opening in the pneumatic pathway through the gas analyzer that must be closed to facilitate serial gas flow through the gas analyzer. If the analyzer controller determines that the unoccupied docking station should be unoccupied, then the answer in step 632 is YES and method 600 proceeds to step 636.

In step 634, the analyzer controller can generate and transmit an error message to the user, such as via the user interface of the gas analyzer or the remote computing device. The error can also be recorded, such as in a memory of the analyzer controller. The error message to the user can indicate that the docking station is unoccupied and can further instruct the user to remedy the situation. For example, the user can install a bypass module at the unoccupied docking station.

If the analyzer controller determines that the unoccupied docking station should be unoccupied in step 632, then method 600 proceeds to step 636 and the configuration and setup is complete. In some examples, the analyzer controller can generate and send a message to the user that the configuration and setup has been successfully completed. The gas analyzer is thus ready for use.

Method 600 provides significant advantages. Method 600 provides user confidence as the analyzer controller will identify any openings in the pneumatic pathway prior to operation, preventing gasses from inadvertently leaking into the gas analyzer. Method 600 provides communications addresses for each module installed within the gas analyzer, facilitating the modular nature of the gas analyzer. Method 600 can be performed every time that the gas analyzer is power cycled. The communications identifiers generated on power up overwrite any previous identifier stored on the programmable module circuitry of that module. As such, modules can be swapped between various gas analyzers without concern that communications identifiers will conflict between various ones of modules present in the gas analyzer. After swapping modules, the gas analyzer is repowered and new communications identifiers are provided to the modules in gas analyzer, facilitating module tracking and data management. Method 600 thereby facilitates swapping of modules and the use of different modules within the same gas analyzer. Method 600 also allows the various modules to be installed at any desired docking station within the gas analyzer, allowing the user to configure the gas analyzer in any desired manner.

Figure 7A:
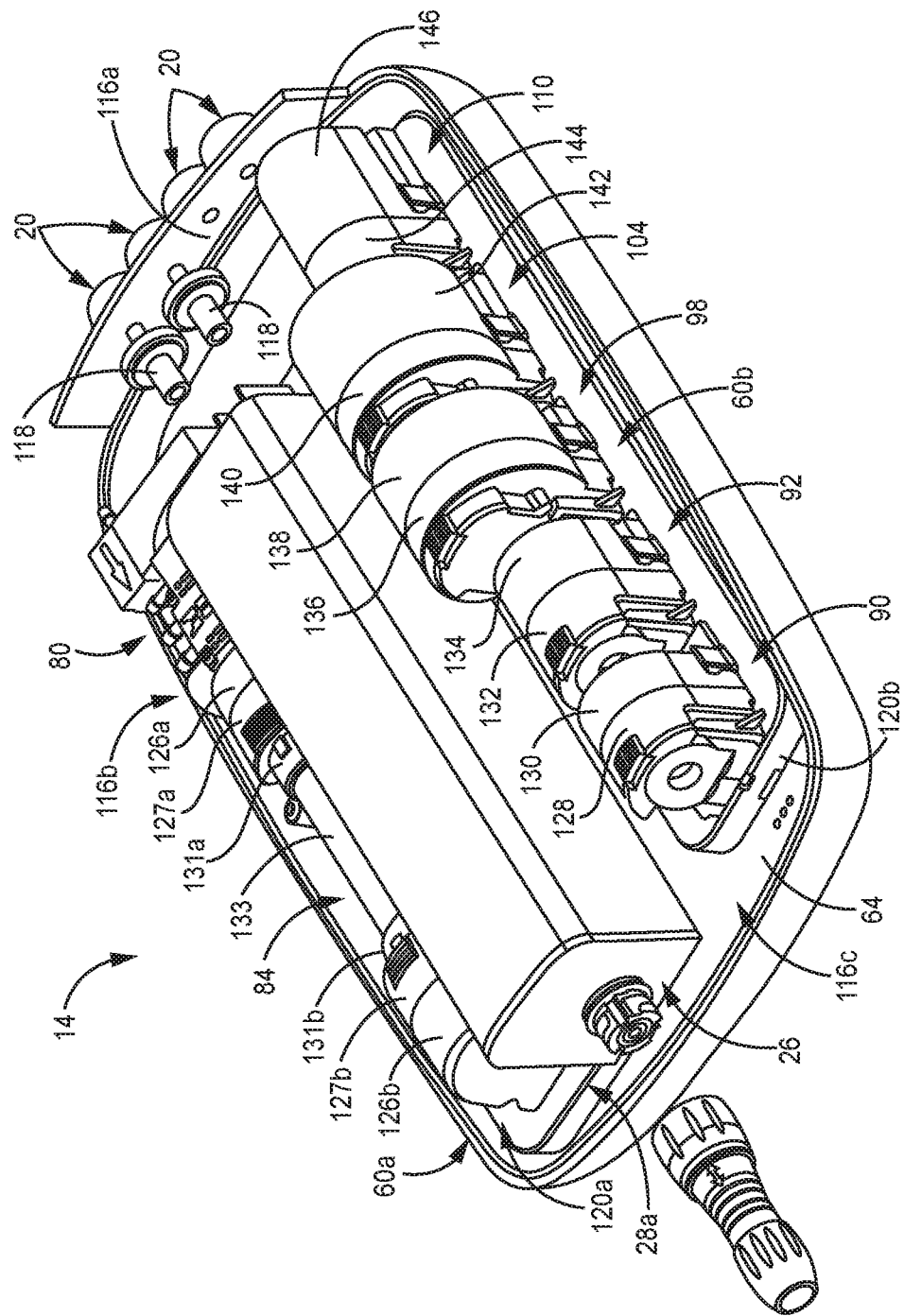
FIG. 7A is an isometric view of the backside of the modular hand-portable gas analyzer with the case back of the gas analyzer transparent to show components within the battery pack and components within the sensor compartment of the gas analyzer.
Figure 7B:
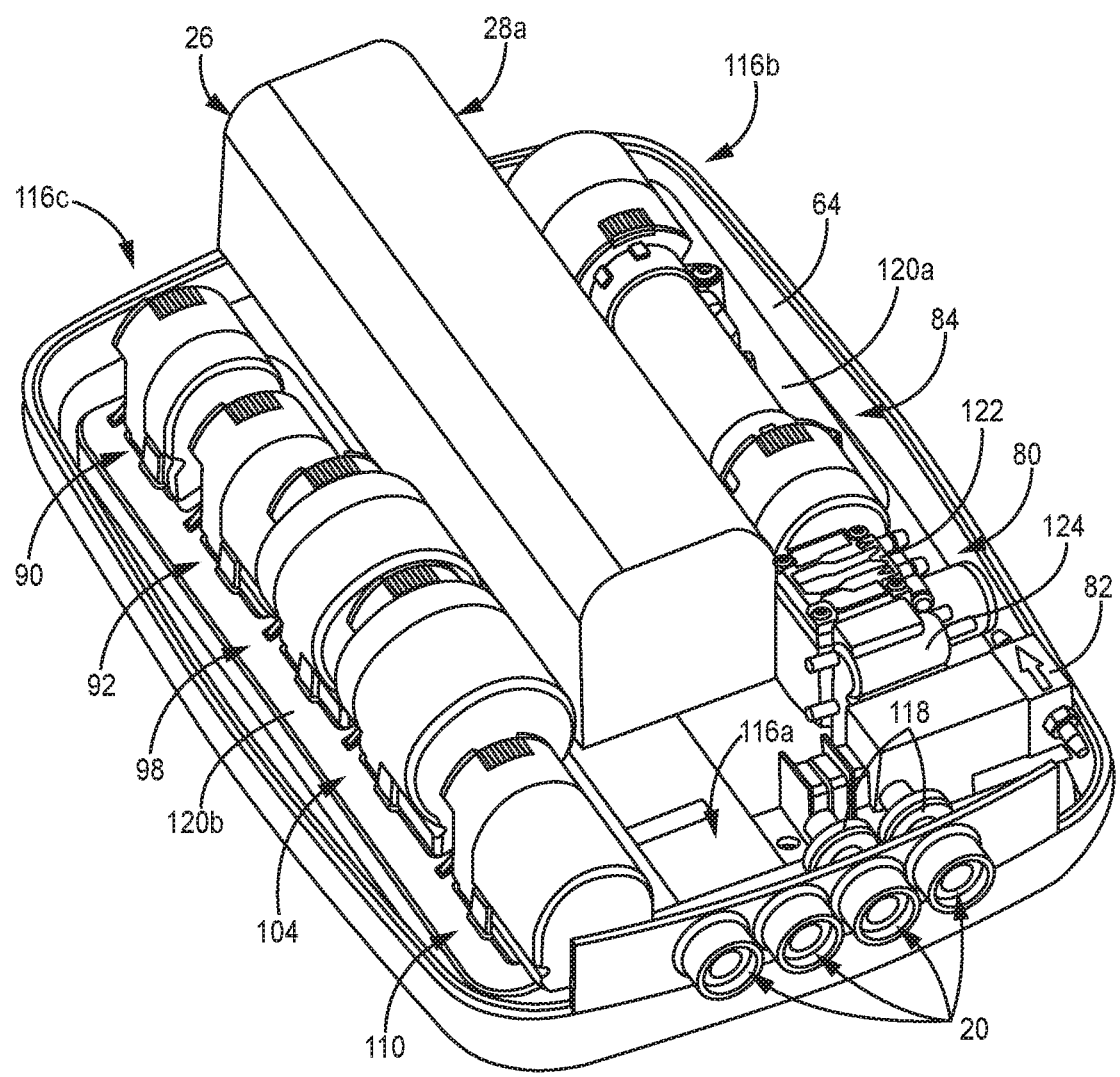
FIG. 7B is a view of the gas analyzer with the case back transparent, shown from a different perspective than FIG. 7A.
Figure 7C:
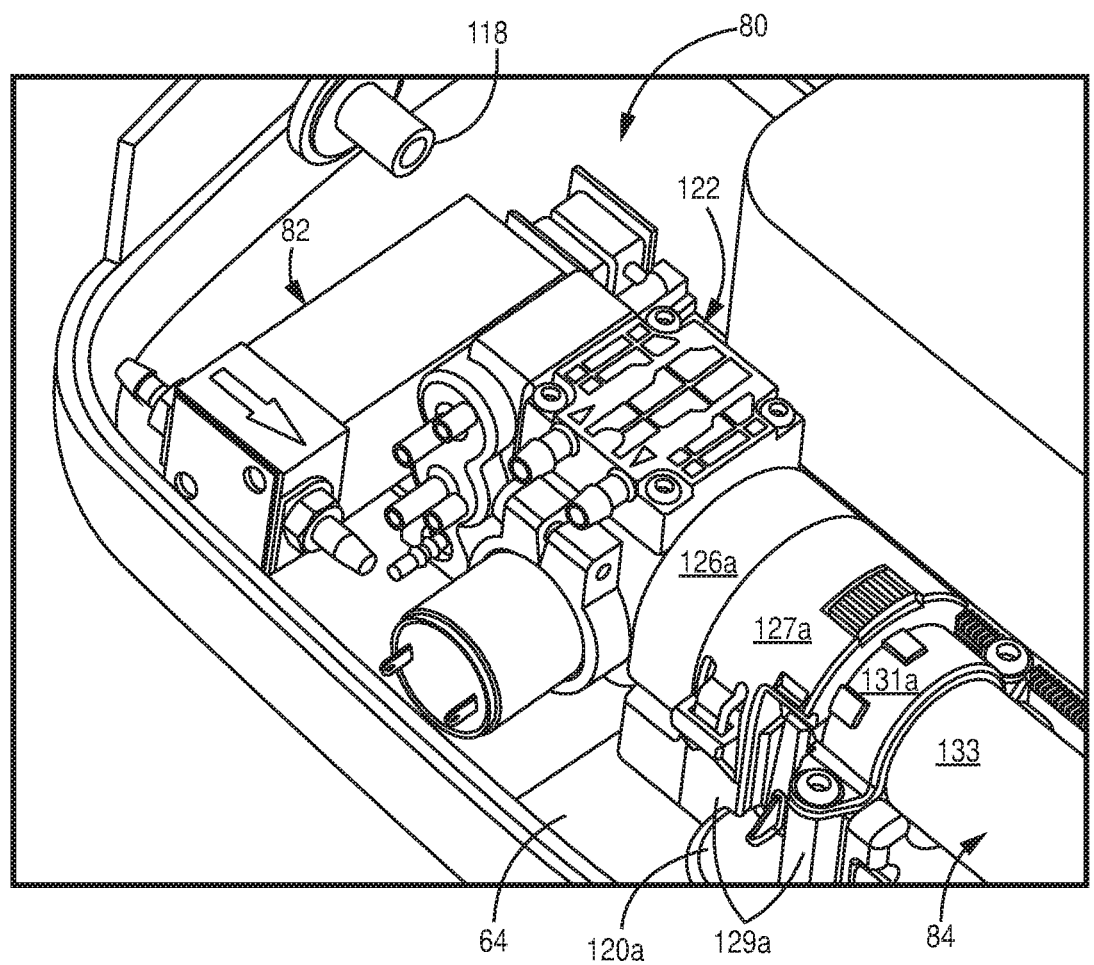
FIG. 7C shows a gas pump assembly of the gas analyzer of FIGS. 7A and 7B, with the rear case back transparent.

FIGS. 7A and 7B show views of gas analyzer 14 with case back shown as transparent, so that the components within sensor compartment 116 can be seen. FIG. 7C is an enlarged view of pump assembly 50 and a portion of IR module 84. FIGS. 7A-7C are discussed together. Because battery pack slot 28a is located centrally, compartment 116 is U-shaped about battery pack slot 28a. It is understood that compartment can be of any desired configuration for facilitating mounting of sensor modules 22 in banks 60a, 60b on opposite lateral sides of battery pack slot 28a. In the example shown, compartment 116 defines intake/exhaust compartment 116a, first sensor compartment 116b (housing sensor bank 60a), and second sensor compartment 116c (housing second sensor bank 60b). First and second sensor compartments 116b, 116c are positioned on opposite lateral sides of battery pack slot 28a and battery pack 26.

Intake/exhaust compartment 116a is associated with ports 20. contains filters 118 which protect against water ingress during sampling. Ports 20 are shown at a top longitudinal end of gas analyzer 14. Filters 118 are mounted to ports 24 and protect against contaminant ingress during sampling, such as water and particulates. Each port 20 can be either of an intake or an exhaust port. In some examples, gas analyzer 14 includes four ports 20. In some examples, a first one of ports 20 can be an intake port for the gas to provide the gas to the pneumatic circuit 60 (FIG. 4), a second one of ports 20 can be an exhaust port for the gas from the pneumatic circuit 60. Additional ones of the ports 20 can be associated with other sensor modules, such as those external to gas analyzer 14, such as sensor module 22c (FIG. 3).

Gas analyzer 14 includes module carrier frames 120a, 120b on which the various sensor modules are mounted. The module carrier frames 120a, 120b facilitate mechanical, electrical, and pneumatic connections for each of the sensor modules mounted within gas analyzer 14. While gas analyzer 14 is shown as including two module carrier frames 120a, 120b in the example shown, it is understood that gas analyzer 14 can include as many or as few module carrier frames 120a, 120b as desired, such as one, two, three, four, or more. The various module carrier frames 120a, 120b can be disposed in the various sensor compartments 116a-116c. Sensor compartments 116a, 116b, 116c may not be isolated relative one another, though in some examples one or more of the compartments 116a, 116b, 116c can be isolated from other compartments, such as by a physical barrier, an air-tight barrier, or any other desired barrier.

Each module carrier frame 120a, 120b includes one or more docking stations at which modules can mount. Each docking station can be configured to receive and mount one or more modules of differing configurations. As such, various modules of varying configurations can be mounted to the docking stations to facilitate generating data regarding a variety of parameters. The modules can be swapped to alter the configuration of gas analyzer 14. Each docking station is configured to facilitate a pneumatic connection to the pneumatic circuit 60, a mechanical connection between the module mounted at that docking station and the carrier frame 120a, 120b, and an electrical connection between the module and baseboard 64.

In the example shown, first sensor compartment 116b contains pump assembly 80 (having pump 122 and pump expansion chamber 124) and solenoid valve 82. First sensor compartment 116b further contains first module bank 60a. In the example shown, module carrier frame 120a is disposed in first sensor compartment 116b. IR module 84 is mounted on first module carrier frame 120a. It is understood, however, that any one of modules 84, 90, 92, 98, 104, 110 can be mounted on first module carrier frame 120a. IR module 84 can also be referred to as a "smart" module as IR module 84 includes sensing components (e.g., transducer 88 (FIG. 4)) and programmable module circuitry 86 (FIG. 4). First module carrier frame 120a is mounted on baseboard 64. In the example shown, first module carrier frame 120a has three sensor module docking stations, as discussed in more detail below. It is understood, however, that first module carrier frame 120a can include more or fewer than three sensor module docking stations, such as one, two, four, five, or more.

In the example shown, IR module 84 includes cap 126a, first housing 127a, body 129a, U-clip 131a, gas tube 133, U-clip 131b, body 129b (FIGS. 11A-11C), second housing 128b, and cap 126b. In the example shown, module cap 126a and first housing 129a are disposed at least partially outside of module carrier frame 120a and body 129a spans over a part of module carrier frame 120a into the first docking station. Gas tube 133 bridges the second docking station such that no pneumatic connection is made with the second docking station by IR module 84. Body 129b is partially disposed in an aperture of the second docking station and partially disposed in an aperture of the third docking station. Body 129b is pneumatically connected to the pneumatic ports of the third docking station. Second housing 128b and module cap 126b are disposed in the third docking station. It is understood that various IR sensor modules can have various configurations such that the IR sensor modules can span one, two, three, four, or more docking stations, as discussed in more detail below with reference to FIGS. 11A-12C.

Second sensor compartment 116c contains second module bank 60b, including second module carrier frame 120b and the modules mounted on second module carrier frame 120b. In the example shown, bypass module 90 and EC modules 92, 98, 104, 110 are shown as mounted to second module carrier frame 120b. It is understood that any desired configuration of modules can be mounted to second module carrier frame 120b, including IR module 84. Bypass module 90 includes module body 128 and cap 130 that together form a housing of bypass module 90. EC module 92 include includes module body 132 and cap 134 that together form a housing of EC module 92. EC module 98 include includes module body 136 and cap 138 that together form a housing of EC module 98. EC module 104 include includes module body 140 and cap 142 that together form a housing of EC module 104. EC module 110 include includes module body 144 and cap 146 that together form a housing of EC module 110.

Second module carrier frame 120b is mounted to baseboard 38 and has five sensor module docking stations in the example shown. It is understood that second module carrier frame 120b can include fewer or more than five docking stations, such as one, two, three, four, six, or more docking stations. In this embodiment, one module docking station is occupied by bypass module 90, which does not function as a sensor but is instead a "dummy" module that completes the pneumatic circuit. Bypass module 90 facilitates serial gas flow through the pneumatic circuit by closing the pneumatic circuit at the docking station that bypass module 90 is mounted at. Bypass module 90 can also form an electrical connection with baseboard 64. The electrical connection can indicate the presence of the bypass module 90 to control circuitry 50 (FIGS. 3 and 4). The gasses flowing through the pneumatic circuit pass through bypass module 90 without bypass module 90 generating data regarding the gasses. The other docking stations of in second sensor bank 60b are occupied by EC sensor modules 92, 98, 104, 110, which can also be referred to as "smart" modules. As discussed above with reference to FIG. 4, EC sensor modules 92, 98, 104, 110 respectively include transducers 96, 102, 108, 114 and programmable module circuitry 94, 100, 106, 112.

While IR module 84 is shown as mounted on first module carrier frame 120a within first sensor compartment 116b, it is understood that IR module 84 can be mounted on second module carrier frame 120b such that IR module 84 is disposed in second sensor compartment 116c. Similarly, bypass module 90 and EC sensor modules 92, 98, 104, 110 can be mounted on first module carrier frame 120a such that one or more of those modules are disposed in first sensor compartment 116b. First and second module carrier frames 120a, 120b facilitate mounting of the various modules 84, 90, 92, 98, 104, 110 at any desired location within gas analyzer 14. The modules can be mixed and matched and mounted at various locations to provide the desired arrangement. For example, IR module 84 and two of modules 90, 92, 98, 104, 110 can be mounted on second module carrier frame 120b while the other three of modules 90, 92, 98, 104, 110 can be mounted on first module carrier frame 120a. The modular mounting arrangement allows gas analyzer 14 to be configured in any desired manner to generate data regarding any one or more desired parameters. For examples, where only the parameter sensed by EC module 92 is desired, EC module 92 can be mounted at any desired docking station and bypass modules 90 can be mounted at all other docking stations.

During operation of gas analyzer 14, gas samples are drawn into sensor compartment 116a through an intake one of ports 20 and filter 118 by pump 122 of pump assembly 80. The gas samples flow along a gas flow path that includes pump assembly 80, solenoid valve 82, IR module 84, bypass module 90, EC sensor modules 92, 98, 104, 110, and finally to an exhaust one of ports 24. The pneumatic circuit through the various components and docking stations can be formed by tubing, among other options.

A portion of the pneumatic circuit 60 extends from the inlet one of ports 20 to solenoid valve 82 to provide the gasses to solenoid valve 82. Solenoid valve 82 functions as a gate to control gas flow downstream through solenoid valve 82 to the rest of the pneumatic circuit. While solenoid valve 82 is shown disposed upstream of pump assembly 80, it is understood that solenoid valve 82 can be disposed upstream or downstream of pump assembly 80. Pump 122 draws gasses into gas analyzer 14 and pumps the gasses through the pneumatic circuit. Pump 122 can be a diaphragm pump, among other options. A pneumatic pathway extends between an outlet of solenoid valve 82 and an inlet of pump 122. For example, tubing can extend between solenoid valve 82 and pump 122.

Expansion chamber 124 is disposed downstream of pump 122 and is configured to absorb pulsation generated by operation of pump 122. A pneumatic pathway, which can be formed by tubing among other options, extends between an outlet of pump 122 and expansion chamber 124.

The gasses exit pump assembly 80 and flow downstream from pump assembly 80 to the portion of the pneumatic circuit associated with module carrier frame 120a. The pneumatic circuit extends serially through the docking stations of module carrier frame 120a, thereby flowing serially through the modules mounted on module carrier frame 120a. In the example shown, the gasses enter IR module 84 at the first docking station and through body 129a. The gasses flow through gas tube 133 and to second body 129b. The gasses exit IR module 84 through second body 129b and the third docking station.

A portion of the pneumatic circuit extends between module banks 60a, 60b. The portion of the pneumatic circuit extends from the final docking station of module carrier frame 120a in the direction of gas flow and to the first docking station of module carrier frame 120b in the direction of gas flow. The gas flows serially through the modules mounted on module carrier frame 120b, from bypass module 90 and through EC modules 92, 98, 104, 110, respectively, in the example shown. The gas exits the portion of the pneumatic circuit associated with module carrier frame 120b and flows through a pneumatic pathway (not shown), which can be formed by tubing among other options, to an exhaust one of ports 20 where the sample can exit gas analyzer 14.

The insertion of each module into the docking stations simultaneously makes mechanical, electrical, and pneumatic connections, as discussed in more detail below. Insertion of a module into a docking station causes a locking connection to occur, which holds the module in place while gas analyzer is in use, providing the mechanical connection. In some examples, the locking connection is a snap locking connection formed by inserting the module into the docking station. In some examples, the locking connection is further facilitated by a fastener securing the module to the docking station. When the module is in place, electrical contacts extending from the module contact with baseboard 64 to establish connections for both electrical power and data communications. Insertion of the module into the docking station also results in pneumatic connections being made, so that each module is connected to and forms part of the pneumatic circuit through gas analyzer 14.

The modular architecture of gas analyzer 14 provides significant advantages. Each individual module can be released from the docking station to allow replacement of the module with a newly calibrated sensor module. Each sensor module includes one or more circuit boards that include programmable module circuitry that carries calibration data that is provided to the control module 50 via the baseboard 64 and through the data communication connection established when the module is in place in the docking station. Each sensor module can also process the data generated to calculate the output reading provided to the user. The modularity also allows different combinations of sensor modules to be used. The modularity of gas analyzer 14 also facilitates updating and upgrading gas analyzer 14 in the field. For example, the user can upgrade the gas analyzer 14 in the field by swapping a new module configured to generate data regarding a parameter that the gas analyzer 14 was not configured to sense. The user can change the configuration of gas analyzer 14 while in the field by inserting a module measuring a type of gas that gas analyzer 14 was not previously configured to sense. Each smart module carries data with it that identifies the type of module and the calibration data for that module. Depending on the gasses to be tested, different combinations of sensor modules can be created. In addition, the user can utilize as many or as few active sensing modules as desired. Bypass modules 90 provide passthroughs forming a portion of the pneumatic circuit. Bypass modules 90 can be inserted at any desired location where a smart module is not mounted to complete the pneumatic circuit.

Figure 8:
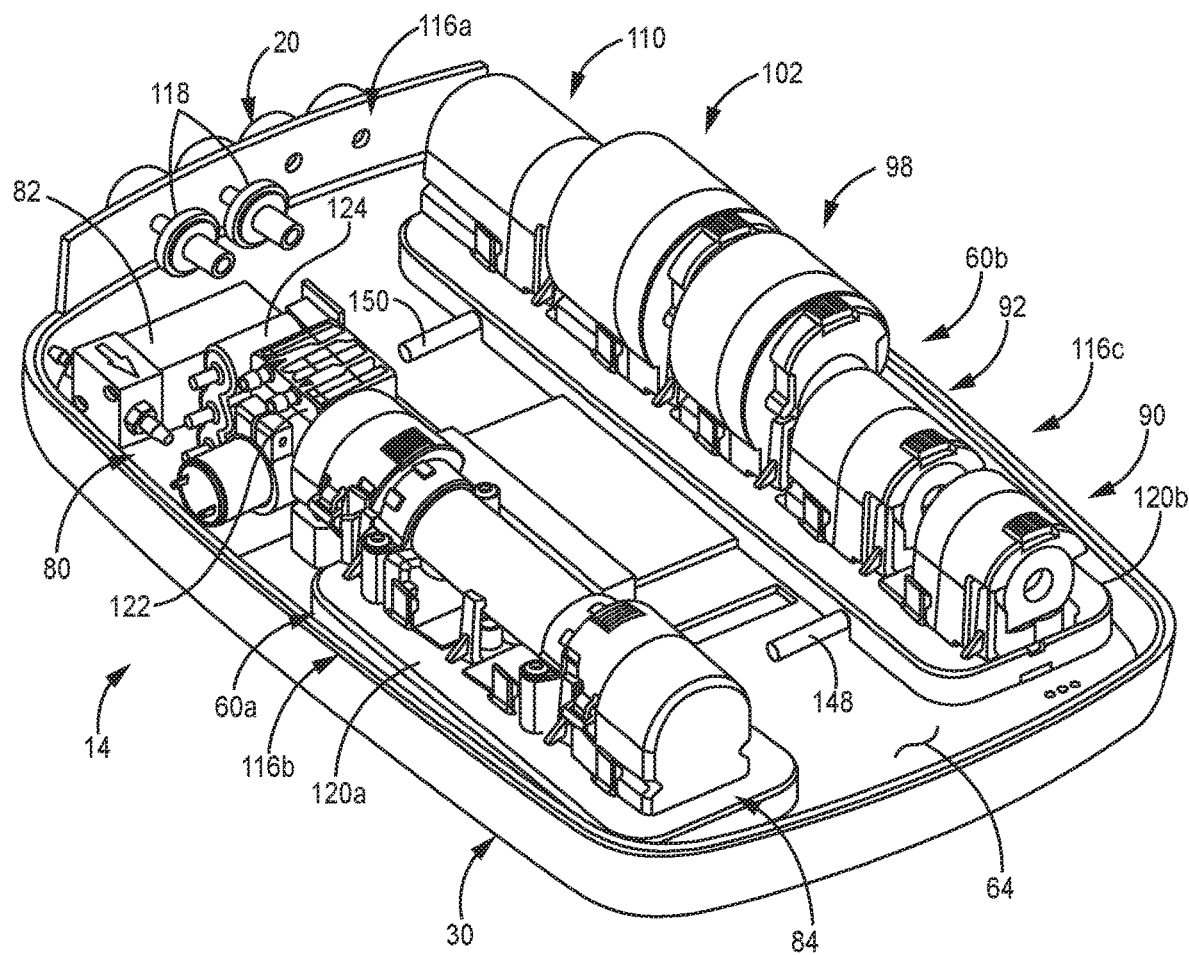
FIG. 8 is an isometric rear view of the modular gas analyzer with the battery pack and case back removed.

FIG. 8 is an isometric view of gas analyzer 14 with case back 28 and battery pack 26 removed. FIG. 8 shows baseboard 64 mounted within case top 30. Pump assembly 80 is electrically connected to baseboard 64. IR module 84 is mounted on first module carrier frame 120a, which in turn is mounted to baseboard 64. Second module carrier frame 120b is also mounted on baseboard 64, and supports bypass module 90 and EC modules 92, 98, 104, 110. While first and second module carrier frames 120a, 120b are shown as separate components, it is understood that gas analyzer 14 can include a single piece module carrier frame 120c, as discussed in more detail below with regard to FIGS. 12a and 12B. The single piece module carrier frame 120c can span between lateral sides of gas analyzer 14 and support both module banks 60a, 60b. Also shown in FIG. 8 are inlet tubing 148 and exhaust tubing 150. Inlet tubing 148 extends from an outlet of the final docking station (in the direction of gas flow) in first module bank 60a to the first docking station (in the direction of gas flow) in second module bank 60b. As such, gas samples passing through modules mounted in first module bank 60a, and on first module carrier frame 120a in the example shown, are then routed to modules mounted in second module bank 60b, and on second module carrier frame 120b in the example shown. For simplicity, only portions of tubes 148 and 150 are shown. While the pneumatic circuit is shown as including tubing, it is understood that the pneumatic circuit can be formed in any desired manner, such as integrally within carrier frames 120a, 120b, among other options.

The pneumatic circuit of gas analyzer 14 extends from an inlet one of ports 20 to pump assembly 80, through docking stations in first sensor compartment 116b, which docking stations are formed by module carrier frame 120a, through docking stations in second sensor compartment 116c, which docking stations are formed by module carrier frame 120b, and to an exhaust one of ports 20. The gas thus flows serially through the modules mounted at the various docking stations.

Figure 9A:
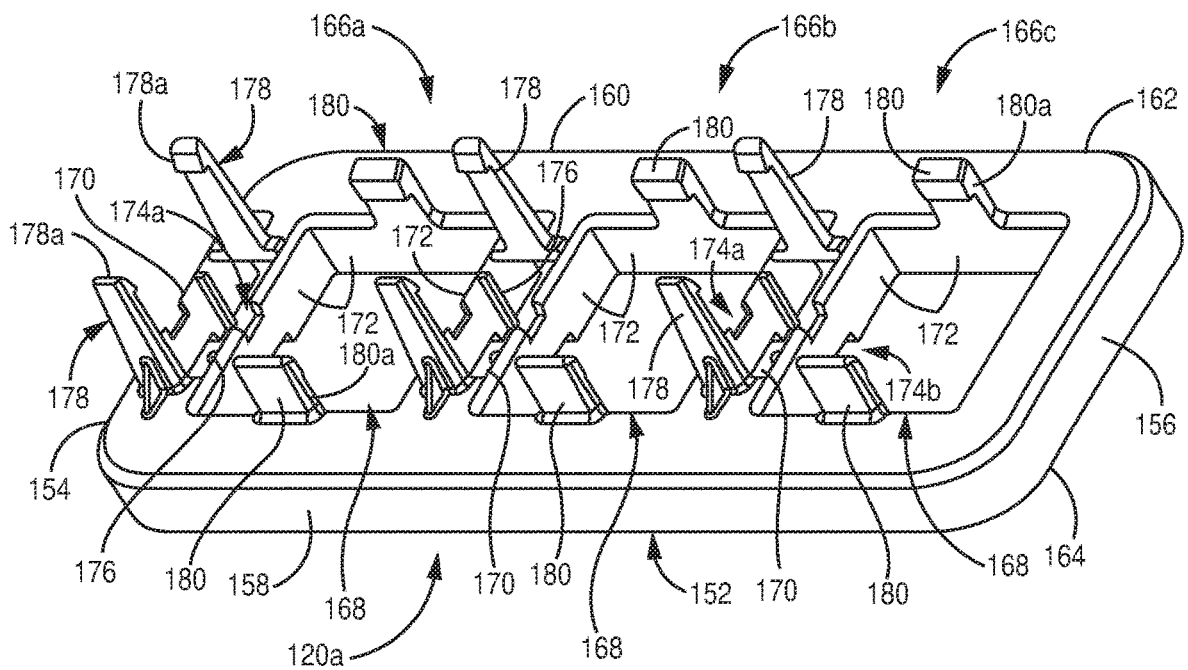
FIG. 9A is an isometric view of a first module carrier frame.
Figure 9B:
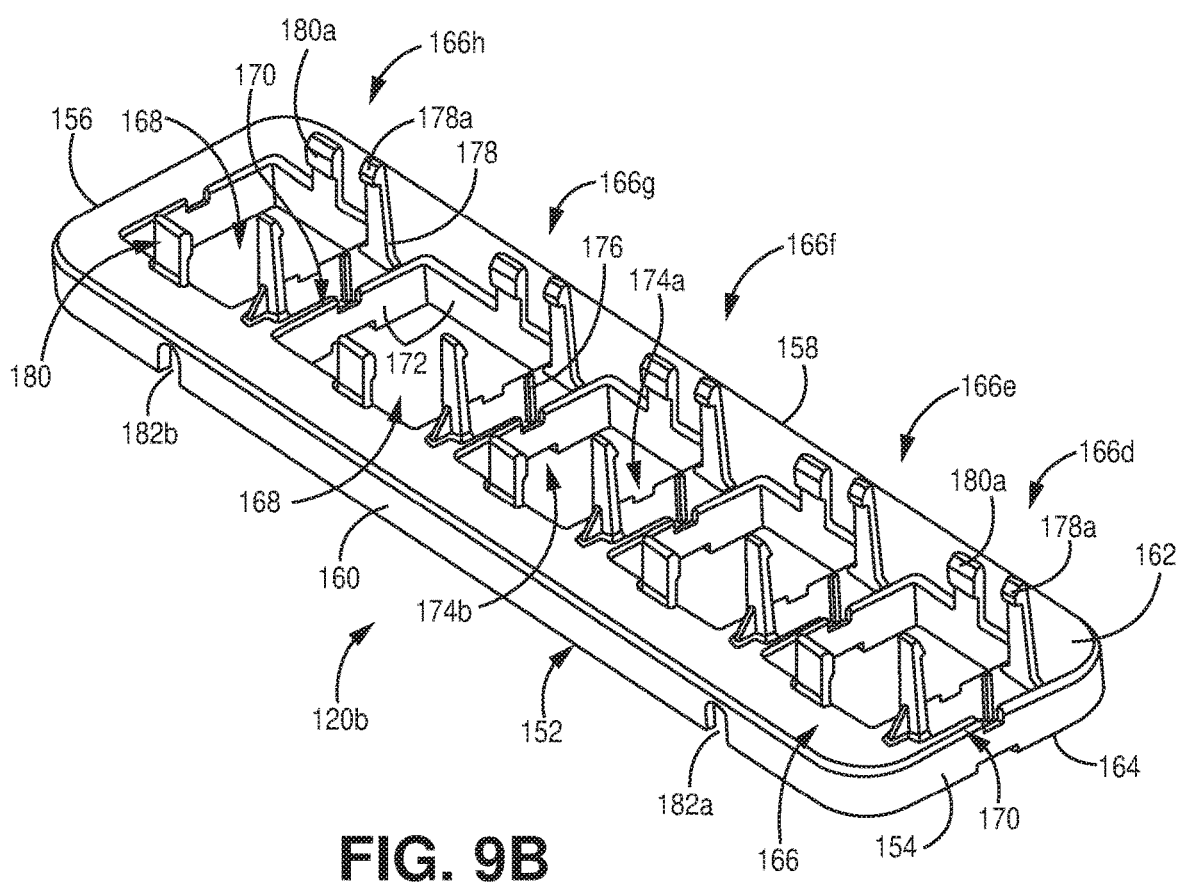
FIG. 9B is an isometric view of a second module carrier frame.

FIG. 9A is an isometric view of first module carrier frame 120a. FIG. 9B is an isometric view of second module carrier frame 120b. FIGS. 9A and 9B will be discussed together. Each of first module carrier frame 120a and second module carrier frame 120b include sidewall 152 having first end 154, second end 156, lateral sides 158 and 160, top side 162, and bottom side 164.

Docking stations 166a-166h (collectively herein "docking stations 166" and which can also be referred to as "internal bays") are configured to receive modules. Docking stations 166a-166c are formed in first module carrier frame 60 and docking stations 166d-166h are formed in second module carrier frame 78. Each docking station 166 includes a module receiving aperture 168 and a gas connect aperture 170. In the illustrated example, the apertures 168 of each of docking stations 166a-166f and 166h are identical while the aperture 168 of docking station 166g is larger such that docking station 166g can accommodate a larger module. Aperture 168 of docking station 166g has a longer aperture length than the apertures 168 of docking stations 166a-166f and 166*h*. It is understood that docking station 166*g* can also accommodate modules sized to fit within any of docking stations 166*a*-166*f* and 166*h*. Each docking station 166 is configured to provide a pneumatic connection and a mechanical connection to a module. Module receiving apertures 168 facilitate electrical connection with baseboard 64 as the modules can extend though the apertures 168 to contact baseboard 64.

Figure 10A:
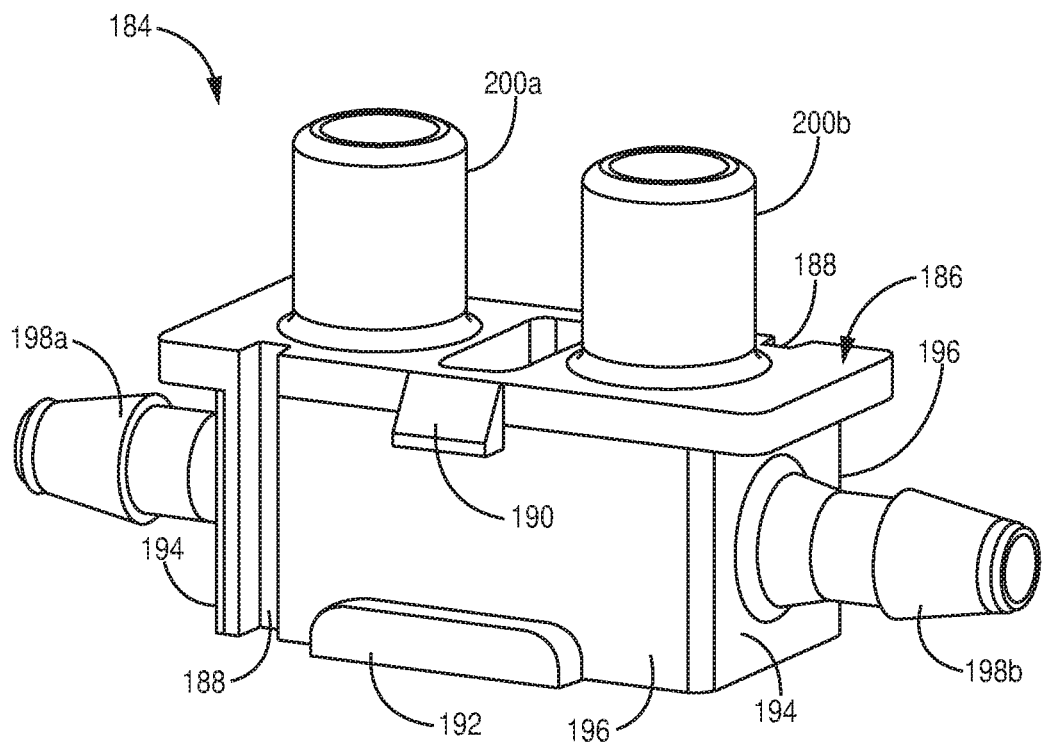
FIG. 10A is an isometric view of a gas interconnect.
Figure 10B:
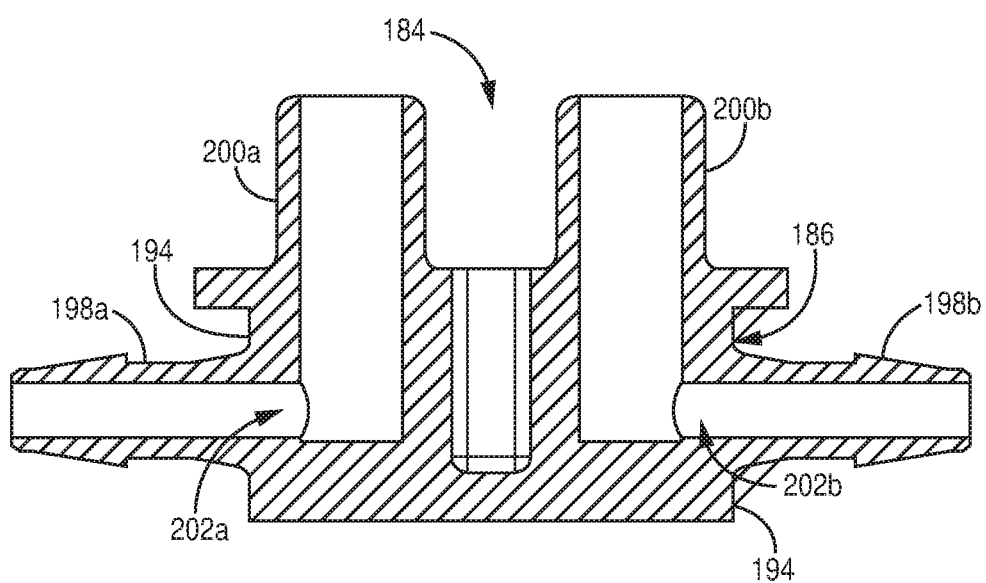
FIG. 10B is a cross-sectional view of the gas interconnect of FIG. 10A.

Apertures 168 are defined by sidewalls 172. Apertures 168 are configured to receive portions of modules mounted to the associated docking station 166. A gas interconnect receiver aperture 170 is formed on the upward or upstream side of each aperture 168. Apertures 170 are shaped to receive and hold a gas interconnect, such as gas interconnect 184 (FIGS. 10A and 10B). Notches 174*a*, 174*b* and ribs 176 are formed on opposite longitudinal sides of each aperture 170. Notches 174*a* are formed on a top side of module carrier frames 120*a*, 120*b* and notches 174*b* are formed on a bottom side of module carrier frames 120*a*, 120*b* opposite notches 174*a*. Notches 174*a*, 174*b* are formed in the longitudinal ones of sidewalls 172, which are the sidewalls 172 that span between sides 158, 160. Notches 174*a*, 174*b* receive portions of the gas interconnects to secure the gas interconnects to module carrier frames 60, 78 within apertures 170. Ribs 176 are received within slots formed on the gas interconnects to align the gas interconnects within apertures 170. Notches 174*a*, 174*b* have different shapes, which provides mistake-proofing that prevents inverted installation of gas interconnects. While docking stations 166 are described as including apertures 170 for receiving gas interconnects, it is understood that gas interconnects can be integrally formed with each docking station 168 to provide the pneumatic connection to modules.

Long retainer arms 178 are disposed on opposite lateral sides of each aperture 170. Long retainer arms 178 can also be referred to as connectors as long retainer arms 178 mechanically retain modules within each docking station 166. Long retainer arms 178 project further from module carrier frames 120*a*, 120*b* than short retainer arms 180. While long retainer arms 178 are shown on opposite sides of apertures 170 that the long retainer arms 178 are associated with, it is understood that long retainer arms 178 can project from module carrier frames 120*a*, 120*b* at any desired location suitable for mechanically engaging with the modules installed on module carrier frames 120*a*, 120*b*. Retainers 178*a* are formed at the distal ends of each retainer arm 178. In the example shown, retainers 178*a* are wedge shaped with a ledge formed on the bottom side of the wedge. It is understood, however, that retainers 178*a* can have any shape suitable for engaging with and mechanically securing the modules to the module carrier frame 120*a*, 120*b*. Long retainer arms 178 are configured to flex outward to widen a gap between long retainer arms 178 as a module is inserted into the associated docking station 166 and retainers 178*a* snap onto the module to mechanically secure the module within the docking station 166, as discussed in more detail below.

Disposed on opposite lateral sides of each aperture 168 are short retainer arms 180 associated with that aperture 168. Each short retainer arm 180 includes a retaining portion 180*a* at its upper end. In the example shown, the retaining portions 180*a* have a trapezoidal shaped contour, but it is understood that various other shapes are possible. Short retainer arms 180 form a snap lock connection with the module when the module is inserted into the aperture 168 of the docking station 166. Long retainer arms 178 and short retainer arms 180 can operate in conjunction to mechanically secure modules in place on carrier frames 120*a*, 120*b*.

As shown in FIG. 9B, notches 182*a*, 182*b* (collectively herein "notches 182") are formed on a bottom side of second module carrier frame 120*b*. Notches 182 provide openings through which pneumatic tubing can enter into and exit from second module carrier frame 120*b*. For example, inlet tubing 148 can extend through notch 182*a* and exhaust tubing 150 can extend through notch 182*b*. First module carrier frame 120*a* can include similar notches formed on the bottom side of side 160 to provide openings for tubing to enter into and exit from first module carrier frame 60. The notches 182 extend through side 160 on each of carrier frames 120*a*, 120*b*, which is the laterally inward side of the carrier frame 120*a*, 120*b* facing the battery slot 12*a*.

While module carrier frames 120*a*, 120*b* are descried as including long retainer arms 178 to facilitate a snap-lock connection, it is understood that the modules can be configured to mount in any desired manner. For example, the modules can be mounted to the docking stations via one or more fasteners, as discussed in more detail below. For example, a screw can secure the module to the module carrier frame 120*a*, 120*b*, which in some cases can be rotated less than a full 360-degree turn, such as a quarter turn among other options, between the locked and unlocked states. The screw can be turned by hand and may not require a separate tool.

FIG. 10A is an isometric view of gas interconnect 184. FIG. 10B is a cross-sectional view of gas interconnect 184. FIGS. 10A and 10B will be discussed together. Gas interconnect 184 is configured to mount within an aperture 170 (FIGS. 9A, 9B, 12*a*, 12B) in either one of carrier frames 120*a*-120*c* and provides pneumatic pathways for gas to enter into and/or exit from modules mounted to the docking station associated with the gas interconnect 184. Body 186 of gas interconnect 184 includes slots 188, upper projections 190 (only one of which is shown), and bosses 192 (only one of which is shown). Body 186 further includes lateral sides 194 and longitudinal sides 196. Slots 188, projections 190, and bosses 192 are formed on longitudinal sides 196. Slots 188 are configured to receive ribs 176 (FIGS. 9A and 9B). Projections 190 are configured to mount within notch 174*a* (FIGS. 9A and 9B) and bosses 192 are configured to mount within notch 174*b* (FIGS. 9A and 9B).

Piping connectors 198*a*, 198*b* (collectively herein "piping connectors 198") project from opposite lateral sides 194 of gas interconnect 184. Pneumatic tubing mounts to piping connectors 198 to provide gas to and receive gas from gas interconnect. Posts 200*a*, 200*b* (collectively herein "posts 200") extend vertically from a top surface of body 186. Posts 200 are cylindrical projections extending from the top side of body 186. A first pneumatic flowpath 202*a* extends through body 186 between piping connector 198*a* and post 200*a*. A second pneumatic flowpath 202*b* extends through body 186 between piping connector 198*b* and post 200*b*. The first and second flowpaths 202*a*, 202*b* are isolated within body 186 such that gasses cannot transition from one flowpath to the other within body 186.

During operation, the gas enters gas interconnect 184 through piping connector 198*a* and flows through the first pneumatic flowpath 202*a* to post 200*a*. The gas enters a module (such as any one of modules 84, 90, 92, 98, 104, 110) from post 200*a*. The gas exits the module and reenters gas interconnect through post 200*b*. The gas flows through the second pneumatic flowpath 202*b* and exits gas interconnect 184 through gas interconnect 198*b* to pneumatic tubing connected to gas interconnect 184. The gas continues downstream through the pneumatic tubing to the next module serially in line in the overall pneumatic flowpath in gas analyzer 14. It is understood that either one of posts 200a, 200b can be the inlet port while the other one of posts 200a, 200b can be the outlet port depending on the particular location within the pneumatic flowpath that gas interconnect 184 is located. Moreover, only one of posts 200a, 200b may be pneumatically connected to and form part of the pneumatic circuit, such as where a single module, such as IR module 84, is configured to receive gas at a first docking station and exhaust gas at a second docking station.

Figure 11:
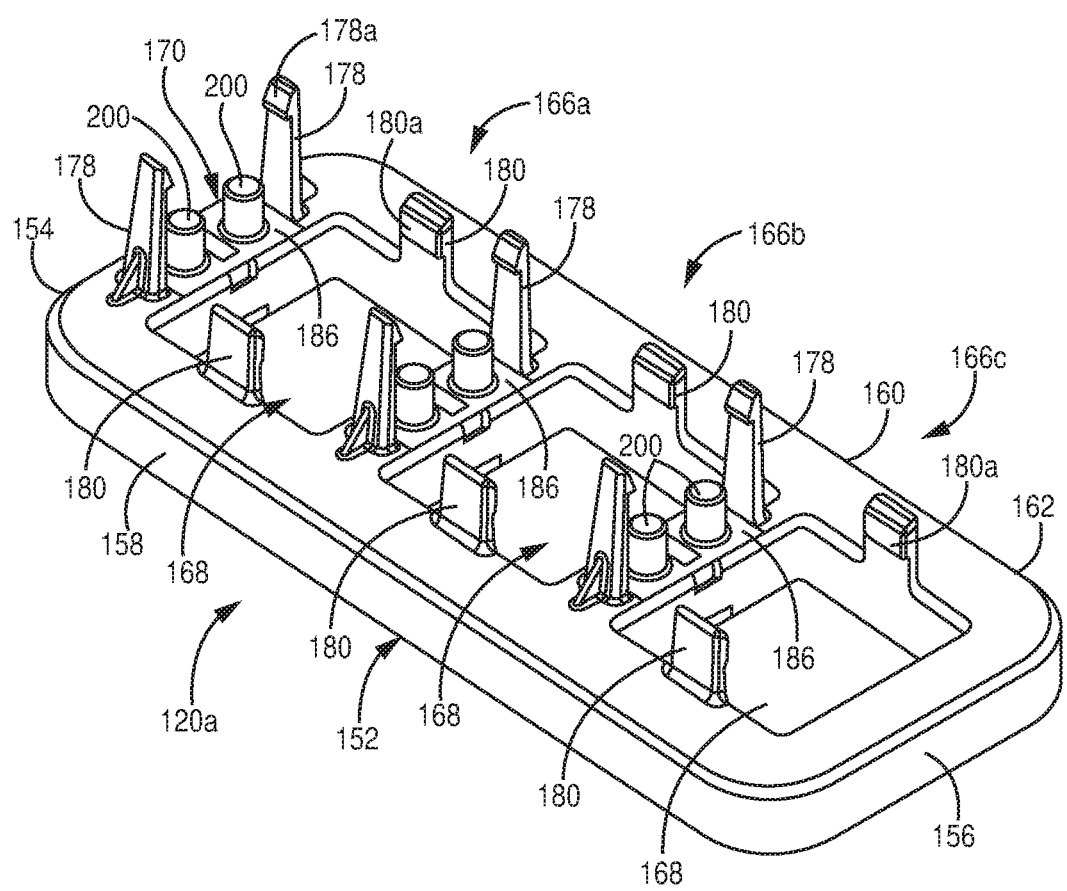
FIG. 11 is an isometric view of the first module carrier frame shown in FIG. 9A with gas interconnects inserted.

FIG. 11 is an isometric view of module carrier frame 120a showing gas interconnects 184 mounted to module carrier frame 120a. As shown, gas interconnects 184 mount within apertures 170 formed in module carrier frame 120a. With gas interconnects 184 mounted, posts 200 project vertically above the top side 162 of module carrier frame 120a. In the example shown, posts 200 are disposed between associated pairs of long arms 178. Piping connectors 198 (FIGS. 10A and 10B) are disposed below the top 162 of module carrier frame 120a. Upper projections 190 are disposed in notches 174a and bosses are disposed in notches 174b. Ribs 176 are disposed in slots 188.

Gas interconnects 184 can be mounted to module carrier frame 120a by inserting the gas interconnects 184 into apertures 170 from a bottom of module carrier frame 120a. Upper projections 190, which can be wedge shaped, initially encounter notches 174b and can push the longitudinal sides 172 defining aperture 170 apart. Upper projections 190 pass between the sides 172 and sides 172 snap back when upper projections 190 are disposed in notches 174a. Upper projections 190 engage notches 174a and bosses 192 engage notches 174b to retain gas interconnect 184 within aperture 170. It is understood that gas interconnects 184 mount to and are retained on second module carrier frame 120b and single piece module carrier frame 120c in the same manner as on first module carrier frame 120a.

Figure 12A:
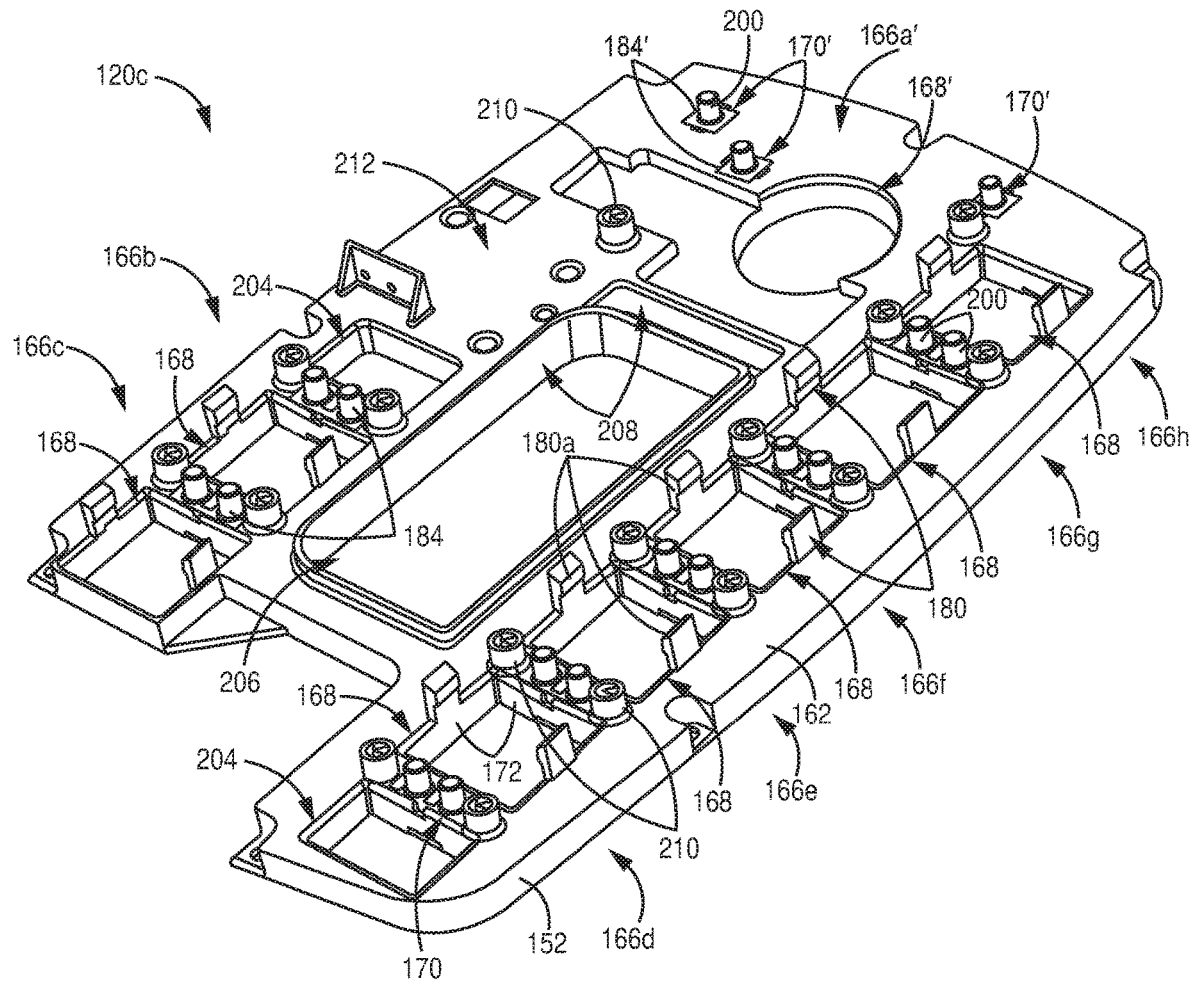
FIG. 12a is a top isometric view of a single piece module carrier frame with gas interconnects inserted.
Figure 12B:
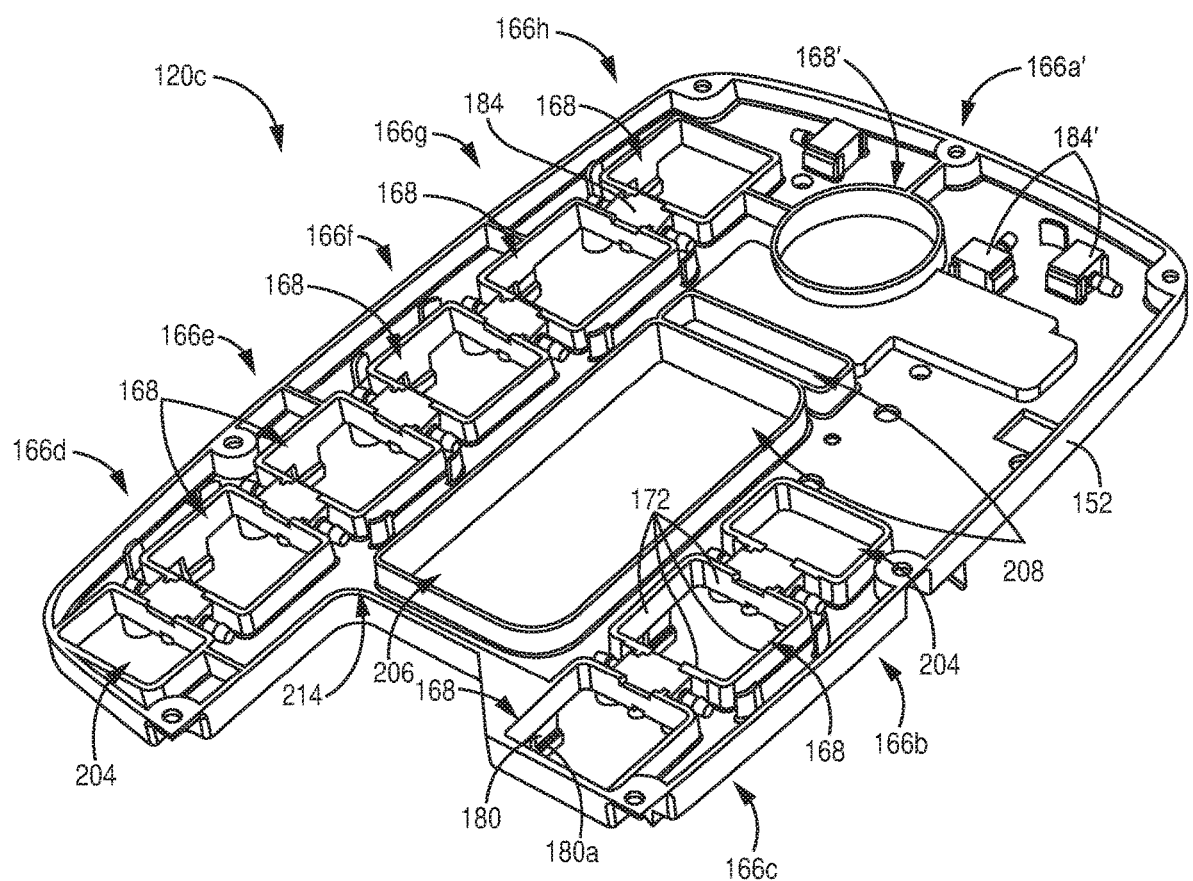
FIG. 12B is a bottom isometric view of the single piece module carrier frame of FIG. 12a with gas interconnects inserted.

FIG. 12a is a top isometric view of single piece carrier frame 120c. FIG. 12B is a bottom isometric view of single piece carrier frame 120c. FIGS. 12a and 12B will be discussed together. Carrier frame 120c is shown with gas interconnects 184, 184' installed on carrier frame 120c. Single piece carrier frame 120c is substantially similar to carrier frames 120a, 120b, except single piece carrier frame 120c is configured to support both module banks 60a, 60b. Sidewall 152 and top side 162 of carrier frame 120c are shown.

Carrier frame 120c is configured to be fixed within gas analyzer 14 over baseboard. Docking stations 166a'-166h (collectively herein "docking stations 166") are defined by carrier frame 120c and are configured to receive modules. In the example shown, docking station 166a' is different from other docking stations 166b-166h. Docking station 166a' is configured to receive a pressure module 74 (FIG. 4).

Each of docking stations 166b-166h includes a module receiving aperture 168 and a gas connect aperture 170. In the illustrated example, the apertures 168 of each of docking stations 166b-166f and 166h are identical while the aperture 168 of docking station 166g is larger such that docking station 166g can accommodate a larger module. Aperture 168 of docking station 166g has a longer aperture length than the apertures 168 of docking stations 166b-166f and 166h. It is understood that docking station 166g can also accommodate modules sized to fit within any of docking stations 166b-166f and 166h. Docking stations 166b and 166d further include module receiving apertures 204. Apertures 204 are configured to receive a portion of a module mounted at that docking station 166b, 166d that extends over gas connect aperture 170. For example, apertures 204 can receive the portion of body 129a of IR module 84 that extends outside of carrier frame 120a as shown in FIG. 7C. Each docking station 166 is configured to provide a pneumatic connection and a mechanical connection to a module. Module receiving apertures 168 facilitate electrical connection with baseboard 64 as the modules can extend though the apertures 168 to contact baseboard 64.

Sidewall 152 spaces top side 162 from baseboard 64 creating cavity 214 between carrier frame 120c and baseboard 64. Cavity 214 facilitates mounting of pneumatic tubing between carrier frame 120c and baseboard 64 and between various gas interconnects 184. The pneumatic tubing being covered by carrier frame 120c protects the pneumatic tubing from damage as modules are installed on and removed from carrier frame 120c.

Battery mount 206 is disposed centrally on module carrier frame 120c between first bank 60a and second bank 60b. Battery mount 206 includes apertures 208 that facilitate connection of battery pack 26 with baseboard 64 such that battery pack 26 can provide power to other components of gas analyzer 14. Pump mounting location 212 provides a location for mounting of pump assembly 80 and solenoid valve 82 to carrier frame 120c.

Apertures 168 are defined by sidewalls 172. Apertures 168 are configured to receive portions of modules mounted to the associated docking station 166. A gas interconnect receiver aperture 170 is formed on the upward or upstream side of each aperture 168. Apertures 170 are shaped to receive and hold gas interconnect 184. While docking stations 166 are described as including apertures 170 for receiving gas interconnects 184, it is understood that gas interconnects 184 can be integrally formed with each docking station 168 to provide the pneumatic connection to modules.

Docking station 166a' includes aperture 168' configured to receive a portion of a pressure module 74 to facilitate electrical connection with baseboard 64. Docking station 166a' further includes apertures 170' configured to receive gas interconnects 184'. Gas interconnects 184' are substantially similar to gas interconnects 184, except gas interconnects 184' define only a single gas flowpath and include a single post 200 for facilitating pneumatic connection with pressure module 74.

Fastener posts 210 are disposed on opposite lateral sides of each aperture 170 for docking stations 166b-166h. Docking station 166a' also includes associated fastener posts 210. Fastener posts 210 can also be referred to as connectors as fastener posts 210 facilitate mechanical retention of modules on carrier frame 120c. Fastener posts 210 are configured to receive fasteners to mechanically lock each module to its respective docking station 166. For example, a screw can secure the module to the module carrier frame 120c by insertion into fastener post 210. In some examples, the screw can be rotated less than a full 360-degree turn, such as a quarter turn among other options, between the locked and unlocked states. The screw can be turned by hand and may not require a separate tool. While carrier frame 120c is described as including fastener posts 210, it is understood that carrier frame 120c can include long retainer arms 178 similar to carrier frames 120a, 120b to facilitate a snap locking connection.

Disposed on opposite lateral sides of each aperture 168 are short retainer arms 180 associated with that aperture 168. Each short retainer arm 180 includes a retaining portion 180a at its upper end. In the example shown, the retaining portions 180a have a trapezoidal shaped contour, but it is understood that various other shapes are possible. Short retainer arms 180 form a snap lock connection with the module when the module is inserted into the aperture 168 of the docking station 166. Short retainer arms 180 are configured to flex outward to widen a gap between short retainer arms 180 as a module is inserted into the associated docking station 166 and retainers 180a snap onto the module to mechanically secure the module within the docking station 166, as discussed in more detail below. Short retainer arms 180 mechanically connect the module to carrier frame 120c.

Figure 13A:
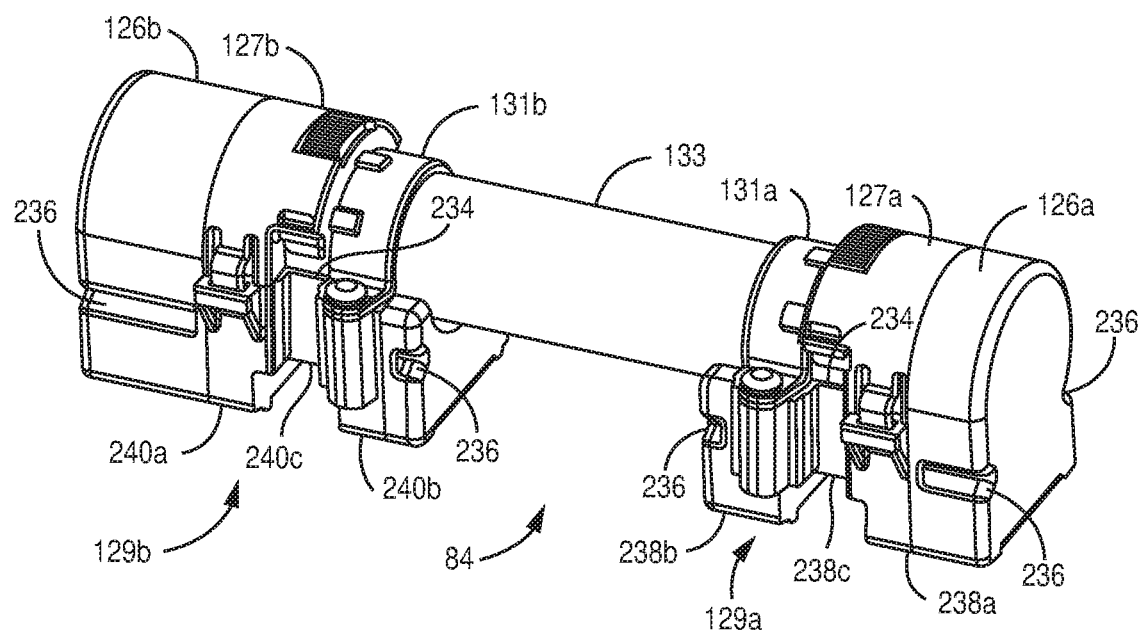
FIG. 13A is an isometric view of an infrared gas sensor that occupies three module positions.
Figure 13B:
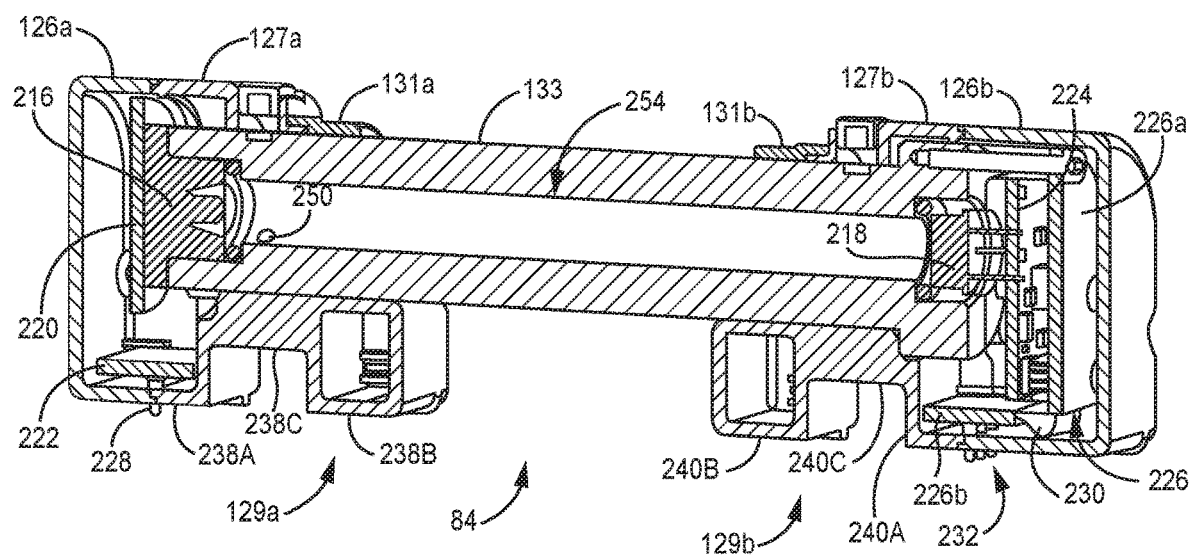
FIG. 13B is a cross-sectional view of the infrared gas sensor.
Figure 13C:
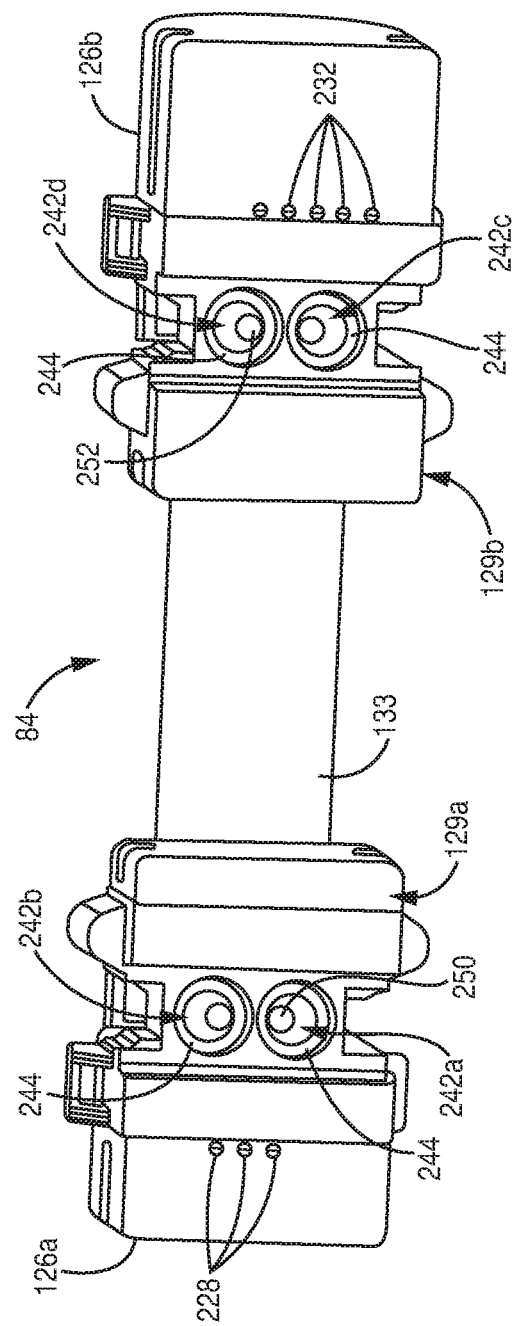
FIG. 13C is a bottom elevation view of the infrared gas sensor of FIG. 13A.
Figure 13D:
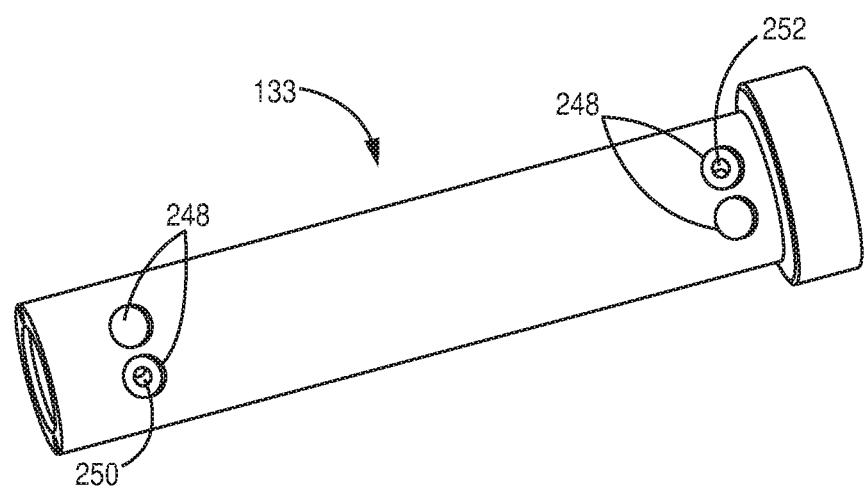
FIG. 13D is a bottom elevation view of the gas tube of the infrared sensor of FIG. 13A
Figure 13E:
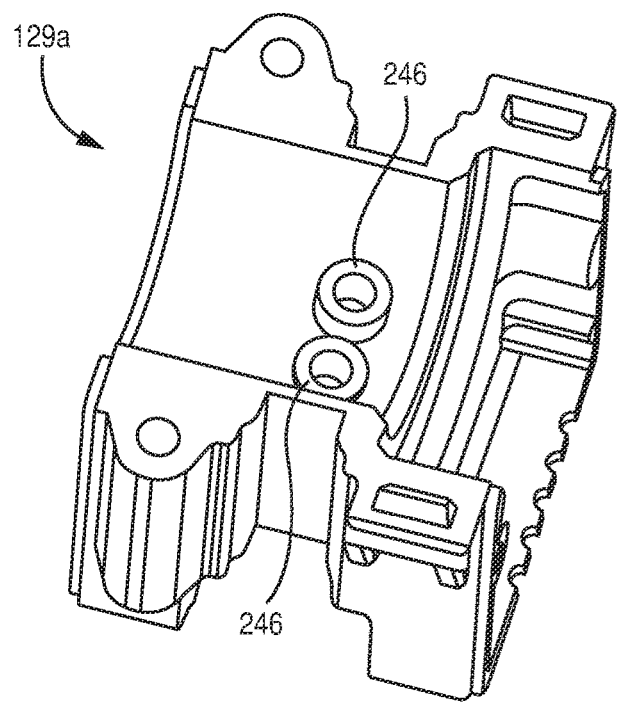
FIG. 13E is a top isometric view of a body of the infrared sensor.
Figure 13F:
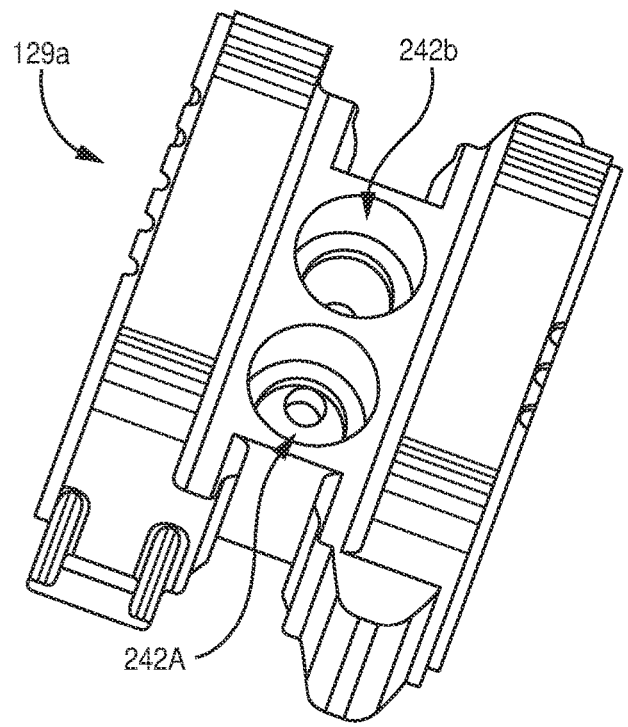
FIG. 13F is a bottom isometric view of a body of the infrared sensor.

FIG. 13A is an isometric view of IR module 84. FIG. 13B is a cross-sectional view of IR module 84. FIG. 13C is a bottom view of IR module 84. FIG. 13D is a bottom view of gas tube 133. FIG. 13E is a top isometric view of body 129a. FIG. 13F shows a bottom isometric view of body 129a. IR module 84 is a gas analyzing sensor that utilizes absorption to determine various characteristics of the gas flowing through gas tube 133. The IR module 84 shown is a three-bay module that spans three docking stations 166 in one of module carrier frames 120a-120c. While IR module 84 spans three docking stations 166, IR module 84 is mounted to two of the three docking stations 166. IR module 84 is configured to mechanically, pneumatically, and electrically connect at two of the three docking stations 166. IR module 84 spans over the intermediate docking station 166 without forming a pneumatic or electric connection with that intermediate docking station 166. In some examples, IR module 84 is not mechanically connected to the intermediate docking station 166.

Housing 127a, body 129a and cap 126a combine to form a first mounting module of IR module 84. Housing 127b, body 129b, and cap 126b combine to form a second mounting module of IR module 84. It is understood that housing 127a can be identical to housing 127b. It is understood that body 129a can be identical to body 129b. It is understood that U-clips 131a and 131b can be identical. Cap 126a differs from cap 126b in that cap 126a has a shorter longitudinal length. The differences in length alter the size of the cavity disposed within each of the mounting modules to facilitate enclosure of sensing components and circuitries of various sizes.

Gas tube 133 extends between emitter 216 and detector 218. Emitter 216 is disposed in a chamber defined by module cap 126a, housing 127a, and body 129a. Detector 218 is disposed at the opposite end of gas tube 133 from emitter 216. Body 129a is disposed below and attached to housing 127a. Body 129a can be attached to housing 127a in any desired manner, such as by a snap lock connection or fasteners, among other options. U-clip 131a extends over gas tube 133 and is connected to body 129a by fasteners. It is understood that U-clip 131a can be connected to body 129a in any desired manner, such as by a hinge and snap lock, among other options. Module cap 126a is connected to housing 127a and body 129a and encloses the chamber that circuit boards 220, 222 are disposed in. Body 129b is disposed below and attached to housing 127b. Body 129b can be attached to housing 127b in any desired manner, such as by a snap lock connection or fasteners, among other options. Body 129b can be identical to body 129a. U-clip 131b extends over gas tube 133 and is connected to body 129b by fasteners, among other options. Module cap 126b is connected to housing 127b and body 129b and encloses the chamber that circuit boards 224, 226 are disposed in.

Circuit boards 220, 222 are associated with emitter 216 and disposed in the chamber defined by cap 126a, housing 127a, and body 129a. Spring pins 228 (only one of which is shown) extend from circuit board 222. Spring pins 228 provide power and data signals between emitter 216 and baseboard 64. As such, spring pins 228 provide electrical connection between the emitter end of IR module 84 and baseboard 64. In some examples, emitter 216 can be soldered to circuit board 220. Emitter 216 is configured to emit light, such as infrared light, into gas tube 133. In some examples, IR module 84 can include a pressure sensor configured to sense the pressure of gasses at IR module 84.

Detector 218 is disposed at an opposite end of gas tube 133 from emitter 216. Detector 218 can be of various configurations to detect various gasses. Circuit boards 224 and 226 are associated with detector 218. In the example shown, circuit board 226 includes two boards 226a, 226b connected by flex connector 230. Spring pins 232 extend from circuit board 226b. Spring pins 232 provide power and data signals between to detector 218 and baseboard 64. As such, spring pins 232 provide electrical connection between the detector end of IR module 84 and baseboard 64. Circuit board 224 can be an amplifier board for amplifying the signal generated by detector 218. Circuit board 226a can include a second amplifier for providing a second stage of signal amplification. Circuit board 226 can include a microcontroller, which can form part or all of the programmable module circuitry 86 (FIG. 4) of IR module 84. The microcontroller can receive analog signals from detector 218, perform mathematical functions to create a linearized output, and communicates the output to analyzer controller 50 (FIGS. 3 and 4) via spring pins 232. Emitter 216 and detector 218 can be referred to as a sensing component of IR module 84. Emitter 216 and detector 218 can be considered to form the transducer 88 (FIG. 4) of IR module 84.

IR module 84 includes mechanical connectors configured to secure IR module 84 within docking stations 166, as discussed in more detail below. In the example shown shoulders 234 are formed on each of bodies 129a, 129b and are configured to be engaged by retainers 178a of long arms 178. Shoulders 234 being engaged by long retainer arms 178 mechanically locks IR module 84 onto its associated module carrier 120a-120c. While IR module 84 is described as including shoulders 234 for forming a snap locking connection with long arms 178, it is understood that IR module 84 can be locked to the associated module carrier 120a-120c in any desired manner. In some examples, IR module 84 can include features for receiving one or more fasteners for locking IR module 84 to module carrier frame 120a-120c by the one or more fasteners. For example, IR module 84 can include features similar to those shown in FIGS. 19A and 19B for receiving a fastener (FIG. 19C), the fastener configured to extend into fastener posts 210 (FIGS. 12a and 12B) for locking IR module 84 to the module carrier frame.

Grooves 236 are formed on each of caps 126a, 126b and bodies 129a, 129b and are configured to be engaged by retainers 180a of short arms 180 to mechanically secure IR module 84 to the associated module carrier frame 120a-120c. In some examples, cap 126a is one of disposed outside of the module carrier frame 120a (as shown in FIG. 7C) or disposed in an aperture 204 (FIGS. 12a and 12B) that does not include an associated pair of short retainer arms 180 such that the groove 236 formed on cap 126a is not engaged by short retainer arms 180.

When IR module 84 is mounted, body 129a spans across the portion of the module carrier frame 120a-120c that defines the upstream most aperture 170 associated with IR module 84. A first portion 238a of body 129a is disposed on a first, upstream side of the aperture 170, a second portion 238b of body 129a is disposed on a second, downstream side of the aperture 170, and a third portion 238c of body 129a spans over the aperture 170. When mounted, body 129b spans across the portion of the module carrier frame that defines the downstream most aperture 170 associated with IR module 84. A second portion 240b of body 129b is disposed on a first, upstream side of the aperture 170, a first portion 240a of body 129b is disposed on a second, downstream side of the aperture 170, and a third portion 240c of body 129b spans over the aperture 170.

Posts 200 of the gas interconnect 184 in the upstreammost aperture 170 associated with body 129a extend into receiving openings 242a, 242b formed in body 129a. The receiving openings 242a, 242b are formed in third portion 238c of body 129a. While posts 200 are described as projecting from gas interconnect 184 into receiving openings 242a, 242b, it is understood that posts can be formed on and extend from body 129a and gas interconnects 184 can include ports configured to receive the posts. O-rings 244 are disposed in receiving openings 242a, 242b and engage the tops of posts 200 to seal the pneumatic connection between the gas interconnect 184 and body 129a. Each of bodies 129a, 129b includes projections 246 that extend into counterbores 248 formed in gas tube 133. Projections 246 extending into counterbores 248 locate gas tube 133 relative to bodies 129a, 129b and prevent undesired rotation of gas tube 133.

Opening 250 is formed in gas tube 133 and provides a pathway for gas to enter into pneumatic chamber 254 defined within gas tube 133. The inlet one of posts 200 of the upstream gas interconnect 184 extends into the receiving opening 242a associated with opening 250 to provide gas to gas tube 133. The outlet one of posts 200 extends into the other receiving opening 242b, but gas tube 133 does not include an opening to allow gas to flow to receiving opening 242b. Instead, the gas flows through gas tube 133 and exits through opening 252 and receiving opening 242d.

Posts 200 of the gas interconnect 184 in the downstreammost aperture 170 associated with IR module 84 extend into receiving openings 242c, 242d formed in body 129b. The receiving openings 242c, 242d are formed in third portion 240c of body 129b. O-rings 244 are disposed in receiving openings 242c, 242d and engage the tops of posts 200 to seal the pneumatic connection between the gas interconnect 184 and body 129b. Opening 252 is formed in gas tube 133 and provides a pathway for gas to exit from gas tube 133 to the downstream gas interconnect 184 interfacing with IR module 84. The outlet one of posts 200 of the downstream gas interconnect 184 extends into the receiving opening 242d associated with opening 252 to receive gas from gas tube 133. The inlet one of posts 200 extends into the other receiving opening 242c, but gas tube 133 does not include an opening to allow gas flow through receiving opening 242c.

IR module 84 can be installed and removed on any one of module carrier frames 120a-120c. To install IR module 84, IR module 84 is positioned over associated docking stations and lowered vertically. Long arms 178 engage with the sides of bodies 129a, 129b, pushing the long arms 178 apart. As IR module 84 is lowered, short arms 180 engage with the sides of caps 126a, 126b, pushing short arms 180 apart. IR module 84 continues to be lowered and posts 200 extend into receiving openings 242a-242d. IR module 84 continues to be lowered. Retainers 178a of the long arms 178 snap over shoulders 234 formed by each of bodies 129a, 129b. Retaining portions 180a engage with grooves 236. The long arms 178 and short arms 180 engaging with shoulders 234 and grooves 236 mechanically secures IR module 84 to the module carrier frame 120a-120c that IR module 84 is mounted to. Shoulders 234 and grooves 236 can be considered as forming receiving portions of IR module 84 that mechanically secure IR module 84. Spring pins 228, 232 contact baseboard 64 to provide electrical power and data connections. Posts 200 extend into openings 242a-242d to provide pneumatic connections.

IR module 84 can be removed by activating the release mechanism associated with each housing 129a, 129b. Activating the release mechanism, such as by depressing a button of the release mechanism, widens the gap between long arms 178 such that long arms 178 disengage from shoulders 234. With long arms 178 is engaged from shoulders 234, the IR module 84 can be lifted vertically, breaking the mechanical, electrical, and pneumatic connections. Another IR module 84, or other type of module, can be installed in the docking stations that IR module 84 occupied.

Figure 14A:
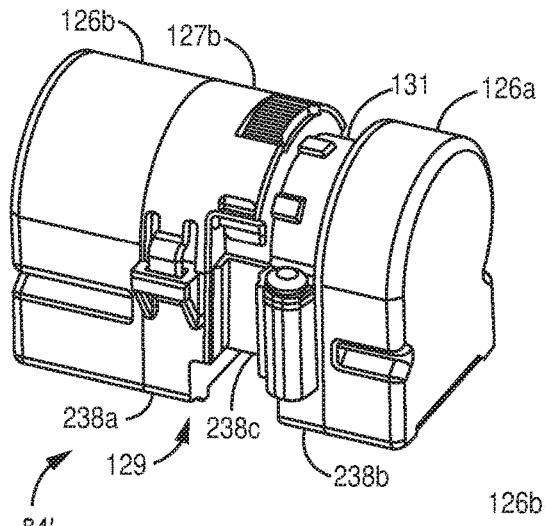
FIG. 14A shows another infrared gas sensor.

FIG. 14A is an isometric view of IR module 84'. IR module 84' is similar to IR module 84 (best seen in FIGS. 13A-13C), except the gas tube (not shown) of IR module 84' is shorter than gas tube 133 of IR module 84 such that IR module 84' is configured to occupy either one or two docking stations 166, depending on the location that IR module 84' is mounted. IR module 84' further includes a single body 129 and U-clip 131. The single body 129 both receives gas into IR module 84' and exhaust gas from IR module 84'. For example, if IR module 84' is mounted at docking station 166a (FIGS. 9A and 11), then IR module 84' occupies that single docking station with cap 126a and second portion 238a disposed outside of the docking station 166a, similar to IR module 84 as shown in FIG. 7C, and first portion 238a and cap 126b disposed in the aperture 168 of docking station 166a.

When mounted to module carrier 120c (FIGS. 12a and 12B), IR module 84' can be mounted to docking station 166b such that second portion 238b and cap 126a are disposed in aperture 204 and first portion 238a and cap 126b are disposed in the aperture 168. In other examples, IR module 84' can occupy two aperture 168 of adjacent docking stations, such as where IR module is mounted in docking stations 166e, 166f as body 129a spans over the aperture 170 and is partially disposed in the apertures 168 of each docking station.

Figure 14B:
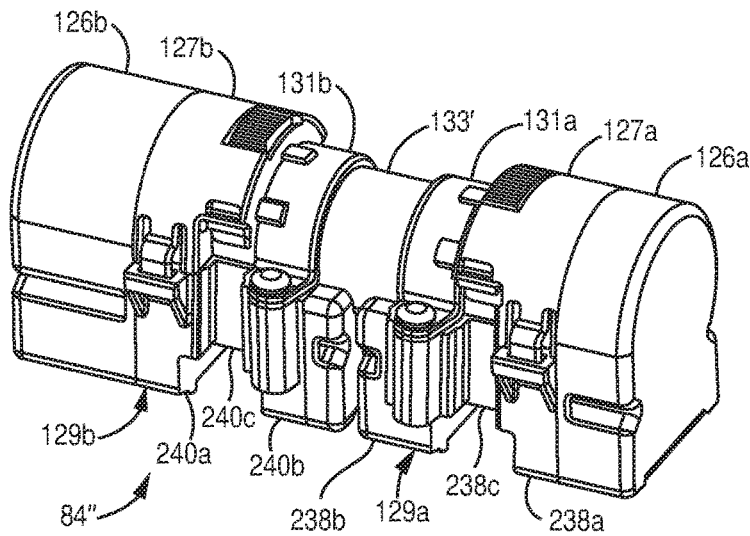
FIG. 14B shows another infrared gas sensor.

FIG. 14B is an isometric view of IR module 84". IR module 84" is similar to IR module 84 (best seen in FIGS. 13A-13C), except the gas tube 133' of IR module 84" is shorter than gas tube 133 of IR module 84 such that IR module 84" is configured to occupy either two or three docking stations 166. For example, if IR module 84" is mounted at docking stations 166a, 166b (FIGS. 9A and 11) or docking stations 166b, 166c (FIGS. 12a and 12B), then IR module 84' occupies those two docking stations. In other examples, IR module 84' can occupy three adjacent docking stations, such as where IR module is mounted in docking stations 166d-166f.

Figure 14C:
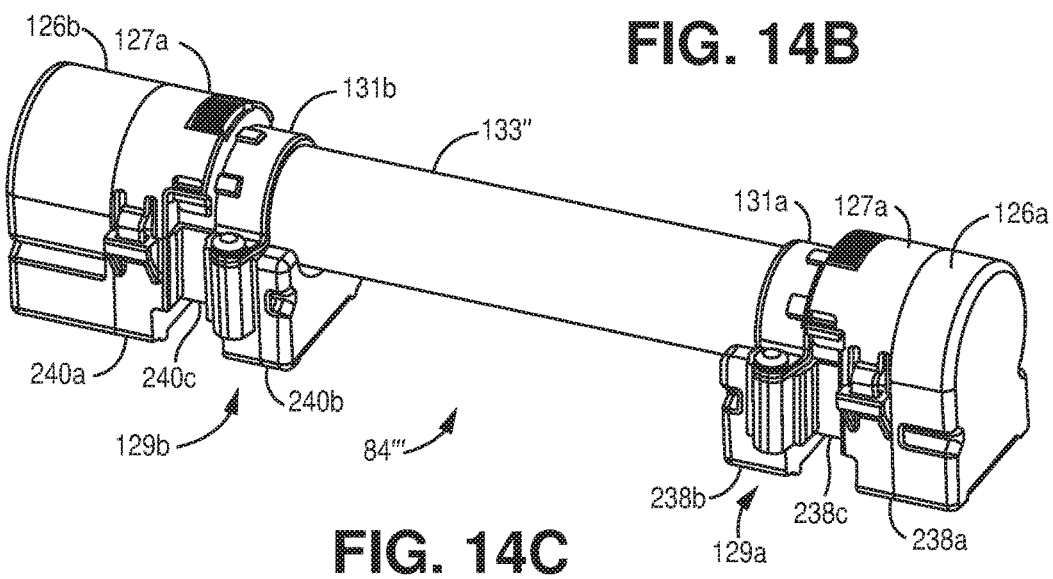
FIG. 14C shows another infrared gas sensor.

FIG. 14C is an isometric view of IR module 84'''. IR module 84''' is similar to IR module 84 (best seen in FIGS. 13A-13C), except the gas tube 133" of IR module 84''' is longer than gas tube 133 of IR module 84 such that IR module 84' is configured to occupy either four or five docking stations 166.

FIGS. 15A-15H illustrate the sequence of mounting of bypass module 90 on the second module carrier frame 120b. It is understood that the described sequence of mounting is applicable to each of IR module 84 and EC modules 92, 98, 104, 110.

Figure 15A:
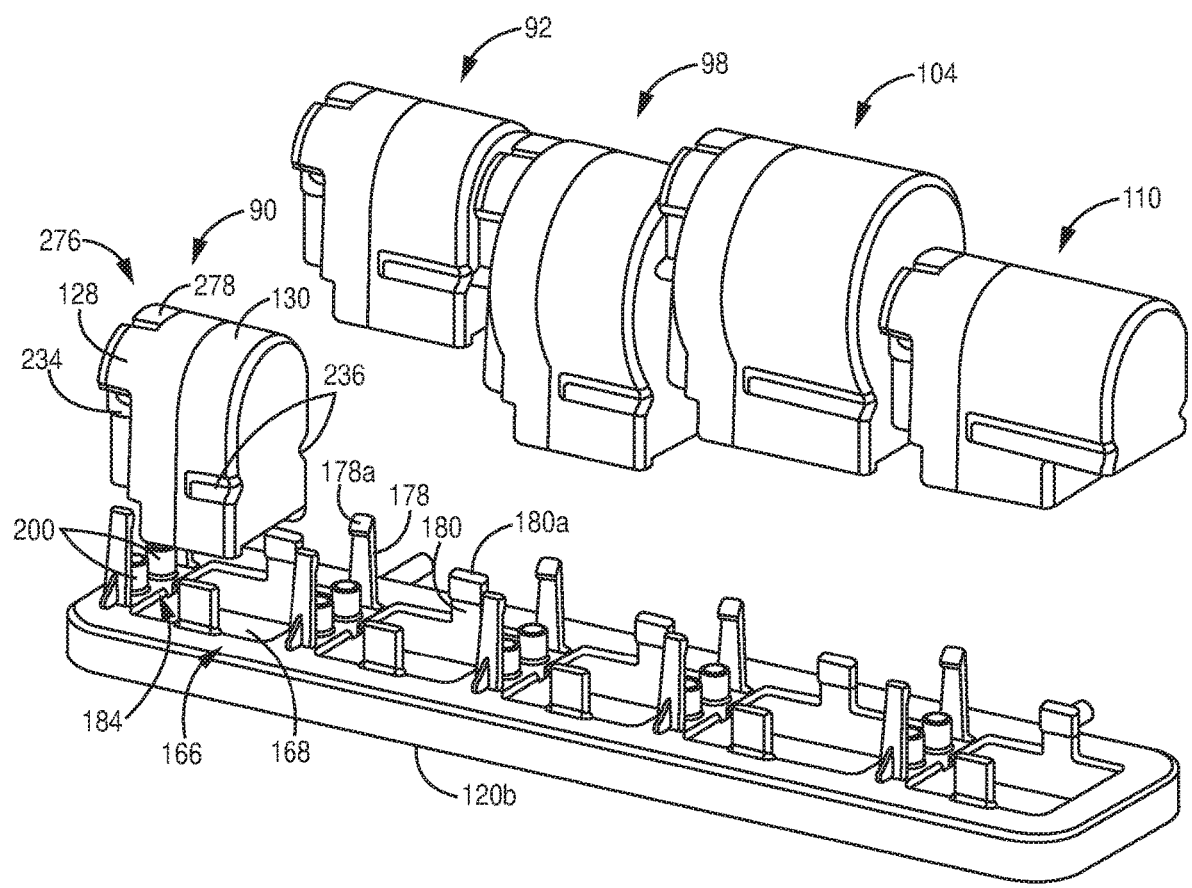
FIGS. 15A-15H illustrate a sequence of installing one of the modules into a module carrier frame.
Figure 15B:
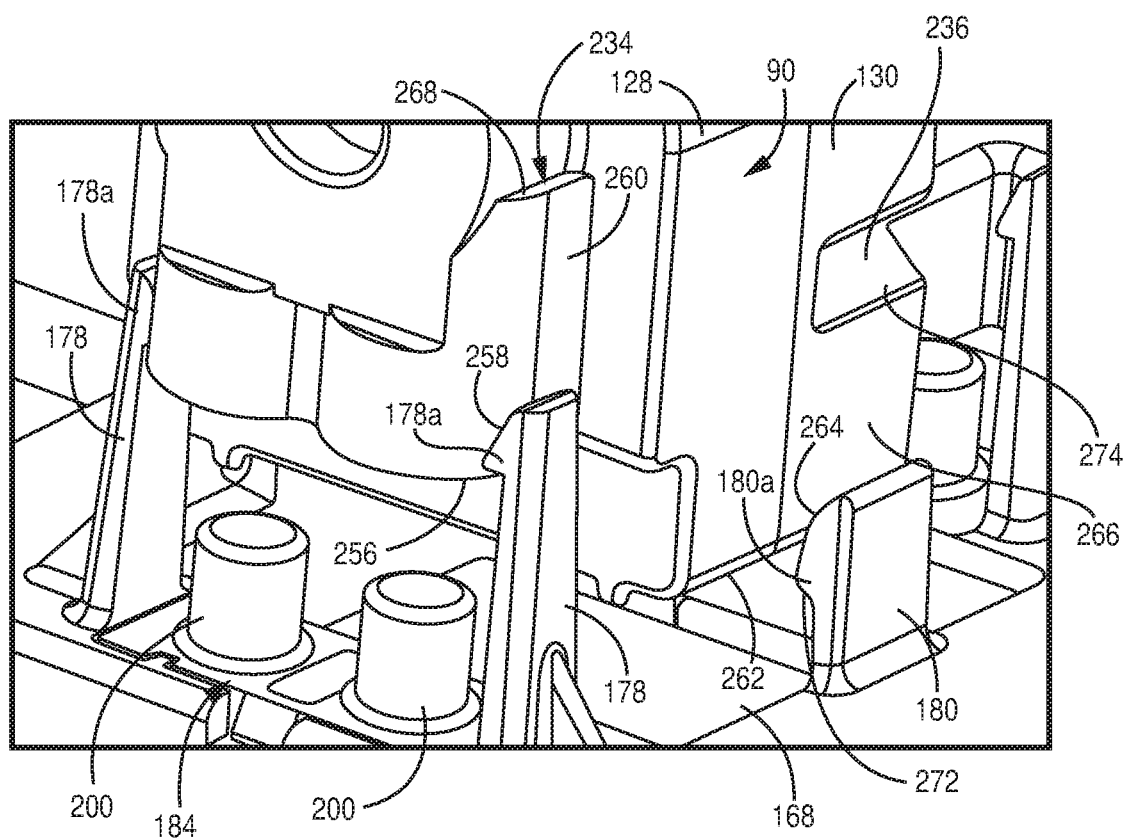
Figure 15C:
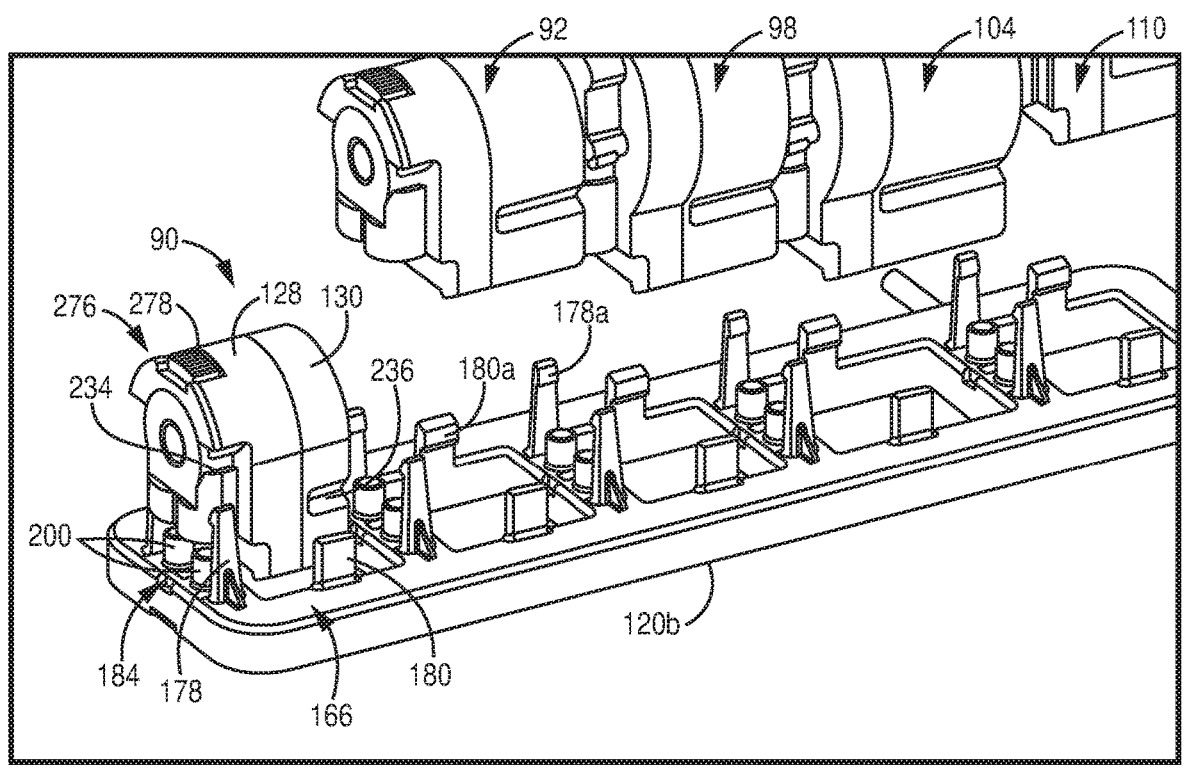
Figure 15D:
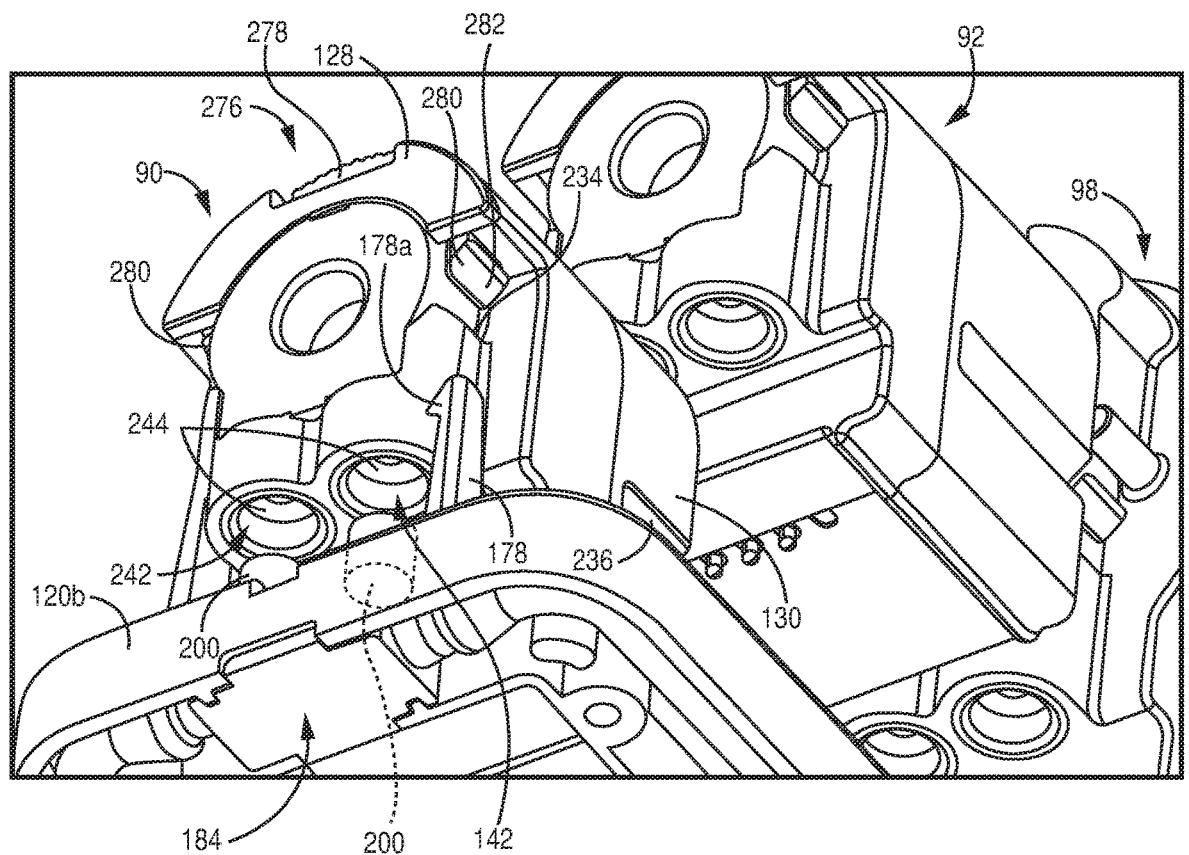
Figure 15E:
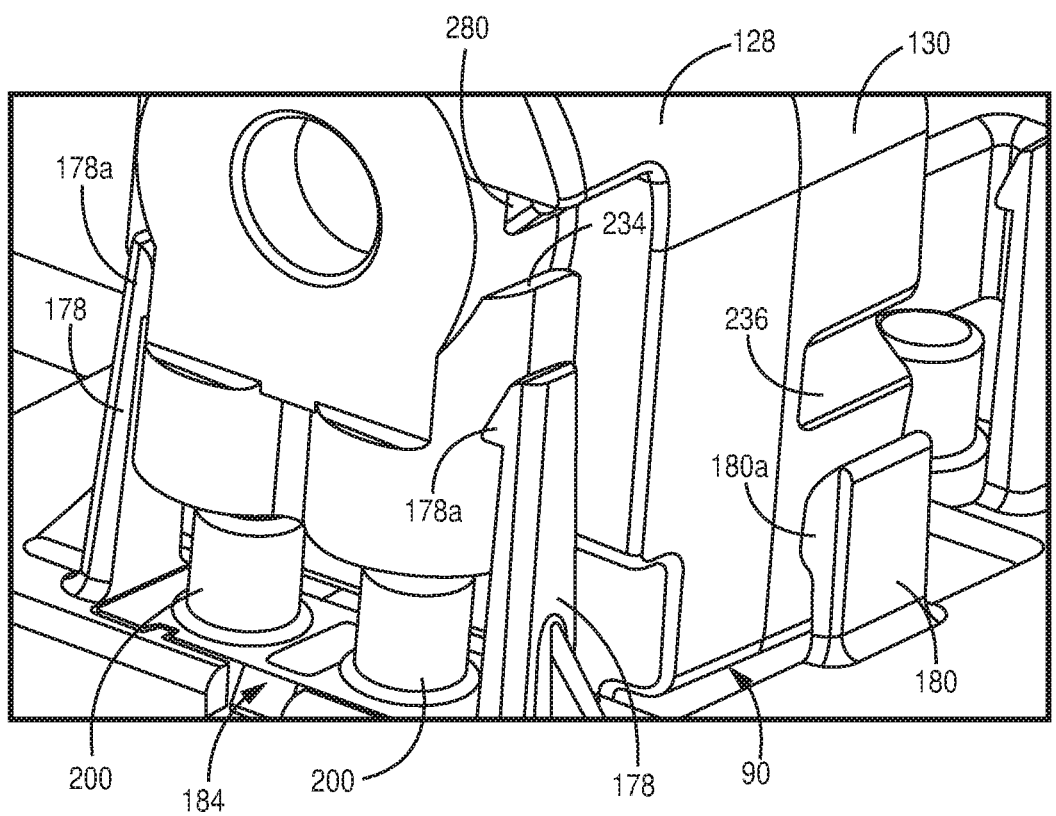
Figure 15F:
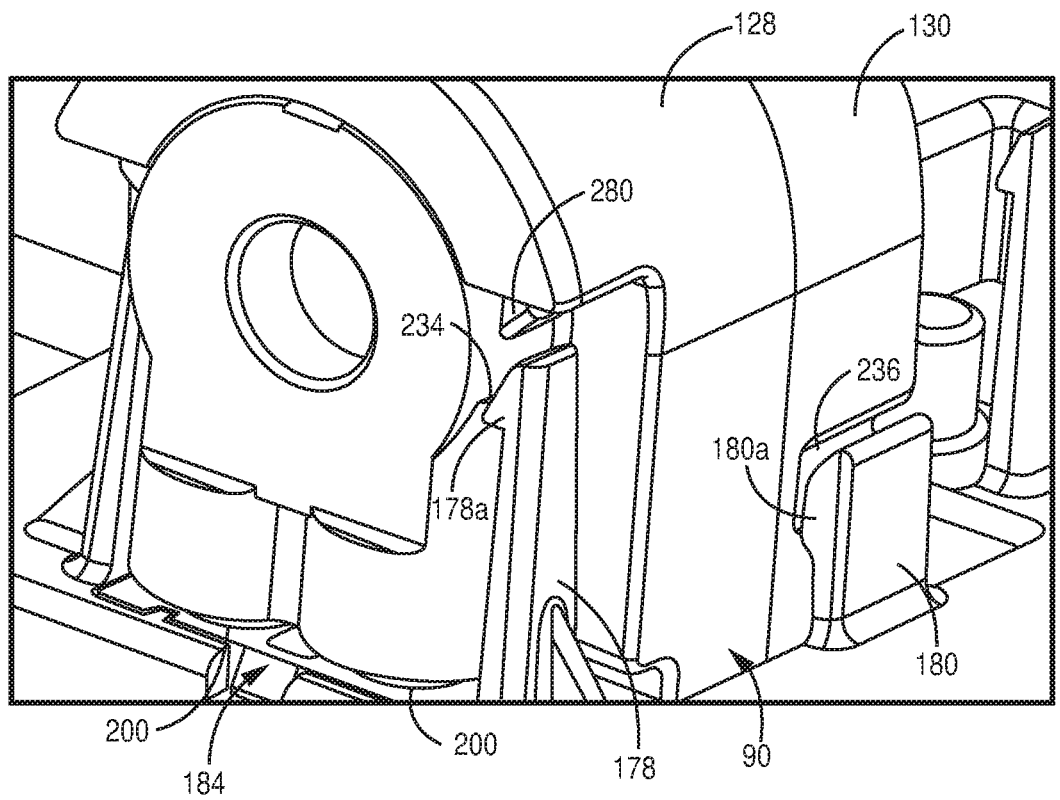

Module 90 is aligned with and lowered into a docking station 166. As seen in FIG. 15B, retainers 178a of long arms 178 encounter bottom edge 256 of module body 128. The module body 128 can be considered to form a module housing. The bottom end 256 of module body 128 engages the sloped portions 258 of retainers 178a and exerts a force on retainers 178a to widen the gap between retainers 178a. As module 90 continues to descend into docking station 166, retainers 178a slide over lateral sides 260 of module body 128. Short arms 180 encounter the bottom edge 262 of cap 130. The bottom edge 262 of cap 130 engages the sloped upper edges 264 of retainers 180a and exerts a force on retainers 180a to cause short retainer arms 180 to flex and widen the gap between retainers 180a. As module continues to descent into docking station 166, retainers 180a slide over the lateral sides 266 of cap 130.

Module 90 continues to descend into docking station 166a and posts 200 extend into and are received by receiving openings 242 of module body 128. Posts 200 and receiving openings 242 are sized such that posts 200 extend far enough into receiving openings 242 to engage o-rings 244 disposed in receiving openings 242. Posts 200 engaging o-rings 244 creates an air-tight seal to close the pneumatic flowpath. Module body 128 and cap 134 are partially disposed within aperture 134.

Figure 15G:
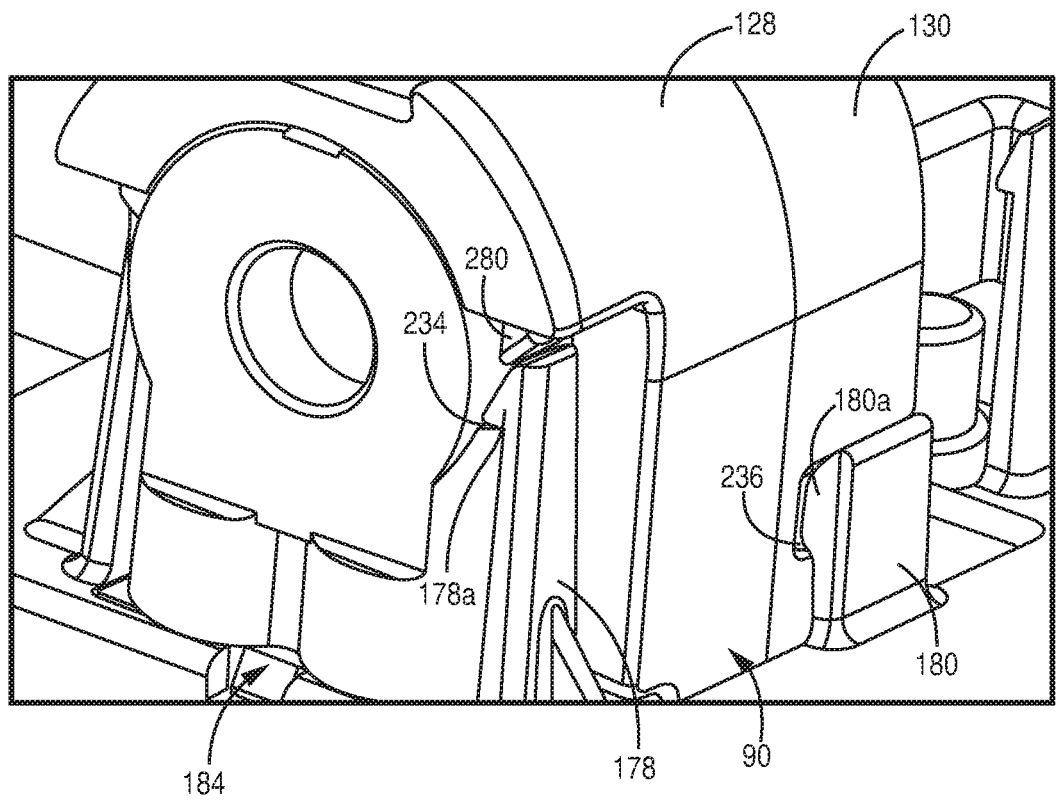
Figure 15H:
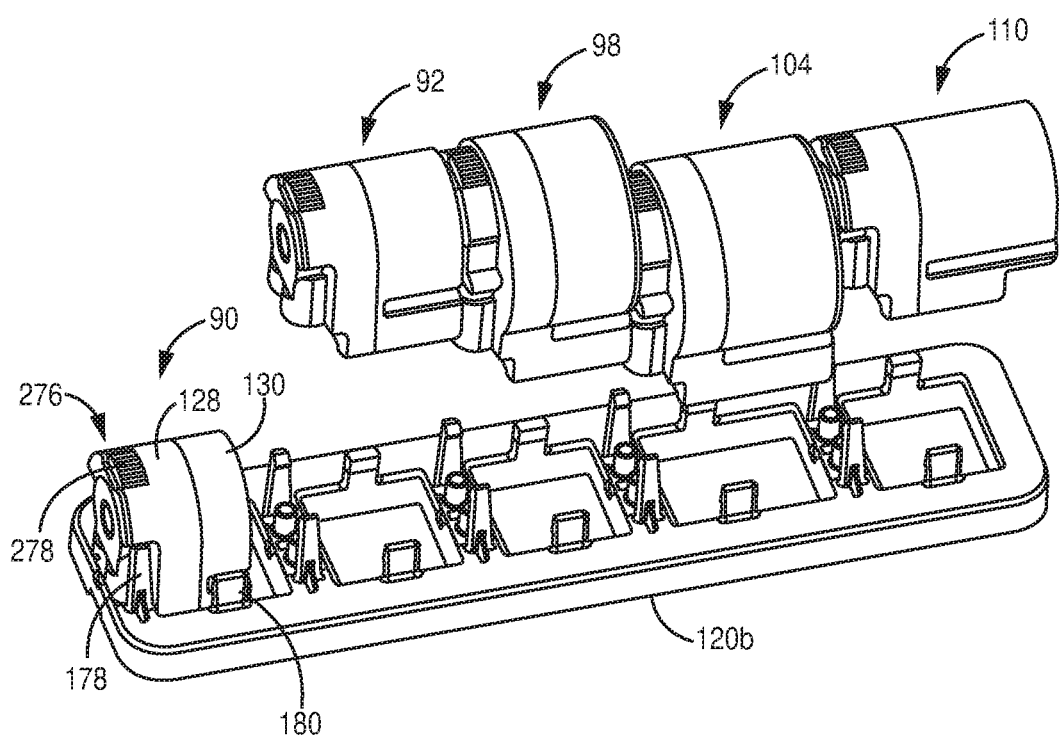

Module 90 is shown as fully mounted at docking station 166 in FIGS. 15G and 15H. As best seen in FIG. 15G, retainers 178a extend over shoulders 234 and engage with the top ledge 268 formed by shoulders 234 to prevent module 90 from moving upward away from docking station 166, thereby mechanically locking module 90 at docking station 166. Retainers 180a extend into grooves 236 to mechanically connect module 90 at docking station 166. As discussed above with regard to IR module 84, spring pins or other electrical connectors can extend through aperture 168 and engage baseboard 64 to provide electrical connections to module 90.

Module 90 can be removed by first unlocking module 90 from docking station 166. In the example shown, module 90 can be unlocked by activating release assembly 276, discussed in more detail below, to disengage retainers 178a from shoulders 234. The release assembly 276 engages the retainers 178a and causes long retainer arms 178 to flex outward, thereby widening the gap between retainers 178a. In the example shown, button 278 of release assembly 276 is depressed, thereby driving prongs 280 downwards into engagement with retainers 178a. The prongs 280 include sloped faces 282 that interface with the sloped faces 258 of retainers 178a and push retainers 178a away from module body 128 widening the gap between retainers 178a such that the bottom of each retainer 178a is no longer disposed over shoulders 230. With retainers 178a not disposed over shoulders 230, module 90 can be lifted upwards away from module carrier frame 120b. Retainers 180a include sloped lower side 272 and grooves 232 include sloped lower side 274 that are complimentary such that retainer 180a slides out of groove 232 due to the force exerted by pulling module 90 away from docking station 166. The lower side 274 of groove 232 engages and pushes against a lower side 272 of retainer 180a, causing short retainer arms 180 to flex and widen a gap between retainers 180a during removal. Module 90 is pulled upwards and away from module carrier frame 120b, breaking the mechanical, pneumatic, and electrical connections. A new module of the same or different type can then be inserted into the docking station 166.

Figure 16A:
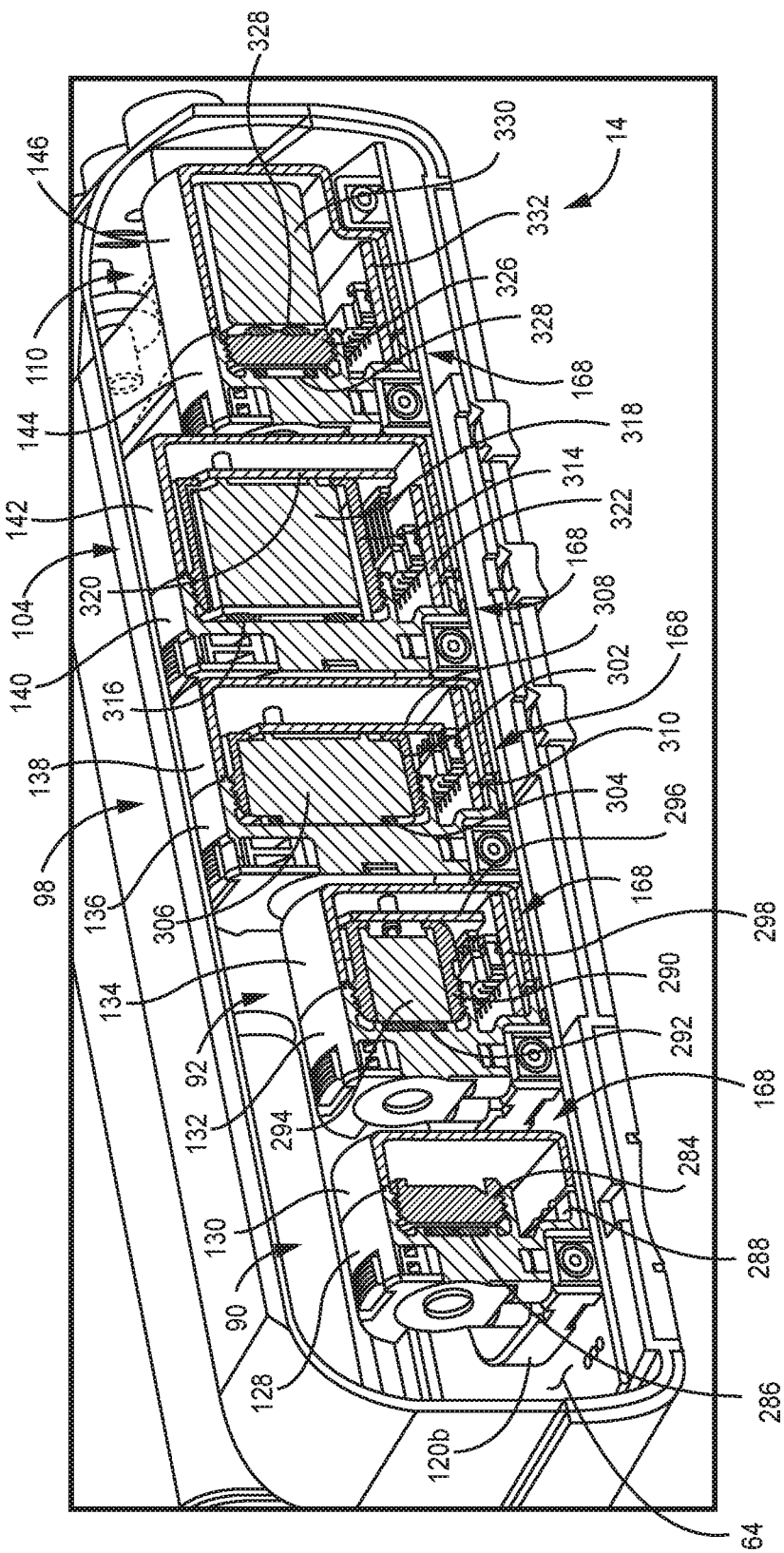
FIG. 16A is a sectional view of the portable gas analyzer in which five electrochemical modules are shown mounted on the second module carrier frame in session.
Figure 16B:
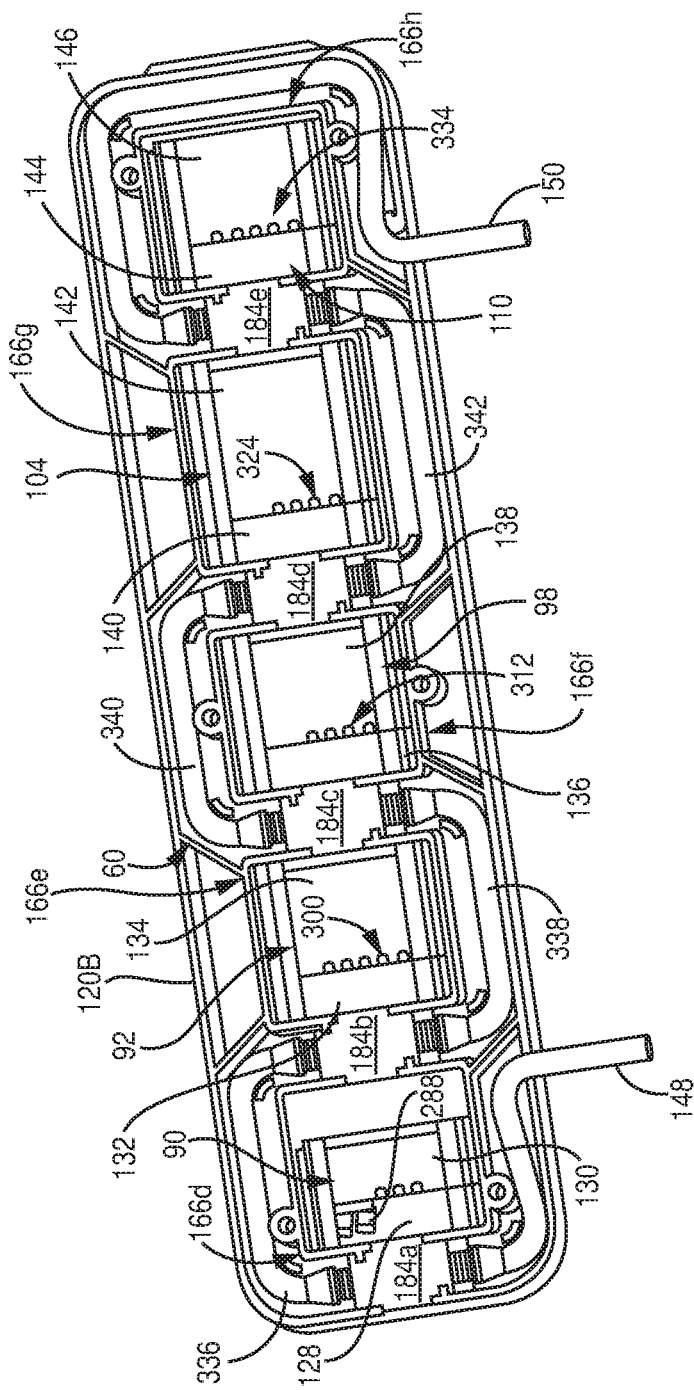
FIG. 16B is a bottom view of the second module carrier frame with all five modules inserted and with tubing and gas interconnects mounted in the carrier frame.

FIG. 16A is a cross-sectional view of gas analyzer 14 in which modules 90, 92, 98, 104, and 110 mounted on second module carrier frame 120b are shown in session. FIG. 16B is a bottom view of second module carrier frame 120b showing each of modules 90, 92, 98, 104, and 110 mounted on second module carrier frame 120b in session but with baseboard 64 removed for clarity.

A portion of pneumatic circuit 60 extends through second modular carrier frame 120b and provides gas to each module 90, 92, 98, 104, and 110 in series. Bypass module 90 includes module body 128, module cap 130, collar 284, seal 286, and contact pad 288. EC module 92 includes module body 132, cap 134, collar 290, seal 292, chemical cell 294, circuit board 296, circuit board 298, and spring pins 300. EC module 98 includes module body 136, cap 138, collar 302, seal 304, chemical cell 306, circuit board 308, circuit board 310, and spring pins 312. EC module 104 includes module body 140, cap 142, collar 314, seal 316, chemical cell 318, circuit board 320, circuit board 322, and spring pins 324. EC module 110 includes module body 144, cap 146, collar 326, seal 328, chemical cell 330, circuit board 332, and spring pins 334. Each of chemical cells 294, 306, 318, and 330 can also be referred to as the sensor or sensing component of each of EC modules 92, 98, 104, and 110, respectively. Chemical cells 294, 306, 318, 330 can respectively form the transducers 96, 102, 108, 110 of EC modules 92, 98, 104, 110.

Bypass module 90 is mounted at docking station 166d. The base of bypass module 90, which can be formed by the bottom portions of module body 128 and module cap 130, is disposed in the aperture 168 of docking station 166d. EC module 92 is disposed in docking station 166e. The base of EC module 92, which can be formed by the bottom portions of module body 132 and module cap 134, is disposed in the aperture 168 of docking station 166e. EC module 98 is disposed in docking station 166f. The base of EC module 98, which can be formed by the bottom portions of module body 136 and module cap 138, is disposed in the aperture 168 of docking station 166f. EC module 104 is disposed in docking station 166g. The base of EC module 104, which can be formed by the bottom portions of module body 140 and module cap 142, is disposed in the aperture 168 of docking station 166g. EC module 110 is disposed in docking station 166h. The base of EC module 110, which can be formed by the bottom portions of module body 144 and module cap 146, is disposed in the aperture 168 of docking station 166h.

Bypass module 90 is shown mounted in docking station 166d, but it is understood that bypass module 90 can be mounted at any desired docking station 166. For bypass module 90, cap 130 is attached to module body 128. Collar 284 is attached to module body 128 and encloses the flowpath through module body 128 that the gas flows through. In the example shown, collar 284 mounts to module body 128 via interfaced threading. Seal 286 is disposed between collar 284 and module body 128 and prevents gasses from leaking around collar 284. Bypass module 90 is configured to provide a pass-through for gas to continue to flow through pneumatic circuit, but bypass module 90 does not include any sensing components. Contact pad 288 extends from a bottom of bypass module 90 and is configured to contact baseboard 64. Contact pad 288 identifies bypass module 90 to analyzer controller 50 as a bypass module. As such, analyzer controller 50 can determine that a module is located at docking station 166d, such that the pneumatic circuit 60 is closed and gas will not leak from pneumatic circuit 60 into gas analyzer 14, and can further determine that the module mounted at docking station 166d is a bypass module.

EC module 92 is shown mounted in docking station 166e, but it is understood that EC module 92 can be mounted at any desired docking station 166. For EC module 92, cap 134 is attached to module body 132. Circuit boards 296, 298 are disposed within EC module 92 and enclosed by cap 134. Collar 290 mounts to module body 132 and chemical cell 294 is disposed within collar 290 and positioned to receive gas flowing through the flowpath within module body 132. In the example shown, collar 290 mounts to module body 132 by interfaced threading. Seal 292 is disposed at the interface between chemical cell 294 and module body 132. Threading collar 290 onto module body 132 captures seal 292 between chemical cell 294 and module body 132. Seal 292 prevents any gas in the flowpath through module body 132 from leaking around chemical cell 294.

Circuit board 296 is connected to chemical cell 294 to receive signals from chemical cell 294. Circuit board 296 can be an amplifier board configured to amplify the signal generated by chemical cell 294. Circuit board 296 is electrically connected to circuit board 298 for both power and data communications. Circuit board 298 is disposed below chemical cell 294 and a controller, such as a microprocessor, of EC module 92 can be disposed on circuit board 298. Spring pins 300 extend from circuit board 298 through the interface between module body 132 and cap 134 and contact baseboard 64. Spring pins 300 electrically connect EC module 92 to baseboard 64. A subset of spring pins 300 receive power from baseboard 64 to power EC module 92 and a second subset of spring pins 300 provide two-way data communications for EC module 92, such that EC module 92 can both receive and transmit data.

EC module 98 is shown mounted in docking station 166f, but it is understood that EC module 98 can be mounted at any desired docking station 166. For EC module 98, which can be a series 4 module, cap 138 is attached to module body 136. Circuit boards 308, 310 are disposed within EC module 98 and enclosed by cap 138. Collar 302 mounts to module body 136 and chemical cell 306 is disposed within collar 302 and positioned to receive gas flowing through the flowpath within module body 136. In the example shown, collar 302 mounts to module body 136 by interfaced threading. Seal 304 is disposed at the interface between chemical cell 306 and module body 136. Threading collar 302 onto module body 136 captures seal 304 between chemical cell 306 and module body 136. Seal 304 prevents any gas in the flowpath through module body 136 from leaking around chemical cell 306.

Circuit board 308 is connected to chemical cell 306 to receive signals from chemical cell 306. Circuit board 308 can be an amplifier board configured to amplify the signal generated by chemical cell 306. Circuit board 308 is electrically connected to circuit board 310 for both power and data communications. Circuit board 310 is disposed below chemical cell 306 and a controller, such as a microprocessor, of EC module 98 can be disposed on circuit board 310. Spring pins 312 extend from circuit board 310 through the interface between module body 136 and cap 138 and contact baseboard 64. Spring pins 312 electrically connect EC module 98 to baseboard 64. A subset of spring pins 312 receive power from baseboard 64 to power EC module 98 and a second subset of spring pins 312 provide two-way data communications for EC module 98, such that EC module 98 can both receive and transmit data.

EC module 104 is shown mounted in docking station 166g. Docking station 166g is sized larger than other docking stations to accommodate the larger length of EC module 104 as compared to modules 90, 92, 98, and 110. However, docking station 166g can also receive other modules smaller than EC module 104, such as bypass module 90 and EC modules 92 and 98. For EC module 104, which can be a series 5 module, cap 142 is attached to module body 140. Circuit boards 320, 322 are disposed within EC module 104 and enclosed by cap 142. Collar 314 mounts to module body 140 and chemical cell 318 is disposed within collar 314 and positioned to receive gas flowing through the flowpath within module body 140. In the example shown, collar 314 mounts to module body 140 by interfaced threading. Seal 316 is disposed at the interface between chemical cell 318 and module body 140. Threading collar 314 onto module body 140 captures seal 316 between chemical cell 318 and module body 140. Seal 316 prevents any gas in the flowpath through module body 140 from leaking around chemical cell 318.

Circuit board 320 is connected to chemical cell 318 to receive signals from chemical cell 318. Circuit board 320 can be an amplifier board configured to amplify the signal generated by chemical cell 318. Circuit board 320 is electrically connected to circuit board 322 for both power and data communications. Circuit board 322 is disposed below chemical cell 318 and a controller, such as a microprocessor, of EC module 104 can be disposed on circuit board 322. Spring pins 324 extend from circuit board 322 through the interface between module body 140 and cap 142 and contact baseboard 64. Spring pins 324 electrically connect EC module 104 to baseboard 64. A subset of spring pins 324 receive power from baseboard 64 to power EC module 104 and a second subset of spring pins 324 provide two-way data communications for EC module 104, such that EC module 104 can both receive and transmit data.

EC module 110 is shown mounted in docking station 166h. For EC module 110, which can be an oxygen sensor, cap 146 is attached to module body 144. Oxygen sensors are typically mounted at the last serial location along the pneumatic flowpath through gas analyzer 14. Circuit board 332 is disposed within EC module 110 and enclosed by cap 146. Collar 326 mounts to module body 144 and chemical cell 330 is attached to collar 326 and positioned to receive gas flowing through the flowpath within module body 144. In the example shown, collar 326 mounts to module body 144 by interfaced threading. A first one of seals 328 is disposed at the interface between collar 326 and module body 144 and a second one of seals 328 is disposed at an interface between collar 326 and chemical cell 330. Threading collar 326 onto module body 144 captures seal 328 between collar 326 and module body 144. Seals 328 prevents any gas in the flowpath through module body 144 from leaking out of that flowpath.

Circuit board 332 is disposed below chemical cell 330 and is electrically connected to chemical cell 330 to receive signals from chemical cell 330. A controller, such as a microprocessor, of EC module 110 can be disposed on circuit board 332. Spring pins 334 extend from circuit board 332 through the interface between module body 144 and cap 146 and contact baseboard 64. Spring pins 334 electrically connect EC module 110 to baseboard 64. A subset of spring pins 334 receive power from baseboard 64 to power EC module 110 and a second subset of spring pins 334 provide two-way data communications for EC module 110, such that EC module 110 can both receive and transmit data.

Gas enters pneumatic circuit 60 via inlet tube 148 and flows to a first one of gas interconnects 184a. The gas enters bypass module 90, flows through the flowpath in module body 128 and exits bypass module 90 to gas interconnect 184a.

The gas flows downstream from gas interconnect 184*a* through tube 336 to gas interconnect 184*b* where the gas enters EC module 92. The gas flows through the flowpath in module body 132 and chemical cell 294 generates data regarding the gas, such as the concentration of certain molecules and elements. Circuit board 296 amplifies the signal and the controller on circuit board 298 generates an output and can communicate data regarding the gas to the analyzer controller 50. The data can be provided to the user from EC module 92 via spring pins 300, baseboard 64, and user interface 42. The gas exits EC module 92 back to gas interconnect 184*b*.

The gas flows downstream from gas interconnect 184*b* through tube 338 to gas interconnect 184*c* where the gas enters EC module 98. The gas flows through the flowpath in module body 136 and chemical cell 306 generates data regarding the gas. Circuit board 308 amplifies the signal and the controller on circuit board 310 generates an output and can communicate data regarding the gas to the user via spring pins 312, baseboard 64, and user interface 42. The gas exits EC module 98 back to gas interconnect 184*c*.

The gas flows downstream through from gas interconnect 184*c* through tube 340 to gas interconnect 184*d* where the gas enters EC module 104. The gas flows through the flowpath in module body 140 and chemical cell 318 generates data regarding the gas. Circuit board 320 amplifies the signal and the microprocessor on circuit board 322 generates an output and can communicate data regarding the gas to the user via spring pins 324, baseboard 64, and user interface 42. The gas exits EC module 104 back to gas interconnect 184*d*.

The gas flows downstream from gas interconnect 184*d* through tube 342 to gas interconnect 184*e* where the gas enters EC module 110. The gas flows through the flowpath in module body 144 and chemical cell 330 generates data regarding the gas. The controller on circuit board 322 receives data from chemical cell 330, generates an output, and can communicate data regarding the gas to the user via spring pins 334, baseboard 64, and user interface 42. The gas exits EC module 110 back to gas interconnect 184*e*. The gas flows downstream from gas interconnect 184*e* through exhaust tube 150 and exits the portion of pneumatic circuit 60 associated with module carrier frame 120*b*.

Figure 17A:
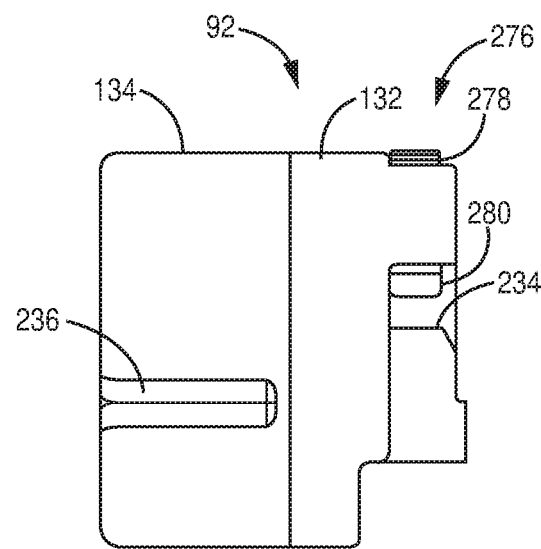
Figure 17B:
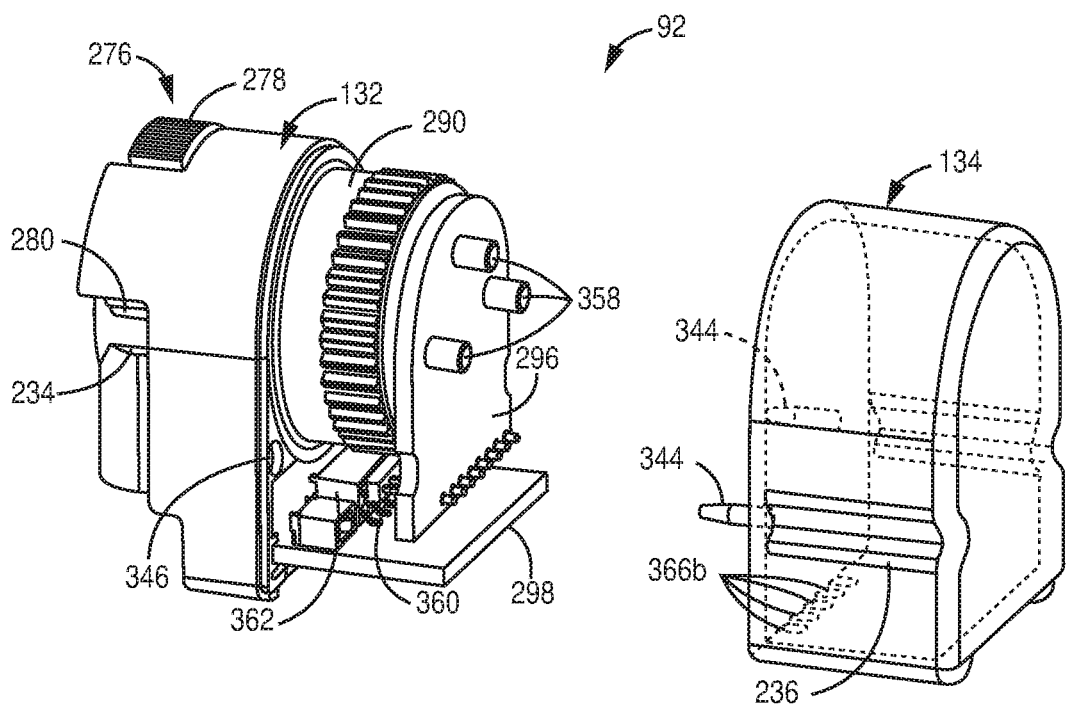
Figure 17C:
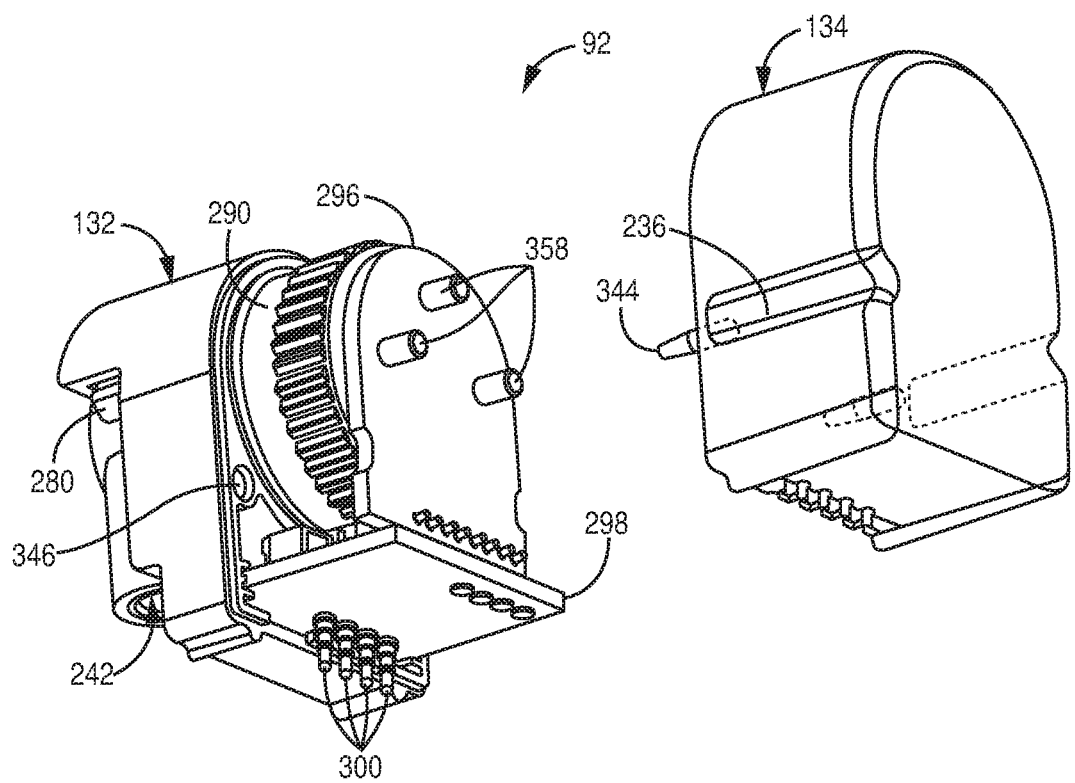
Figure 17D:
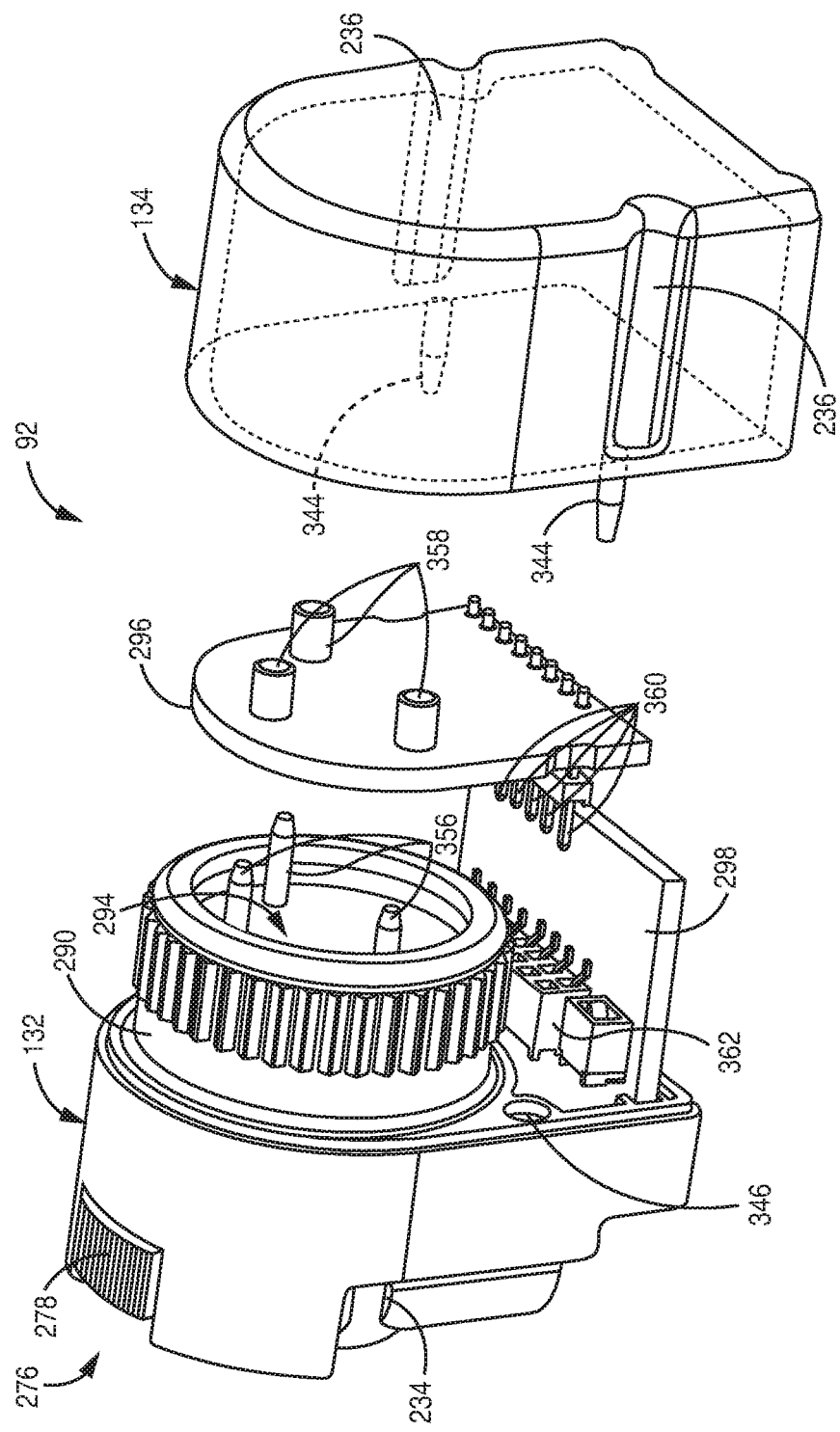
Figure 17E:
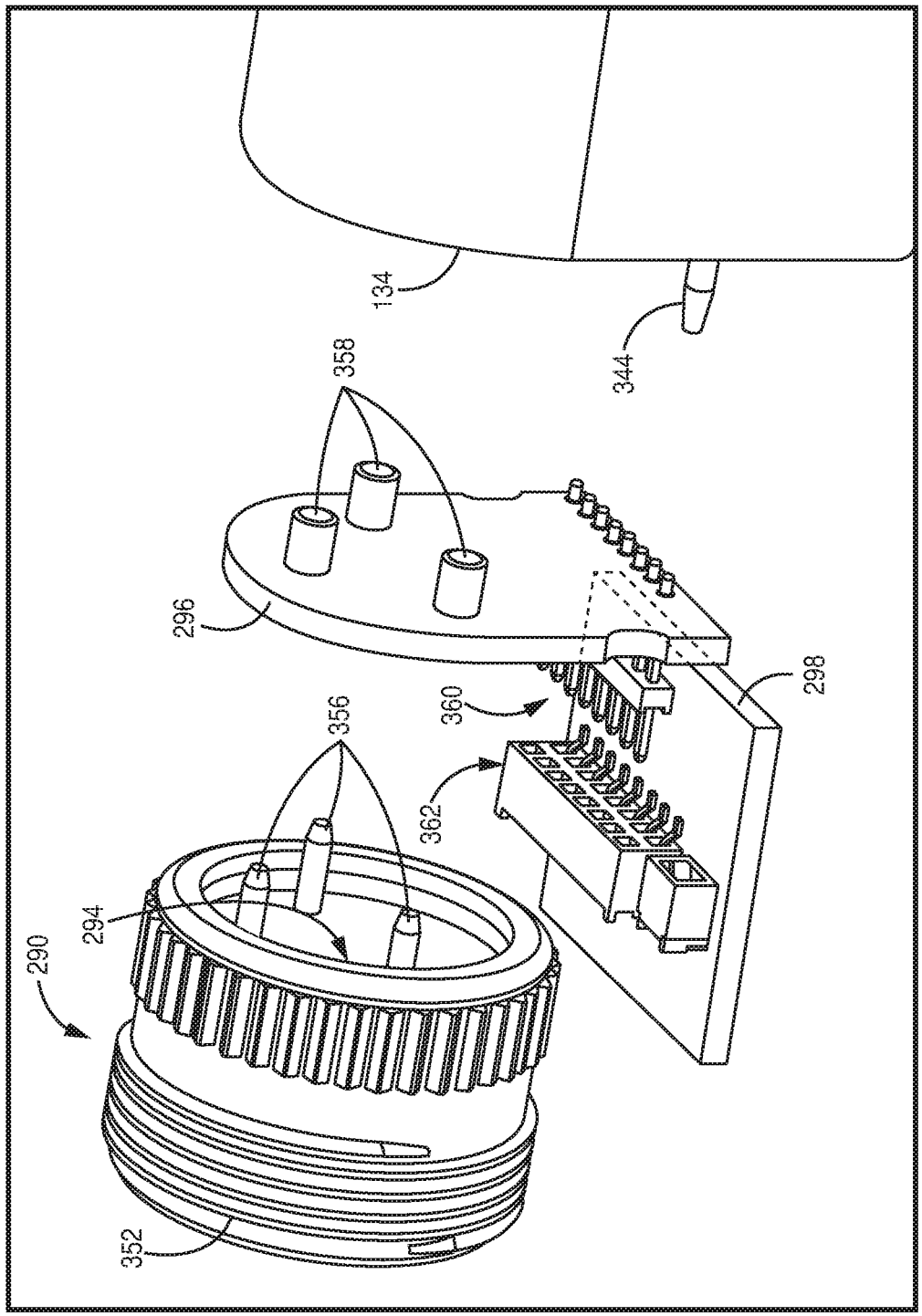
Figure 17F:
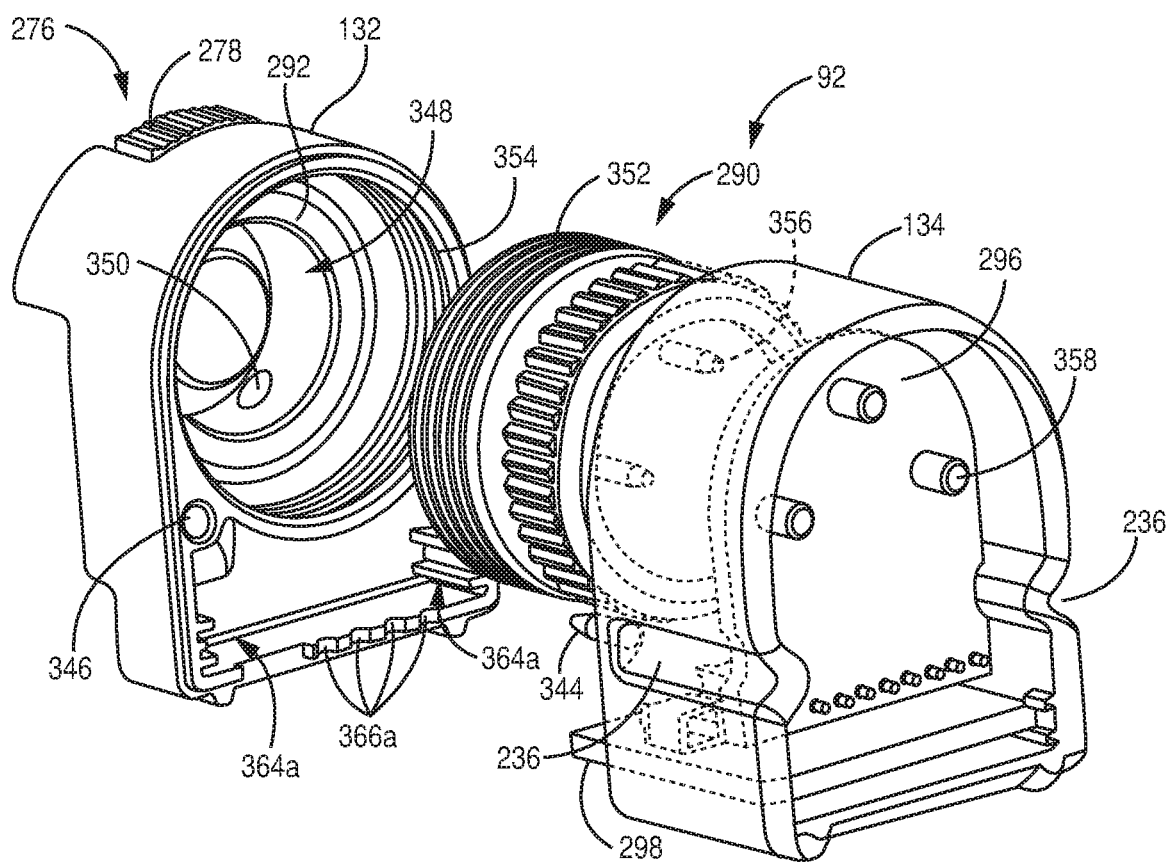
Figure 17H:
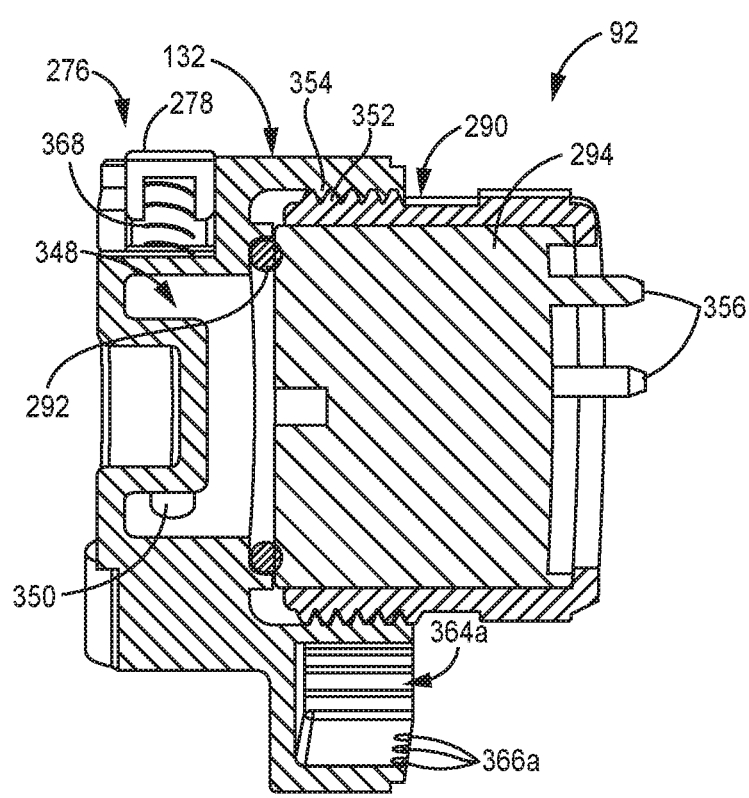
FIG. 17H is a cross-sectional view of the assembled module.

FIGS. 17A-17G are a series of exploded views of EC module 92, and FIG. 17H is a cross-sectional view of EC module 92 with cap 134 and circuit boards 296, 298 removed. The assembly of EC module 92 is substantially similar to that of bypass module 90, except bypass module 90 does not include circuit boards or a chemical cell. The assembly of EC module 92 is substantially similar to that of EC modules 98, 104, 110 except components of the various EC modules 92, 98, 104, 110 are sized differently and can be configured to generate data regarding different parameters and/or different gasses.

Cap 134 is mounted to module body 132 by posts 344 extending from cap 134 into bores 346 in module body 132. Grooves 236 are formed on cap 134. Shoulders 234 are formed on module body 132. Shoulders 234 and grooves 236 can be considered as forming a receiving portion of EC module 92 to mechanically connect EC module 92 to a carrier frame 120*a*-120*c*. Flowpath 348 within module body 132 is shown. Port 350 is an opening of one of the receiving openings 242 that provides fluid communication between the receiving opening and flowpath 348 to allow gas to flow into or out of flowpath 348. A second port 350 (not shown) provides another opening for the gas to flow into or out of flowpath 348. Either one of the ports 350 can provide the inlet port for gas to enter flowpath 348 while the other one of ports 350 provides the outlet port for the gas to exit flowpath 348. Which port 350 is the inlet and which port 350 is the outlet depends on the docking station 166 that EC module 92 is mounted at.

Seal 292 is disposed within module body 132 and is configured to interface with chemical cell 294 to seal flowpath 348. Chemical cell 294 is disposed in and supported by collar 290. Collar 290 includes external threading 352 configured to mate with internal threading 354 in module body 132 to secure chemical cell 294 to module body 132 and position chemical cell 294 relative to flowpath 348. Threading collar 290 into module body 132 secures seal 292 between chemical cell 294 and module body 132 to seal flowpath 348.

Pins 356 extend from a back end of chemical cell 294 and are received by receptacles 358 mounted to circuit board 296. Pins 356 and receptacles 358 provide the electric power and communications connection between chemical cell 294 and circuit board 296. The interfaced threading between collar 290 and module body 132 is clocked such that pins 356 are aligned with receptacles 358 when chemical cell 294 is installed in module body 132. Pins 360 extend from circuit board 296 and are received by connector 362 on circuit board 298.

Spring pins 300 extend from circuit board 298 and are configured to connect to baseboard 64 to provide both power and communications for EC module 92. The controller of EC module 92, such as a microcontroller, can be disposed on circuit board 298. The programmable module circuitry 94 can be considered as disposed across circuit boards 296, 298. Circuit board 298 is supported by slots 364*a* formed on opposite lateral sides in module body 132 and slots 364*b* formed on opposite lateral sides in cap 134. In some examples, two of spring pins 300 are power pins and two of spring pins 300 are communications pins. In some examples, one of the communications spring pins 300 is configured to transmit and the other is configured to receive. Notches 366*a* are formed in a base of module body 132 and notches 366*b* are formed in a base of cap 134. With cap 134 connected to module body 132, notches 366*a*, 366*b* form openings through which spring pins 300 extend to project out of EC module 92 and contact baseboard 64.

Release assembly 276 is mounted to module body 132. Button 278 is exposed at a top of module body 132 and is configured to be depressed by the user to break the mechanical connection between EC module 92 and long arms 178. Prongs 280 are disposed on opposite lateral sides of module body 132 and are connected to button 278 such that depressing button 278 causes prongs 280 to shift downward and engage retainers 178*a* of long arms 178 to drive retainers 178*a* away from module body 132 and disengage long arms 178 from shoulders 234. Release spring 368 is disposed below button 278 between button 278 and module body 132. Release spring 368 is configured to return release assembly 276 to its normal position after the downward force activating release assembly 276 is removed from button 278.

Figure 18A:
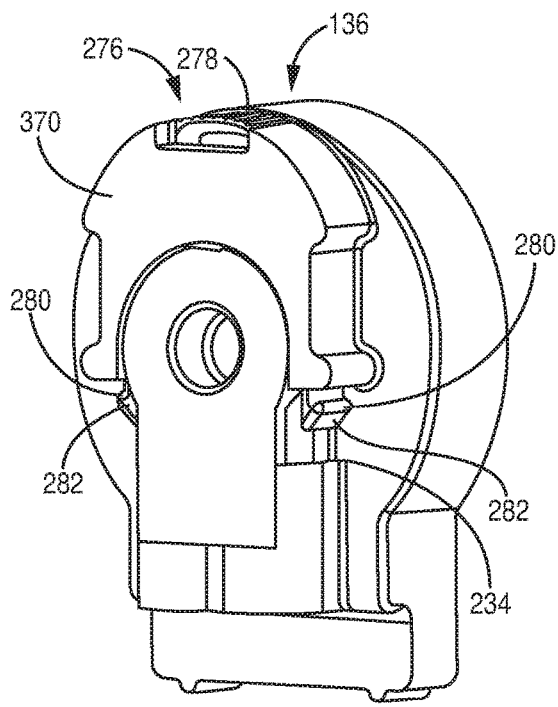
FIG. 18A is an isometric view of a module body assembly with a button release mechanism.
Figure 18B:
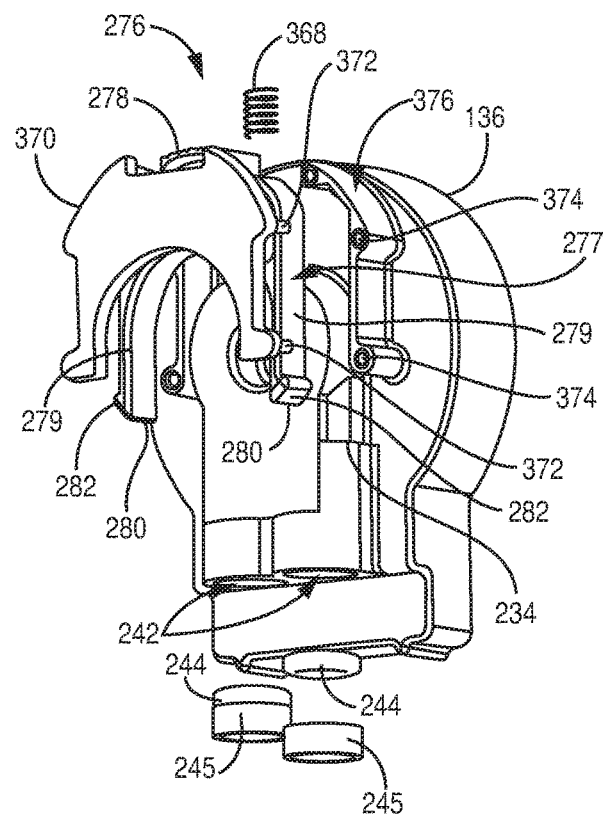
FIG. 18B is an exploded view of the module body assembly of FIG. 18A showing the button release mechanism.
Figure 18C:
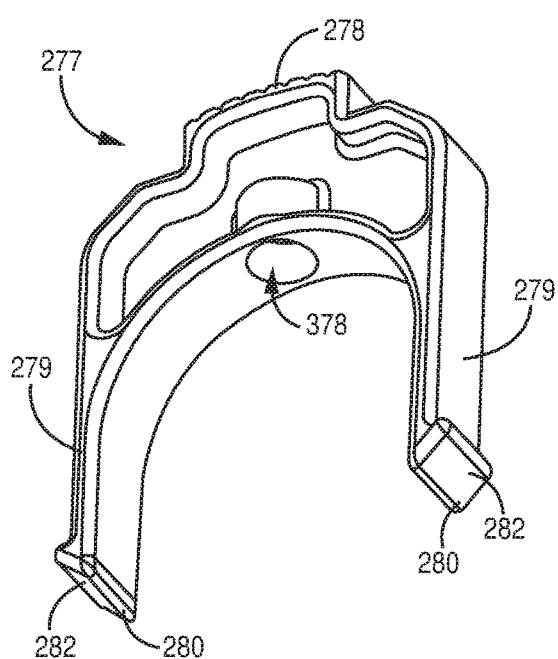
FIG. 18C is an isometric view of a release mechanism.

FIG. 18A is an isometric view of module body 136 with release assembly 276. FIG. 18B is an exploded view of module body 136 and release assembly 276. FIG. 18C is an isometric view of release mechanism 277 from a bottom of release mechanism 277. While release assembly 276 is discussed with regard to module body 136, it is understood that release assembly 276 is substantially similar across each module 84, 90, 92, 98, 104, 110.

Mechanism cap 370 connects to module body 136 and secures release assembly 276 to module body 136. Mechanism cap 370 includes posts 372 configured to extend into openings 374 formed in module body 136. In the example shown, button 278, prong arms 279, and prongs 280 of release mechanism 277 are integrally formed as a single inverted U-shaped part. Prong arms 279 extend vertically downward and prongs 280 are disposed at the distal ends of prong arms 279. Prong arms 279 are disposed between a portion of module body 136 and brackets 376 and are covered by brackets 376 extending from module body 136. Openings 374 are formed in brackets 376. Prongs 280 include sloped faces 282 configured engage with retaining portions 178a of long arms 178 to disengage long arms 178 from shoulders 234, thereby unlocking the module from the carrier frame. It is understood, however, that prongs 280 can be of any desired configuration suitable for disengaging retaining portions 178a from shoulders 234. Release spring 368 is disposed below button 278 between button 278 and module body 136. Release spring 368 extends into spring bore 378 formed in release mechanism 277 opposite button 278. Release spring 368 is configured to return release assembly 276 to its normal position after the downward force activating release assembly 276 is removed from button 278. O-rings 244 and o-ring retainers 245 are also shown. O-rings 244 and o-ring retainers 245 are disposed in receiving openings 242. O-ring retainers 245 secure o-rings 244 within receiving openings 242.

Figure 19A:
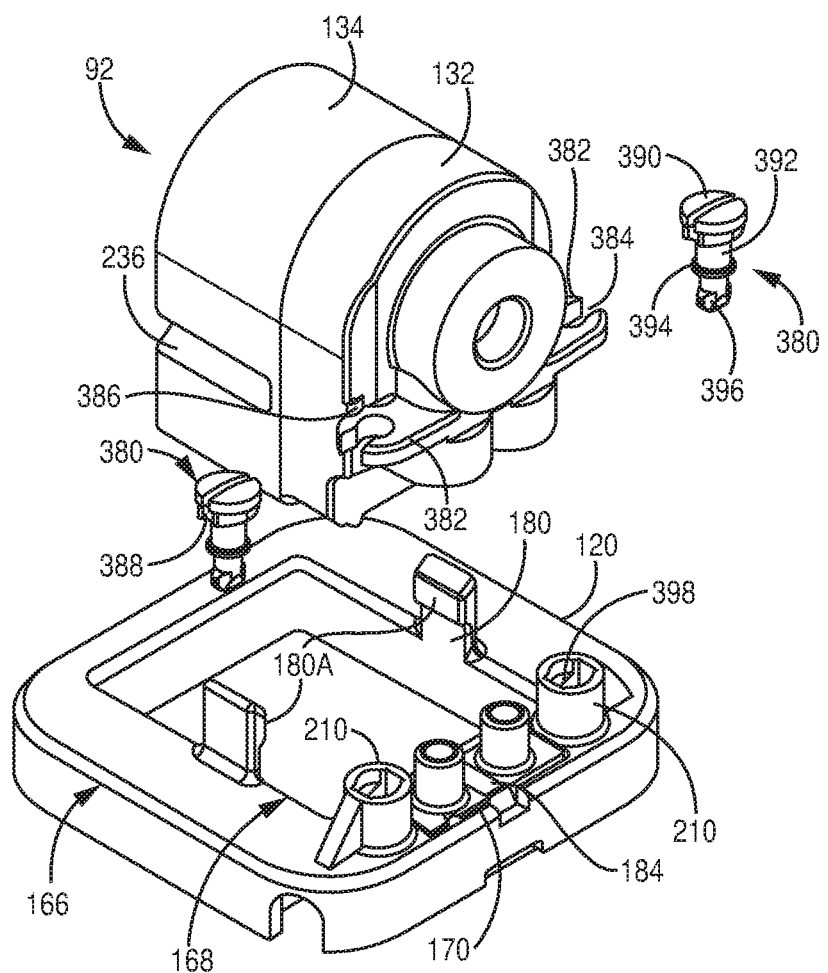
FIG. 19A is an exploded view of a module, module carrier frame, and fastener.
Figure 19B:
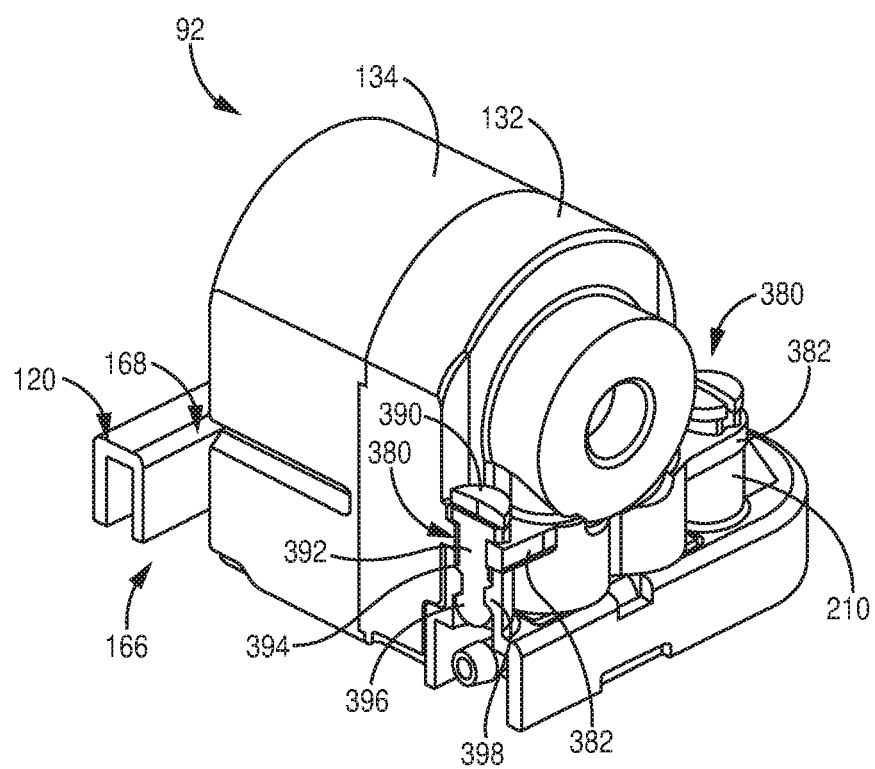
FIG. 19B is a cross-sectional view showing the module mounted to the module carrier frame.
Figure 19C:
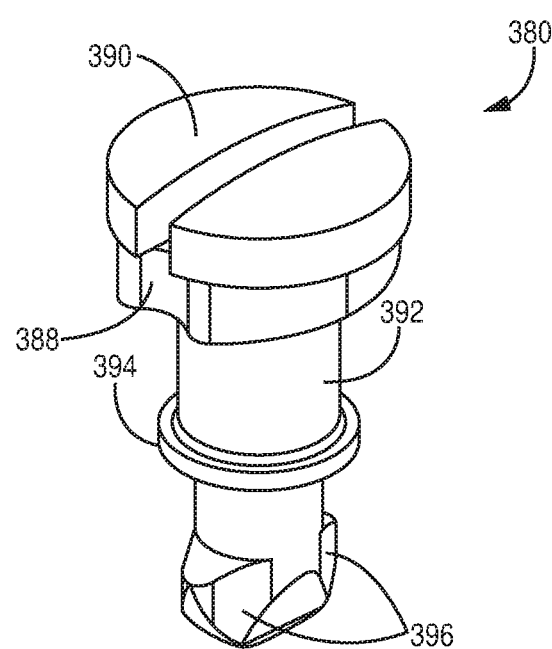
FIG. 19C is an isometric view of a fastener.

FIG. 19A is an exploded view of module 92 and a docking station 166 of a carrier frame 120. FIG. 19B is a cross-sectional view showing module 92 mounted to carrier frame 120. FIG. 19C is an isometric view of fastener 380. FIGS. 19A-19C are discussed together. While the locking assembly shown in FIGS. 19A-19C is discussed with regard to module 92, it is understood that the discussion is equally applicable to each of modules 84, 90, 92, 98, 104, 110.

Carrier frame 120 includes module receiving aperture 168, gas interconnect aperture 170, short arms 180, and fastener posts 210. Gas interconnect 184 is mounted in aperture 170. Short arms 180 include retainers 180a configured to engage groove 236 formed on cap 134. Fastener mounts 382 project laterally from module body 132 and are configured to receive fasteners 380. Fastener mounts 382 do not extend fully around the opening that the fastener 380 is disposed in when module 92 is mounted to carrier frame 120. Fastener mounts 382 include lateral openings 384 to allow fasteners 380 to slide laterally into fastener mounts 382. Module body 132 includes detents 386 configured to engage with notches 388 formed on fasteners 380. Detent 386 engaging notch 388 indicates that fastener 380 is in a locked position, locking module 92 to carrier frame 120.

Fastener 380 includes head 390, shank 392, flange 394, and projections 396. Notch 388 is formed on head 390. Shank 392 extends between head 390 and projections 396. Flange 394 extends radially from shank 392. With fasteners disposed in fastener mounts 382, head 390 is disposed on a first side of fastener mount 382 and shank 392 passes through fastener mount 382. Projections 396 extend radially from the end of shank 392 disposed opposite head 390. Projections 396 extend the width of the end of fastener 380 and are configured to engage the bottom sides of projections 398 formed in fastener posts 210. With fastener 380 in the locked state (FIG. 19B), projections 396 are disposed on a lower side of projections 398 and flange 394 is disposed on an opposite side of projections 398. Projections 398 are not full rings and instead include circumferential gaps to allow projections 396 to pass between projections 398 when fastener 380 is in the unlocked state.

Figure 20A:
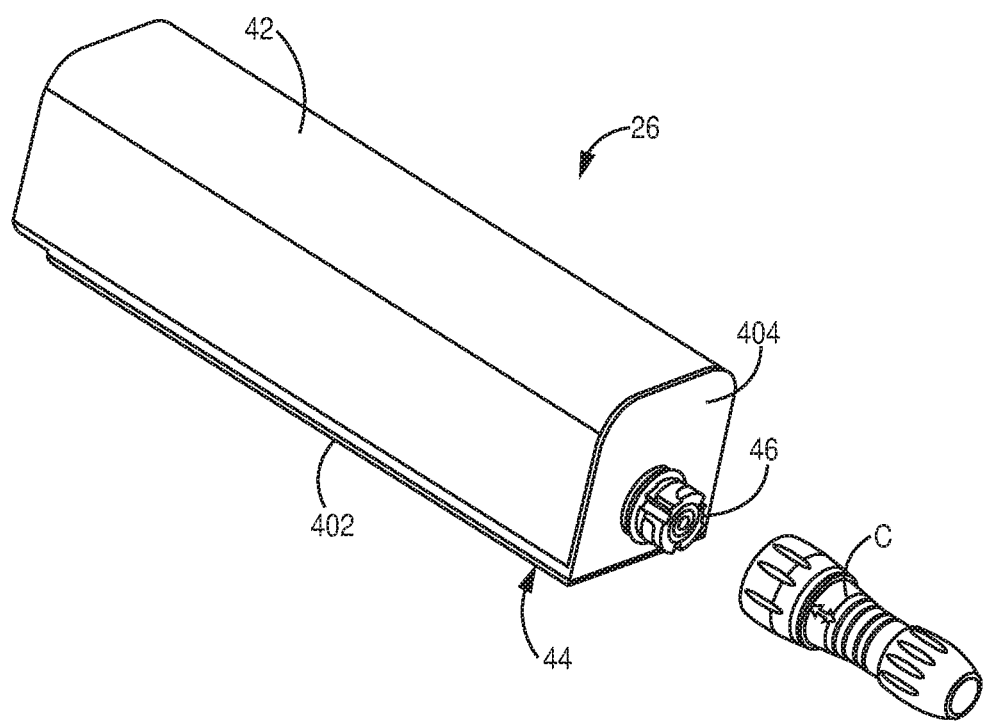
FIG. 20A is an isometric view from a top of a battery pack.
Figure 20B:
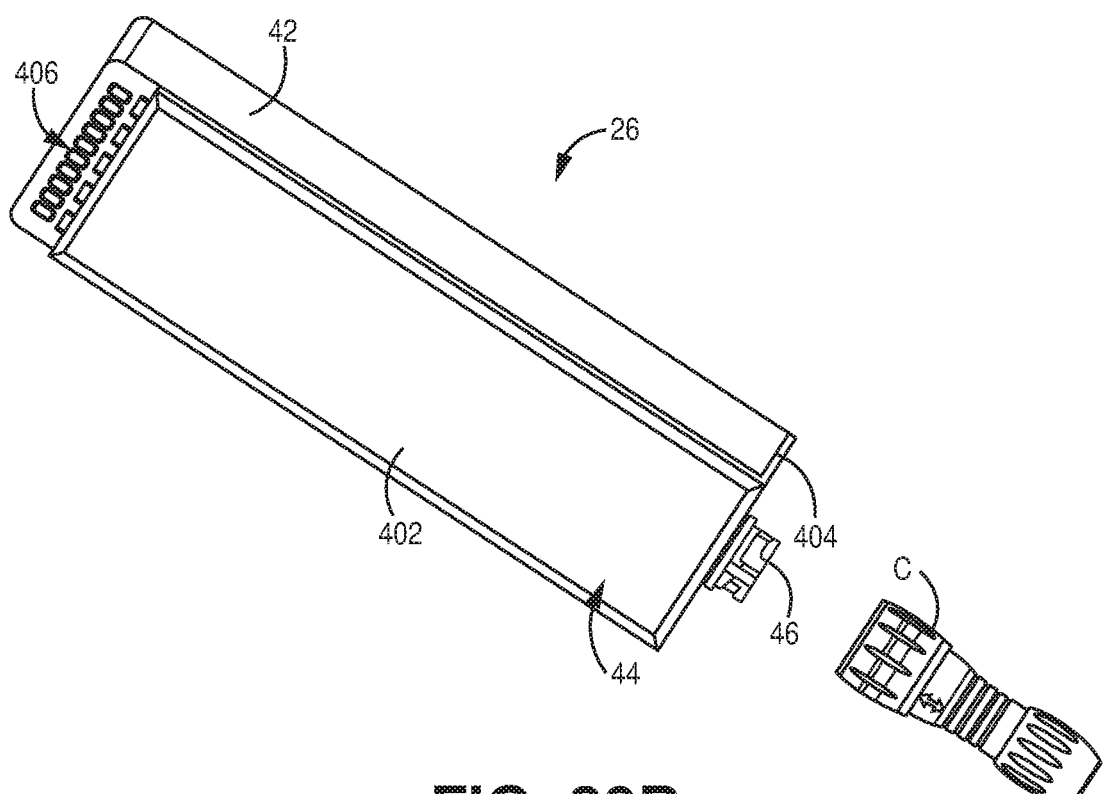
FIG. 20B is an isometric view from a bottom of the battery pack of FIG. 20A.
Figure 20C:
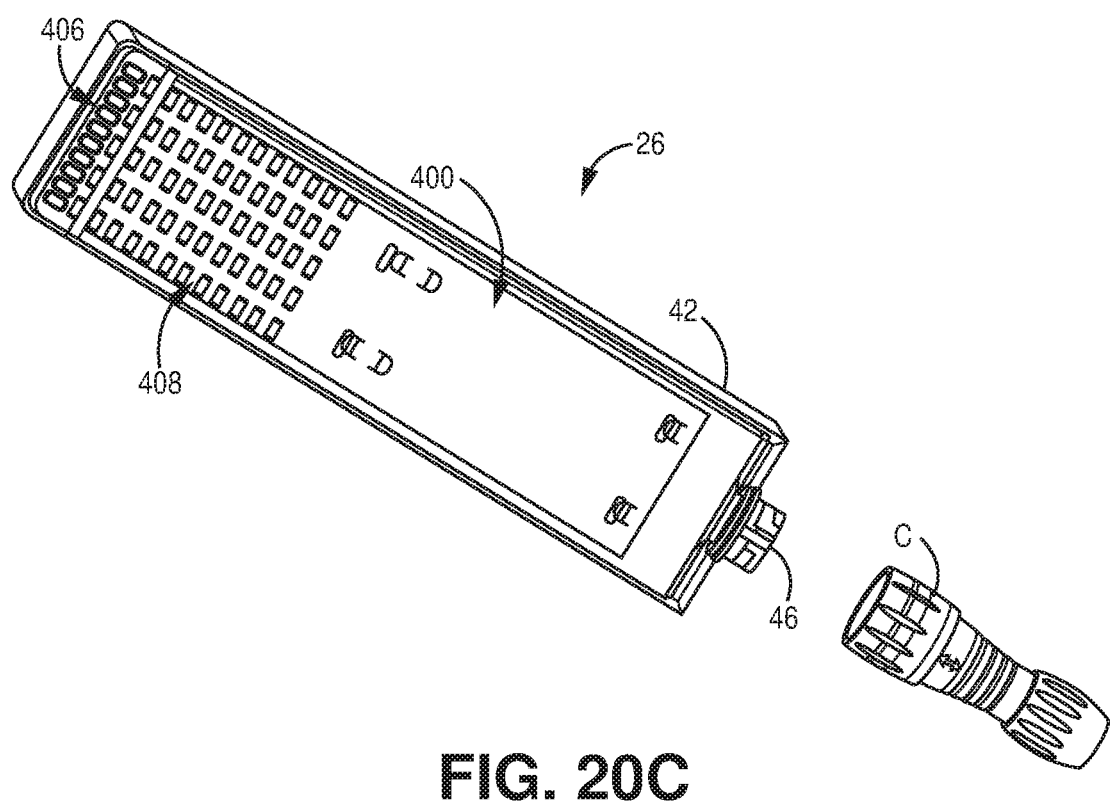
FIG. 20C is an isometric view from a bottom of the battery pack of FIG. 20A with a base of the battery pack removed to show the baseboard of the battery pack.

During mounting, fasteners 380 are shifted laterally onto fastener mounts 382. Module 92 is lowered onto docking station 166. Short retainer arms slide over lateral sides of cap 134 and retainers 180a snap into grooves 236. Retainers 180a engaging grooves 236 mechanically secures module 92 to carrier frame 120. As discussed above, pneumatic and electrical connections are formed simultaneously with the mechanical connection. Fasteners 380 extend into fastener posts 210 and projections 396 pass through the gaps between projections 398. Fastener 380 can be rotated such that projections 396 are disposed below projections 398, preventing fasteners 380 from being pulled out of posts 210. Fasteners 380 can thereby lock module 92 to carrier frame 120. Fasteners 380 can be rotated less than a full turn to lock module 92 to carrier frame 120. In some examples, fasteners 380 can be rotated a quarter turn between the locked and unlocked states. FIG. 20A is an isometric view from a top of battery pack 26. FIG. 20B is an isometric view from a bottom of battery pack 26. FIG. 20C is an isometric view from a bottom of battery pack 26 with a base 44 of battery pack 26 transparent to show circuit board 400 of battery pack 26.

Battery pack 26 is removably mountable to gas analyzer 14. Specifically, battery pack 26 can be mounted within and removed from slot 28a in gas analyzer 14. Battery case lid 42 is attached to battery base 44 and encloses the battery cells 48 within a compartment defined between battery case lid 42 and battery base 44. Battery case lid 42 can be permanently connected to base 44. Battery pack 26 is configured to remain as a unit and is not meant to be disassembled. Battery base 44 includes a longitudinal portion 402 and a vertical portion 404. Connector 46 extends through the vertical portion 404. Connector 46 is configured to attach to connector C to receive power from connector C to recharge the battery cells within battery pack 26.

Battery pack 26 electrically connects to baseboard 64 of gas analyzer 14 via contacts 406 to provide power to various components of gas analyzer 14. Circuit board 400 is disposed within the compartment between battery case lid 42 and battery base 44. Battery pack 26 provides power to gas analyzer 14 which can be utilized in hazardous locations where explosive gasses, such as methane, may be present. The power provided to baseboard 64 from battery pack 26 is limited by resistors 408 disposed on the circuit board 400 of battery pack 26 to facilitate use and replacement in hazardous locations. Battery pack 26 is configured to facilitate replacement of the battery pack 26 in hazardous location, such as a Zone 1 or Zone 2 locations. The resistors 408 are disposed on an opposite side of the circuit board 400 from the battery cells 48. Resistors 408 are disposed in series on the bottom side of circuit board 406. Resistors 408 are disposed on the side of circuit board 408 facing into the slot 28a towards the front side of gas analyzer 14. Resistors 408 can be soldered to circuit board 400.

Figure 21A:
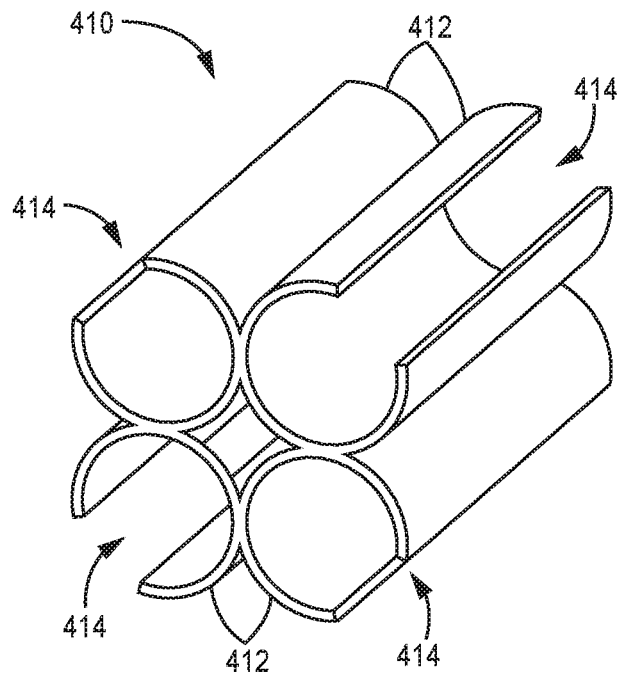
FIG. 21A is an isometric view of a battery support clip.
Figure 21B:
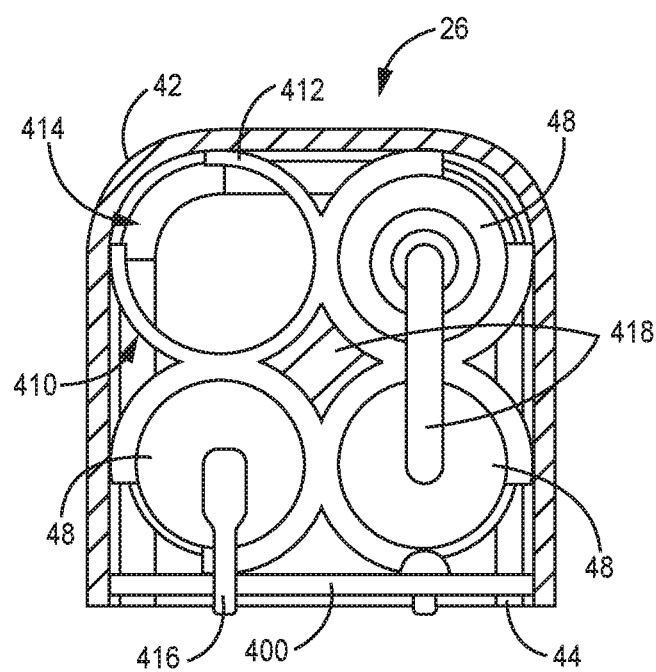
FIG. 21B is a cross-sectional view of a battery pack.

FIG. 21A is an isometric view of support clip 410. FIG. 21B is a cross-sectional view of battery pack 26 showing battery cells 48 retained within the support clip 410. Support clip 410 includes support cylinders 412. Each support cylinder 412 includes elongate opening 414 extending fully along a length of the support cylinder 412. Elongate openings 414 allow support cylinders 412 to flex to receive battery cells 48 such that cylinders 412 tightly hold battery cells 48 in place. Battery cells 48 are disposed in the cylinders 412 of support clip 410. The body of support clip 410 provides clearance between battery cells 48 mounted to support clip 410. As such, support clip 410 both holds battery cells 48 in place and maintains a desired clearance between battery cells 48, which are connected to circuit board 400. Connectors 416 extend from battery cells 48 to circuit board 400 to electrically connect battery cells 48 to circuit board 400. In some examples, individual ones of battery cells 48 are connected to other individual ones of battery cells 48, such as the top battery cells 48 being connected to the bottom battery cells 48 by connectors 418. While FIG. 21B shows three battery cells 48 mounted to support clip 410, it is understood that each support cylinder 412 can support a battery cell 48.

DISCUSSION OF POSSIBLE EMBODIMENTS

The following are non-exclusive descriptions of possible embodiments of the present invention.

A handheld gas analyzer including a housing; a gas inlet and a gas outlet; a plurality of internal bays within the housing; a plurality of gas sensor modules, wherein a first subset of the plurality of gas sensor modules are configured to mount in the plurality of bays; and an analyzer controller within the housing. The sensor modules include a transducer for measuring a respective gas property; and programmable module circuitry configured to process signal information from the transducer and output data. The analyzer controller is configured to receive the data output from the plurality of gas sensor modules.

The handheld gas analyzer of the preceding paragraph can optionally include, additionally and/or alternatively, any one or more of the following features, configurations and/or additional components:

The programmable circuitry of each of the plurality of gas sensor modules is configured to apply a different calibration factor, wherein the calibration factor is factory set based on a measured output from the transducer.

A common pneumatic circuit runs through each of the plurality of gas sensor modules.

The analyzer controller is configured to associated a first unique identifier with data output from a first module of the plurality of gas sensor modules, and wherein the analyzer controller is further configured to save the unique identifier in association with the data output from the first module to generate first associated sensor data.

The first unique identifier is stored in the programmable module circuitry of the first module.

The analyzer controller includes transmission circuitry configured to transmit the first associated sensor data to a remote computing device.

The analyzer controller is further configured to associate site data with the first associated sensor data, thereby generating sample-specific data.

A user interface configured to send information to the analyzer controller and receive information from the analyzer controller.

The analyzer controller is configured to receive a unique module identifier associated with a first module of the plurality of gas sensor modules via the user interface.

The analyzer controller is further configured to determine if a first unique module identifier associated with a first module of the plurality of gas sensor modules is stored on the programmable module circuitry of the first module.

The analyzer controller is further configured to provide a prompt to the user interface, the prompt requesting the first unique module identifier.

The user interface is integrated into the housing.

A second subset of the plurality of gas sensor modules disposed at least partially outside of the housing A first sensor module of the second subset of the plurality of gas sensor modules is disposed outside of the housing and connected to the analyzer controller via one of a wired communication link and a wireless communication link.

The first sensor module is a temperature sensor.

A first module of the first subset of the plurality of gas sensing modules includes a module housing; a pneumatic chamber; a first pneumatic port fluidly connected to the pneumatic chamber; a second pneumatic port fluidly connected to the pneumatic chamber; a first transducer disposed adjacent the pneumatic chamber; and an electric connector projecting from the gas sensing module. The gas sensing module is configured to form a pneumatic connection via the first and second pneumatic ports, a mechanical connection, and an electrical connection via the electrical connector by insertion of the first module into a first bay of the plurality of internal bays.

The electrical connection is formed between a baseboard of the handheld gas analyzer and the electrical connector The plurality of internal bays are formed in a module carrier frame disposed in the housing.

The mechanical connection is actuatable between a locked state, locking the module housing within the first bay, and an unlocked state, allowing removal of the module housing from the first bay.

A gas analyzer is configured to receive gas and generate data regarding the gas an includes a housing; a first sensor module connectable to the housing, the first sensor module configured to generate parameter data regarding a gas; and an analyzer controller configured to receive a first unique module identifier for the first sensor module; and associate the first unique module identifier with the parameter data generated by the first sensor module, thereby generating first associated parameter data.

The gas analyzer of the preceding paragraph can optionally include, additionally and/or alternatively, any one or more of the following features, configurations and/or additional components:

The analyzer controller is further configured to record the first associated parameter data.

The first unique module identifier is stored in a memory of the first sensor module.

The first sensor module is mounted at least partially within the housing of the gas analyzer.

The first sensor module is disposed within and enclosed by the housing.

A user interface configured to send information to the analyzer controller and receive information from the analyzer controller.

The analyzer controller is further configured to receive the first unique module identifier via the user interface.

The analyzer controller is further configured to determine if the first unique module identifier is stored on the first sensor module.

The analyzer controller is further configured to provide a prompt to the user interface, the prompt requesting the first unique module identifier.

The user interface is integrated into the housing.

The sensor module is disposed outside of the housing and connected to the analyzer controller via one of a wired communication link and a wireless communication link.

The first sensor module is a temperature sensor.

The analyzer controller is further configured to associate site data with the first associated parameter data, thereby generating sample-specific parameter data.

The site data includes temporal data.

A second sensor module configured to generate parameter data regarding the gas, wherein the second sensor module has a second unique module identifier. The analyzer controller is further configured to: receive the second unique module identifier for the second sensor module; and associate the second unique module identifier with the parameter data generated by the second sensor module, thereby generating second associated parameter data.

The analyzer controller includes transmission circuitry configured to transmit the first module-specific parameter data to a remote computing device.

A method includes detecting, by an analyzer controller of a gas analyzer, a first sensor module of the gas analyzer, the first sensor module configured to generate first parameter data regarding a gas received by the gas analyzer; receiving, by the analyzer controller, a first unique module identifier of the first sensor module; and associating, by the control circuitry, the first unique module identifier with the first parameter data generated by the first sensor module, thereby generating first associated parameter data.

The method of the preceding paragraph can optionally include, additionally and/or alternatively, any one or more of the following features, configurations and/or additional components:

Recalling the first unique module identifier from a memory of the first sensor module; and providing the first unique module identifier to the control circuitry.

Generating a prompt, by the analyzer controller, and sending the prompt to a user interface of the gas analyzer, wherein the prompt requests entry of the first unique module identifier to the gas analyzer.

Transmitting the first associated parameter data from the gas analyzer to a remote computing device.

A module assembly for a gas analyzer configured to receive gasses and generate data regarding the gasses includes a plurality of docking stations, wherein each docking station includes a pneumatic inlet and a pneumatic outlet; a plurality of gas sensing modules disposed within the plurality of docking stations; wherein a first gas sensing module of the plurality of gas sensing modules is mountable to the plurality of docking stations and a second gas sensing module of the plurality of gas sensing modules is mountable to the plurality of docking stations.

The module assembly of the preceding paragraph can optionally include, additionally and/or alternatively, any one or more of the following features, configurations and/or additional components:

The first gas sensing module is different than the second gas sensing module.

The first gas sensing module is removably mountable to any one of the plurality of docking stations.

The first gas sensing module includes a first base having a first length and a first docking station of the plurality of dockings stations includes a first module receiving aperture sized to receive the first base.

The second gas sensing module includes a second base having a second length, and wherein the first module receiving aperture is sized to receive the second base.

A third gas sensing module of the plurality of gas sensing modules, the third gas sensing module having a third base having a third length, the third length larger than either of the first length and the second length. The first module receiving aperture is sized to receive the third base.

A second docking station of the plurality of docking stations includes a second module receiving aperture, and the second module receiving aperture has an aperture length one of equal to and larger than the first length and the second length.

A pneumatic flowpath extends serially through the plurality of docking stations.

The first gas sensing module is an electrochemical sensor.

The first gas sensing module is an infrared gas sensor.

The first gas sensing module includes a first base configured to mount within a first docking station of the plurality of docking stations and further includes a second base configured to mount within a second docking station of the plurality of docking stations.

The first docking station is adjacent the second docking station.

At least one of the plurality of docking stations is disposed between the first docking station and the second docking station.

A first docking station of the plurality of docking stations includes a gas interconnect aperture disposed adjacent a module receiving aperture, and wherein the pneumatic inlet and the pneumatic outlet project from the gas interconnect aperture.

A gas interconnect is disposed in the gas interconnect aperture, the pneumatic inlet comprising a first post extending from the gas interconnect and the pneumatic outlet comprising a second post extending from the gas interconnect.

The first post is received in a first port formed in a housing of the first gas sensor to provide gas to the first gas sensor, and wherein the second post is received in a second port formed in the housing of the first gas sensor to receive gas from the first gas sensor.

A module carrier frame disposed within the gas analyzer, the module carrier frame defining the plurality of docking stations.

Pneumatic pathways are formed between adjacent ones of the plurality of docking stations to provide serial gas flow to the plurality of docking stations.

A gas sensing module for a gas analyzer includes a module housing; a pneumatic chamber; a sensing component disposed adjacent the pneumatic chamber and configured to generate information regarding gas within the pneumatic chamber; and an electric connector projecting from the gas sensing module. The gas sensing module is configured to form a pneumatic connection with the pneumatic chamber, a mechanical connection with the module housing, and an electrical connection via the electrical connector by mounting the gas sensing module.

The gas sensing module of the preceding paragraph can optionally include, additionally and/or alternatively, any one or more of the following features, configurations and/or additional components:

The electric connector is a spring pin.

The electrical connection is formed between a baseboard of the gas analyzer and the electrical connector.

The gas sensing module is mounted within a bay.

The pneumatic connection, the mechanical connection, and the electrical connection are simultaneously formed.

The gas sensing module is insertable by a single motion such that the pneumatic connection, the mechanical connection, and the electrical connection are formed by the single motion.

The gas sensing module is configured to mount to a module carrier frame disposed in the gas analyzer.

At least one arm extends from the module carrier frame and engages the housing to form the mechanical connection.

The at least one arm engages a shoulder formed on the housing.

The at least one arm engages a groove formed on the housing.

The at least one arm includes a first arm having a first length and a second arm having a second length shorter than the first length.

A fastener is configured to lock the gas sensing module to module carrier frame.

The fastener is configured to rotate less than a full rotation between a locked state and an unlocked state.

The module carrier frame includes an array of at least three bays, and wherein the gas sensing module is configured to mount within at least one of the at least three bays.

The electric connection includes a data connection.

Programmable module circuitry configured to transmit and receive data via the data connection.

The electric connection includes a power connection to provide power to the gas sensing module.

The pneumatic connection is formed by a prong extending into a receiver, the prong extends into the receive upon mounting of the gas sensing module.

A first pneumatic port extending into the housing and fluidly connected to the pneumatic chamber, wherein the first pneumatic port is configured to receive the prong.

A handheld gas analyzer including an analyzer housing, a module carrier frame disposed within the analyzer housing, and a plurality of gas sensing modules mountable to the module carrier frame. A first one of the plurality of gas sensing modules is the gas sensing module.

The module carrier frame is a single component formed from a plastic and defining a plurality of bays configured to receive the plurality of gas sensing modules.

A pneumatic pathway extends between the plurality of bays.

The pneumatic pathway is defined at least in part by the module carrier frame.

The pneumatic pathway is defined at least in part by flexible tubing extending between individual ones of the plurality of bays.

The electrical connection is formed at least partially through the module carrier frame.

A method of mounting a gas sensing module within a gas analyzer includes inserting a housing of the gas sensing module into a docking station disposed within the gas analyzer. Inserting the housing into the docking station establishes electrical, pneumatic, and mechanical connections between the gas sensing module and the gas analyzer.

The method of the preceding paragraph can optionally include, additionally and/or alternatively, any one or more of the following features, configurations and/or additional components:

The electrical connection is established by electrical contacts of the gas sensing module contacting a baseboard of the gas analyzer.

Establishing the electrical connection includes making a power connection between the gas sensing module and a power source of the gas analyzer.

Establishing the electrical connection further includes making a data communications connection between the gas sensing module and a controller of the gas analyzer.

The data communications connection is between a programmable module circuitry disposed in the housing of the gas sensing module and the controller of the gas analyzer.

Establishing the pneumatic connection includes inserting connecting posts into pneumatic ports.

Inserting the housing of the gas sensing module into the docking station includes lowering the housing into the docking station such that the connecting posts extend into pneumatic ports formed in the housing.

Establishing the mechanical connection includes lowering the housing into the docking station such that a connector associated with the docking station engages a portion of the housing thereby mechanically securing the housing in the docking station.

Engaging first connecting portions of a first pair of arms forming at least part of the connector with the housing, the housing pushing the first pair of arms apart to widen a first gap between the first pair of arms; lowering the housing such that the first connecting portions slide over sides of the housing; and engaging a first receiving portion of the housing with the first connecting portions.

Engaging second connecting portions of a second pair of arms forming at least part of the connector with the housing, the housing pushing the second pair of arms apart to widen a second gap between the second pair of arms; lowering the housing such that the second connecting portions slide over sides of the housing; and engaging a second receiving portion of the housing with the second connecting portions.

Locking the housing in the docking station by rotating a fastener between an unlocked state and a locked state.

A gas sensing module for a gas analyzer includes a sensor disposed within a housing of the gas sensing module, the sensor configured to generate signals regarding gas within a pneumatic flowpath of the gas sensing module; and a programmable module circuitry disposed within the housing of the gas sensing module, wherein the programmable module circuitry stores configuration data for the gas sensing module.

The gas sensing module of the preceding paragraph can optionally include, additionally and/or alternatively, any one or more of the following features, configurations and/or additional components:

The programmable module circuitry is disposed on a circuit board positioned between a base of the housing and the sensor.

The programmable module circuitry is configure to receive the signals from the sensor; and generate data regarding the gas based on the signals received from the sensor.

The programmable module circuitry is further configured to communicate the data regarding the gas to an analyzer controller of the gas analyzer.

The programmable module circuitry is further configured to receive pressure data from a pressure sensor of the gas analyzer; and generate data regarding the gas based at least in part on the pressure data from the pressure sensor.

The programmable module circuitry is configured to both receive data from analyzer controller of the gas analyzer and transmit data to the analyzer controller of the gas analyzer.

The programmable module circuitry is configured to store characterization data regarding the sensor.

Spring pins projecting out of the housing, the spring pins electrically connected to a baseboard of the gas analyzer to provide power to the microcontroller and to transmit data between the baseboard and the microcontroller.

The gas sensing module is configured to mount to a docking station disposed within the gas analyzer.

The gas sensing module is configured to mount to any one of a plurality of docking stations within the gas analyzer.

The programmable module circuitry is configured to receive a unique identifier from a processor of the gas analyzer; and identify data generated by the gas sensing module with the unique identifier.

A gas sensing module for a gas analyzer includes a module body including a pneumatic inlet port and a pneumatic outlet port; a pneumatic chamber fluidly connected to the pneumatic inlet port and the pneumatic outlet port; a sensor mounted to the module body adjacent the pneumatic chamber, the sensor configured to generate signals regarding gas within the pneumatic chamber; and a programmable module circuitry operatively connected to the sensor to receive the signals and configured to generate data regarding the gas based on the signals.

The gas sensing module of the preceding paragraph can optionally include, additionally and/or alternatively, any one or more of the following features, configurations and/or additional components:

A collar supporting the sensor and connected to the module body, such that the sensor is mounted to the module body by the collar.

The collar is connected to the module body by interfaced threading.

At least a portion of the sensor extends through the collar such that an end of the portion extending through the collar is disposed adjacent the pneumatic chamber.

A seal disposed between the sensor and the module body to seal the pneumatic chamber.

The collar is connected to the module body by interfaced threading.

A release assembly supported by the module body, the release assembly configured to mechanically disengage the gas sensing module from the gas analyzer.

The release assembly includes a release mechanism and a release spring disposed between the release mechanism and the module body.

The release assembly includes a fastener configured to rotate less than a full turn between a locked state and an unlocked state.

The sensor is a chemical cell.

The sensor includes an infrared (IR) emitter disposed at a first end of the pneumatic chamber; and an IR detector disposed at a second end of the pneumatic chamber.

A gas sensing module for a gas analyzer includes a first module body including a pneumatic inlet port; a second module body including a pneumatic outlet port; a pneumatic chamber extending between the first module body and the second module body and fluidly connected to the pneumatic inlet port and the pneumatic outlet port; a sensor configured to generate signals regarding gas within the pneumatic chamber; and a first microcontroller. The sensor includes an infrared (IR) emitter disposed at a first end of the pneumatic chamber; and an IR detector disposed at a second end of the pneumatic chamber, the IR detector configure to generate the signals. The microcontroller is operatively connected to the IR detector to receive the signals and configured to generate data regarding the gas based on the signals.

The gas sensing module of the preceding paragraph can optionally include, additionally and/or alternatively, any one or more of the following features, configurations and/or additional components:

A first housing connected to the first module body; a first cap connected to the first housing and the first module body to define a first chamber; a second housing connected to the second module body; and a second cap connected to the second housing and the second module body to define a second chamber that the first microcontroller is disposed in.

The pneumatic chamber is formed in a gas tube extending between the first module and the second module.

A gas analyzer configured to receive gas and generate data regarding the gas includes a housing having a front side, a back side, first and second lateral sides, and first and second longitudinal sides; a gas inlet configured to provide gas to a pneumatic pathway in the housing; a gas outlet configured to exhaust gas from the pneumatic pathway; a first module carrier frame disposed within the housing, the first module carrier frame defining a first plurality of docking stations; a first module disposed in the housing and mounted to a first docking station of the first plurality of docking stations; and the pneumatic pathway extends serially through the first plurality of docking stations.

The gas analyzer of the preceding paragraph can optionally include, additionally and/or alternatively, any one or more of the following features, configurations and/or additional components:

The first module is a gas sensing module configured to generate data regarding a parameter of the gas.

The parameter includes at least one of a gas concentration and a gas pressure.

A baseboard disposed beneath each the first module carrier frame, wherein each of the first plurality of modules and the second plurality of modules are electrically connected to the baseboard.

The first module is mountable within any one of the first plurality of docking stations.

The first module includes onboard programmable module circuitry.

A gas analyzer configured to receive gas and generate data regarding the gas includes a housing having a front side, a back side, first and second lateral sides, and first and second longitudinal sides; a first gas inlet configured to provide gas to a pneumatic pathway in the housing; a first gas outlet configured to exhaust gas from the pneumatic pathway; at least one module docking station disposed in the housing and pneumatically connected to the pneumatic pathway; a battery receiving slot formed on the back side of the housing; and a battery pack removably disposed in the battery receiving slot, the battery pack configured to provide power to the at least one module docking station.

The gas analyzer of the preceding paragraph can optionally include, additionally and/or alternatively, any one or more of the following features, configurations and/or additional components:

A pump disposed in the housing, the pump configured to draw gas through the gas inlet and pump the gas through the pneumatic pathway; the battery pack provides power to the pump.

The battery slot is elongated between the first and second longitudinal sides.

The battery slot includes an open end through the second longitudinal side.

The second longitudinal side is a bottom side of the gas analyzer.

The first gas inlet and the first gas outlet are disposed on the first longitudinal side.

A second gas inlet and a second gas outlet each mounted on the first longitudinal side, wherein the second gas inlet and the second gas outlet are pneumatically connected to a pressure sensor mounted within the housing The battery pack is configured to mount within the battery slot by sliding into the battery slot through the open end.

The battery pack is configured to slidably mount within the battery slot.

The battery pack is configured to vertically mount within the battery slot.

The battery slot is disposed laterally between a first portion of the pneumatic pathway and a second portion of the pneumatic pathway.

The at least one module docking station includes a first plurality of docking stations and a second plurality of docking stations, and wherein the battery slot is disposed between the first plurality of docking stations and the second plurality of docking stations.

The pneumatic pathway is pneumatically connected to the first plurality of docking stations and the second plurality of docking stations.

At least one gas sensing module is mounted at a first docking station of the at least one docking station.

The battery pack is rechargeable.

The battery pack includes a circuit board electrically connected to a plurality of battery cells.

At least one resistor is disposed on the circuit board.

The at least one resistor comprises a plurality of resistors disposed in series.

The plurality of battery cells are disposed on a first side of the circuit board and the plurality of resistors are disposed on a second side of the circuit board opposite the first side.

The second side of the circuit board is oriented towards the front side of the housing such that the plurality of resistors are disposed between the circuit board and the front side.

A user interface having a touchscreen display disposed on the front side, the battery pack configured to provide power to the touchscreen display.

The battery slot is elongate between the first longitudinal side and the second longitudinal side and disposed on a longitudinal centerline of the gas analyzer.

A battery fitment sensor electrically connected to an analyzer controller of the gas analyzer, the battery fitment sensor configured to initiate power-down of the gas analyzer based on actuation of the battery fitment sensor.

A gas analyzer configured to receive gas and generate data regarding the gas includes a housing having a front side, a back side, first and second lateral sides, and first and second longitudinal sides; a pair of sensor module arrays located within the housing; and a removable battery located directly between the pair of sensor module arrays.

The gas analyzer of the preceding paragraph can optionally include, additionally and/or alternatively, any one or more of the following features, configurations and/or additional components:

Each module array is oriented parallel with an axis, the battery is elongate parallel with the axis.

A pneumatic pathway extends through each of the sensor module arrays.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A handheld gas analyzer comprising:
a housing;
a gas inlet fluidly connected to a pneumatic circuit and a gas outlet fluidly connected to the pneumatic circuit, the pneumatic circuit disposed within the housing;
a plurality of internal bays within the housing;
a plurality of gas sensor modules, wherein a first subset of the plurality of gas sensor modules are configured to mount in the plurality of bays, each sensor module of the plurality of gas sensor modules comprising:
a transducer for measuring a respective gas property; and
programmable module circuitry configured to process signal information from the transducer and output data;
an analyzer controller within the housing, the analyzer controller configured to receive the data output from the plurality of gas sensor modules; and
wherein the pneumatic circuit runs serially through each of the plurality of gas sensor modules such that gas received through the gas inlet flows through each of the plurality of gas sensor modules between the gas inlet and the gas outlet.

2. The handheld gas analyzer of claim 1, wherein the programmable circuitry of each of the plurality of gas sensor modules is configured to apply a different calibration factor, wherein the calibration factor is factory set based on a measured output from the transducer.

3. The handheld gas analyzer of claim 1, wherein the analyzer controller is configured to associate a first unique identifier with data output from a first module of the plurality of gas sensor modules, and wherein the analyzer controller is further configured to save the unique identifier associated with the data output from the first module to generate first associated sensor data.

4. The handheld gas analyzer of claim 3, wherein the first unique identifier is stored in the programmable module circuitry of the first module.

5. The handheld gas analyzer of claim 4, wherein the analyzer controller includes transmission circuitry configured to transmit the first associated sensor data to a remote computing device.

6. The handheld gas analyzer of claim 3, wherein the analyzer controller is further configured to associate site data with the first associated sensor data, thereby generating sample-specific data.

7. The handheld gas analyzer of claim 1, further comprising:
a user interface configured to send information to the analyzer controller and receive information from the analyzer controller.

8. The handheld gas analyzer of claim 7, wherein the analyzer controller is configured to receive a unique module identifier associated with a first module of the plurality of gas sensor modules via the user interface.

9. The handheld gas analyzer of claim 7, wherein the analyzer controller is further configured to determine if a first unique module identifier associated with a first module of the plurality of gas sensor modules is stored on the programmable module circuitry of the first module.

10. The handheld gas analyzer of claim 9, wherein the analyzer controller is further configured to provide a prompt to the user interface, the prompt requesting the first unique module identifier.

11. The handheld gas analyzer of claim 7, wherein the user interface is integrated into the housing.

12. The handheld gas analyzer of claim 1, further comprising:
a second subset of the plurality of gas sensor modules disposed at least partially outside of the housing.

13. The handheld gas analyzer of claim 12, wherein a first sensor module of the second subset of the plurality of gas sensor modules is disposed outside of the housing and connected to the analyzer controller via one of a wired communication link and a wireless communication link.

14. The handheld gas analyzer of claim 1, wherein a first module of the first subset of the plurality of gas sensing modules includes:
- a module housing;
- a pneumatic chamber;
- a first pneumatic port fluidly connected to the pneumatic chamber;
- a second pneumatic port fluidly connected to the pneumatic chamber;
- a first transducer disposed adjacent the pneumatic chamber; and
- an electric connector projecting from the gas sensing module;
- wherein the gas sensing module is configured to form a pneumatic connection via the first and second pneumatic ports, a mechanical connection, and an electrical connection via the electrical connector by insertion of the first module into a first bay of the plurality of internal bays.

15. The handheld gas analyzer of claim 14, wherein the electrical connection is formed between a baseboard of the handheld gas analyzer and the electrical connector.

16. The handheld gas analyzer of claim 14, wherein the plurality of internal bays are formed in a module carrier frame disposed in the housing.

17. The handheld gas analyzer of claim 16, wherein the mechanical connection is actuatable between a locked state, locking the module housing within the first bay, and an unlocked state, allowing removal of the module housing from the first bay.

* * * * *